(12) United States Patent
Ge et al.

(10) Patent No.: US 10,975,166 B2
(45) Date of Patent: Apr. 13, 2021

(54) INHIBITORY ANTIBODIES AGAINST MMP-14

(71) Applicant: The Regents of the University of California, Oakland, CA (US)

(72) Inventors: Xin Ge, Riverside, CA (US); Dong Hyun Nam, Riverside, CA (US); Tyler Lopez, Riverside, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/223,943

(22) Filed: Dec. 18, 2018

(65) Prior Publication Data
US 2019/0185581 A1    Jun. 20, 2019

Related U.S. Application Data

(63) Continuation of application No. PCT/US2017/022341, filed on Mar. 14, 2017.

(60) Provisional application No. 62/403,589, filed on Oct. 3, 2016.

(51) Int. Cl.
*C07K 16/40*    (2006.01)
*A61K 39/00*    (2006.01)
*A61P 35/00*    (2006.01)

(52) U.S. Cl.
CPC ........... *C07K 16/40* (2013.01); *A61P 35/00* (2018.01); *A61K 2039/505* (2013.01); *C07K 2317/21* (2013.01); *C07K 2317/22* (2013.01); *C07K 2317/55* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 7,767,206 B2 | 8/2010 | Tocker et al. |
| 2007/0217997 A1 | 9/2007 | Devy et al. |

FOREIGN PATENT DOCUMENTS

| | | |
|---|---|---|
| WO | 2013106485 A2 | 7/2013 |
| WO | 2015050959 A1 | 4/2015 |

OTHER PUBLICATIONS

MacCallum et al., Antibody antigen Interactions: Contact Analysis and Binding Site Topography, J. Mol. Biol. 262, 732-745 1996. (Year: 1996).*
Vajdos et al., Comprehensive Functional Maps of the Antigen binding Site of an Anti-ErbB2 Antibody Obtained with Shotgun Scanning Mutagenesis, J. Mol. Biol. 320, 415-428, 2002. (Year: 2002).*
Padlan et al., Structure of an antibody-antigen complex: crystal structure of the HyHEL-10 Fab-lysozyme complex, PNAS, 86, 5938-5942, 1989. (Year: 1989).*
Lloyd et al., Protein Engineering, Design & Selection 22, 159-168, 2009. (Year: 2009).*
Botkjaer, K , et al., "Development of a specific affinity-matured exosite inhibitor to MT1-MMP that efficiently inhibits tumor cell invasion in vitro and metastasis in vivo", Oncotarget 7(13), 16773-16792 (2016).
Castro , et al., "Inhibition of Matrix Metalloproteinases (MMPs) as a Potential Strategy to Ameliorate Hypertension-Induced Cardiovascular Alterations", Curr Drug Targets 14(3), 335-343 (2013).
Cook , et al., "Defective Extracellular Matrix Reorganization by Chronic Wound Fibroblasts is Associated with Alterations in TIMP-1, TIMP-2, and MMP-2 Activity", J Invest Dermatol 115(2), 225-233 (2000).
Decock, J , et al., "Matrix metalloproteinases: protective roles in cancer", Cell Mol Med 15(6), 1254-1265 (2011).
Deu, E , et al., "New tools for dissecting protease function: implications for inhibitor design, drug discover and probe development", Nat Struct Mol Biol 19(1), 9-16 (2012).
Dev , et al., "Therapeutic potential of matrix metalloprotease inhibitors in neuropathic pain", Expert Opin Investig Drugs 19(4), 455-468 (2010).
Drag, M , et al., "Emerging principles in protease-based drug discovery", Nat Rev Drug Discov 9(9), 690-701 (2010).
Elkington, P , et al., "The paradox of matrix metalloproteinases in infectious disease", Clin Exp Immunol 142(1), 12-20 (2005).
Gialeli , et al., "Roles of matrix metalloproteinases in cancer progression and their pharmacological targeting", FEBS J 278(1), 16-27 (2011).
Liu, Y , et al., "Increased matrix metalloproteinase-9 predicts poor wound healing in diabetic foot ulcers", Diabetes Care 32(1), 117-119 (2009).
Lopez, T , et al., "Identification of Highly Selective MMP-14 Inhibitory Fabs by Deep Sequencing", Biotechnol Bioeng 114(6), 1140-1150; and 7 pages of Supporting Information (2017).
Lopez, T , "Selection of Inhibitory Antibodies Using Next Generation High Throughput Sequencing", 251st ACS National Meeting and Exposition, San Diego, CA, presentation, 23 pages (Mar. 15, 2016).
Nam, D , et al., "Active-site MMP-selective antibody inhibitors discovered from convex paratope synthetic libraries", Proc Natl Acad Sci 113(52), 14970-14975 (2016).
Nam, D , "Generation of Highly Selective Monoclonal Antibodies Inhibiting Tumorigenic Proteases", UC Riverside. Retrieved from https://escholarship.org/uc/item/0pd6m2b9, 148 pages, Jun. 2015.
Nam, D , et al., "Generation of Protease-Inhibiting Monoclonal Antibodies By Novel Paratope Design", American Institute of Chemical Engineers (AIChE) Annual Meeting, Salt Lake City, UT, presentation, 25 pages (Nov. 2015).

(Continued)

*Primary Examiner* — Elly-Gerald Stoica
(74) *Attorney, Agent, or Firm* — Viksnins Harris Padys Malen LLP

(57) ABSTRACT

Certain embodiments of the invention provide an antibody, or a fragment thereof, comprising a heavy chain complementarity-determining region 3 (CDR-H3) having at least about 80% sequence identity to a sequence described herein, as well as methods of use thereof.

9 Claims, 20 Drawing Sheets

Specification includes a Sequence Listing.

(56) References Cited

OTHER PUBLICATIONS

Overall, et al., "Tumour microenvironment—opinion: validating matrix metalloproteinases as drug targets and anti-targets for cancer therapy", Nat Rev Cancer 6(3), 227-239 (2006).
Patent Cooperation Treaty, International Searching Authority, Search Report and Written Opinion for PCT/US2017/02341, 11 pages, dated Oct. 30, 2017.
Turk, B, "Targeting proteases: successes, failures and future prospects", Nat Rev Drug Discov 5(9), 785-799 (2006).
Vanlaere, I, et al., "Matrix Metalloproteinases as Drug Targets in Infections Caused by Gram-Negative Bacteria and in Septic Shock", Clin Microbiol Rev 22(2), 224-239 (2009).
Wang, F, et al., "Reshaping Antibody Diversity", Cell 153(6), 1379-1393 (2013).
Zucker, et al., "Selective matrix metalloproteinase (MMP) inhibitors in cancer therapy: ready for prime time?", Cancer Biol Ther 8(24), 2371-2373 (2009).

* cited by examiner

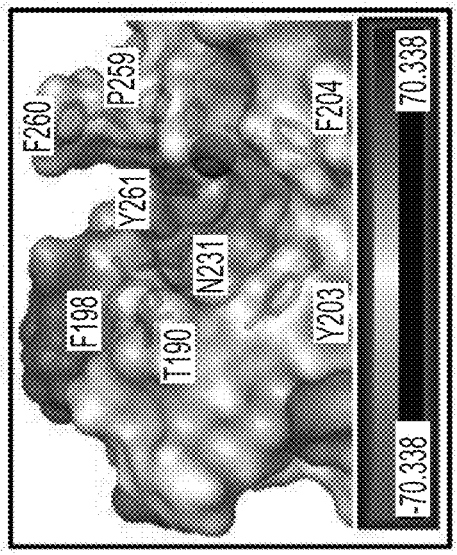
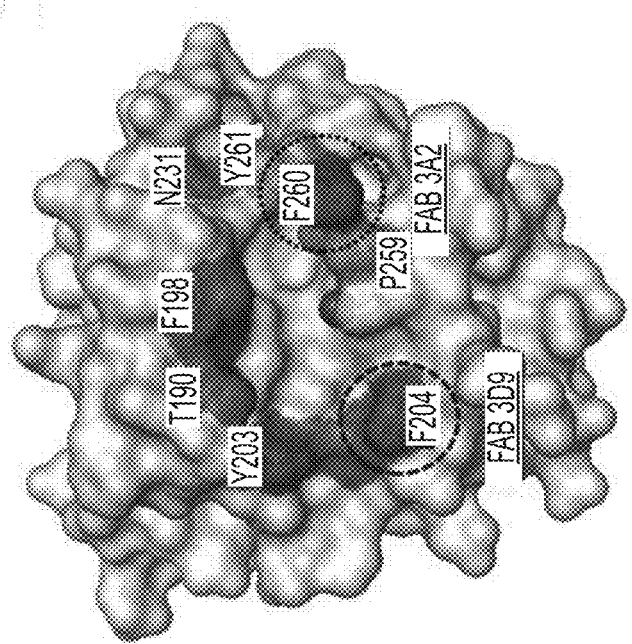
FIGURE 5B
FIGURE 5A

| | CLONE | CDRH3 | LENGTH | AFFINITY BY ELISA (nM) |
|---|---|---|---|---|
| 1 | S3G2 | YGYSAYWYALDY | 12 | 2 |
| 2 | S32A1 | FFYGSSSWYYSGAMDY | 16 | 3 |
| 3 | S32A9 | SHGYYSGLDY | 10 | 8 |
| 4 | S3B5 | GYSSYGYALDY | 11 | 2 |
| 5 | S3H2 | GVWYSSAMDY | 10 | 2 |
| 6 | S33E8 | YSHPFWSAMDY | 11 | 4 |

```
MMP_2   ------RKPKWDKNQITYRIIGYTPDLDPETVDDAFARAFQVWSDVTPLRFSRI------
MMP_9   MFQTFEGDLKWHHHNITYWIQNYSEDLPRAVIDDAFARAFALWSAVTPLTFTRV------
MMP_14  ------IQGLKWQHNEITFCIQNYTPKVGEYATYEAIRKAFRVWESATPLRFREVPYAYIR
                  T190        F198  Y203/F204

MMP_2   --HDGEADIMINFGRWEHGDGYPFDGKDGLLAHAFAPGTGVGGDSHFDDDELWSLGKG--
MMP_9   --YSRDADIVIQFGVAEHGDGYPFDGKDGLLAHAFPPGPGIQGDAHFDDDELWSLGKG--
MMP_14  EGHEKQADIMIFFAEGFHGDSTPFDGEGGFLAHAYFPGPNIGGDTHFDSAEPWTVRNEDL
        N231                                F260

MMP_2   VGYSLFLVAAHEFGHAMGLEHSQDPGAIMAPIYTY--TKNFRLSQDDIKGIQELYGASP
MMP_9   QGYSLFLVAAHEFGHAIGLDHSSVPEAIMYPMYRF--TEGPPLHKDDVNGIRHLY----
MMP_14  NGNDIFLVAVHELGHAIGLEHSSDPSAIMAPFYQWMDTENFVLPDDDRRGIQQLYGGES
              ACTIVE SITE              S1'
```

FIGURE 11

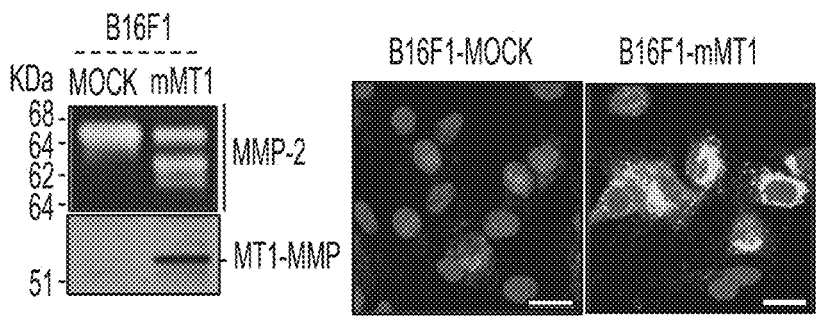
FIGURE 12A
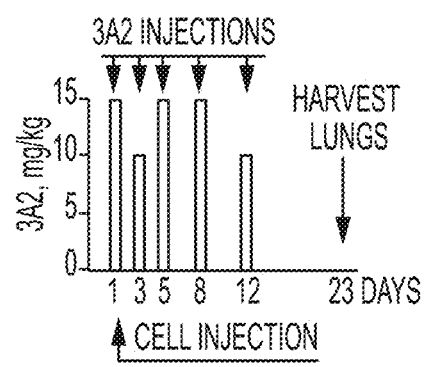
FIGURE 12B
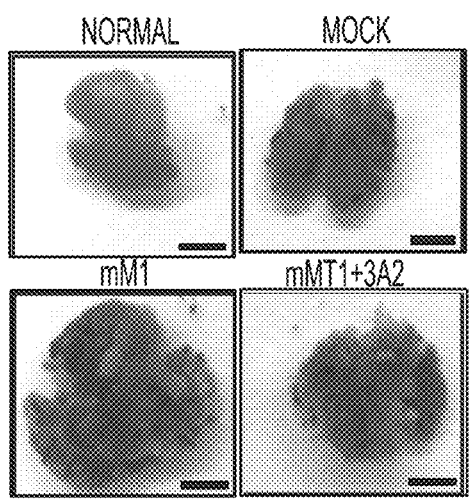
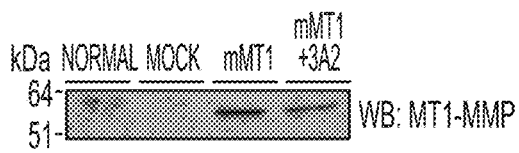
FIGURE 12C
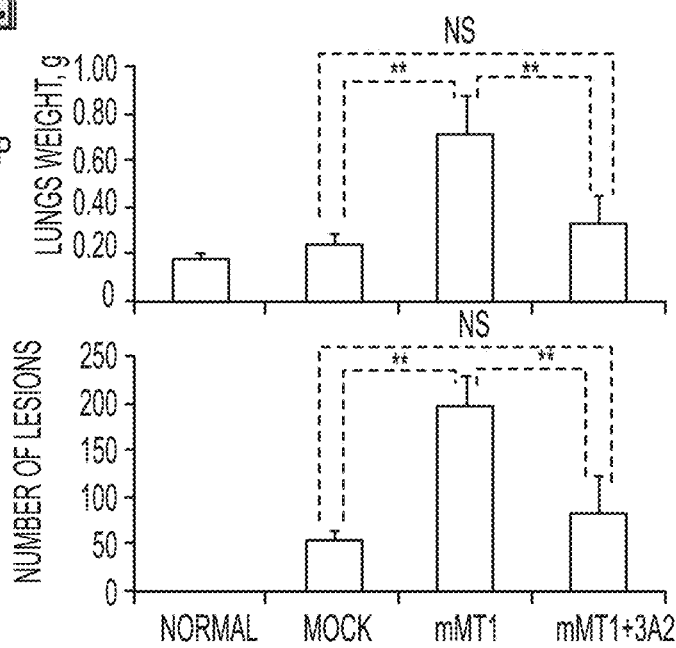
FIGURE 12D

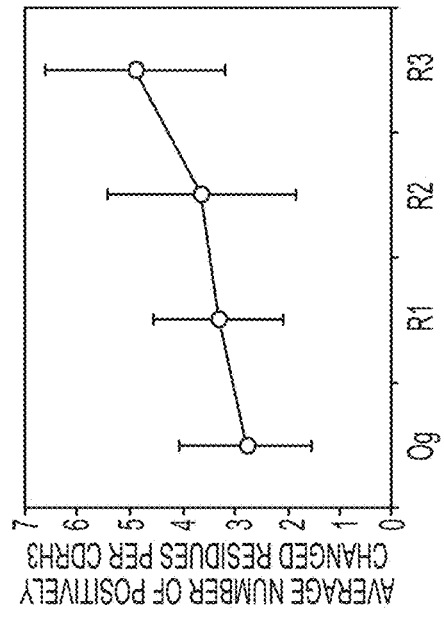
FIGURE 15A
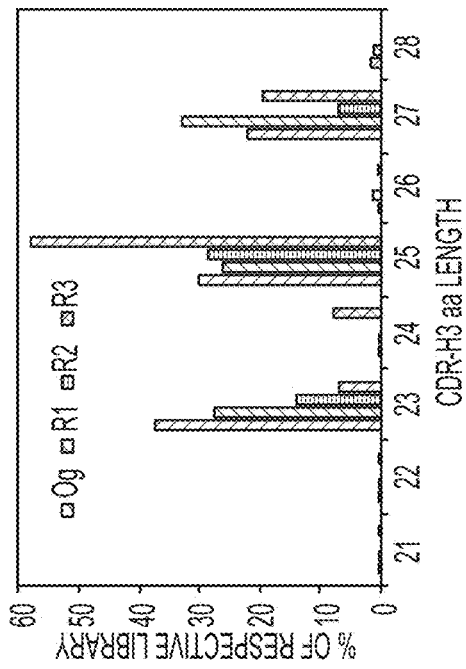
FIGURE 15B
| | 92 | 93 | 94 | 95 | 96 | 97 | 98 | 99 | 100 | 100A | 100B | 100C | 100D | 100E | 100F | 100G | 100H | 100I | 100J | 100K | 100L | 100M |
|---|---|---|---|---|---|---|---|---|---|---|---|---|---|---|---|---|---|---|---|---|---|---|
| POSITIVELY CHARGED | -11 | -14 | 28 | -3 | 6 | 15 | -7 | 28 | 25 | -5 | -7 | 29 | 17 | -2 | -2 | 1 | 2 | -4 | 0 | 15 | 2 | 0 |
| NEGATIVELY CHARGED | -11 | 2 | -5 | -4 | -4 | 0 | -6 | -6 | -4 | -6 | -5 | -5 | -6 | -4 | -4 | -2 | -4 | 22 | -5 | -2 | 8 | 1 |
| POLAR | 24 | 13 | -4 | -8 | 30 | 22 | 0 | 11 | -12 | -6 | 33 | 11 | 15 | 18 | 10 | 5 | -5 | 12 | 10 | -5 | 6 | 0 |
| HYDROPHOBIC | -19 | 8 | -5 | 2 | -31 | -25 | 23 | -27 | 2 | -19 | -18 | -26 | -20 | -2 | 0 | 5 | 20 | -27 | -6 | -22 | -19 | -12 |
FIGURE 15C

INHIBITORY ANTIBODIES AGAINST MMP-14

RELATED APPLICATION

This application is a continuation of International Application Serial No. PCT/US2017/022341, filed Mar. 14, 2017, which claims the benefit of priority of U.S. Provisional Application Ser. No. 62/403,589, filed on Oct. 3, 2016, which applications are incorporated by reference herein.

GOVERNMENT FUNDING

This invention was made with Government support under Grant No. GM115672 awarded by the National Institutes of Health; and Grant No. 1453645 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Mar. 28, 2017, is named 12111_005US1_SL.txt and is 184,468 bytes in size.

BACKGROUND OF THE INVENTION

As key cellular proteinases, matrix metalloproteinase (MMP) family members control various physiological and pathological processes. Multiple diseases are associated with altered MMP expression and aberrant proteolysis, including cancer (Overall et al., (2006) *Nat Rev Cancer* 6(3):227-239), wound healing (Cook et al., (2000) *J Invest Dermatol* 115(2):225-233, Liu et al. (2009) *Diabetes Care* 32(1):117-119), inflammation diseases (Elkington et al., (2005) *Clin Exp Immunol* 142(1):12-20, Vanlaere et al., (2009) *Clin Microbiol Rev* 22(2):224-239), neurological pain (Dev et al., (2010) *Expert Opin Investig Drugs* 19(4): 455-468), and hypertension (Castro et al., (2013) *Curr Drug Targets* 14(3):335-343). There is a consensus among researchers that the individual MMPs are promising drug targets in diversified pathologies, and that inhibitor specificity is required for selective and successful MMP therapies (Deu et al., (2012) *Nat Struct Mol Biol* 19(1):9-16; Drag et al., (2010) *Nat Rev Drug Discov* 9(9):690-701; Botkjaer et al., (2016) *Oncotarget* 7(13):16773-16792). However, achieving target specificity and selectivity in small-molecule MMP inhibitors is exceedingly difficult. Because the catalytic mechanism and the catalytic domain fold are conserved among the MMP/ADAM (a disintegrin and metalloproteinase)/ADAMTS (ADAM with thrombospondin motifs) superfamily members, the available small molecule inhibitors (most frequently, active site zinc-chelating hydroxamates) target multiple proteinases resulting in off-target side effects (Deu et al., (2012) *Nat Struct Mol Biol* 19(1):9-16; Turk B (2006) *Nat Rev Drug Discov* 5(9):785-799; Zucker et al., (2009) *Cancer Biol Ther* 8(24):2371-2373). This is problematic given that some MMPs (e.g., MMP-14) are always pro-tumorigenic while some other MMPs are anti-tumorigenic in certain cancer microenvironments (Gialeli et al., (2011) *FEBS J* 278(1):16-27; Decock et al., (2011) *J Cell Mol Med* 15(6):1254-1265). As a result, broad-spectrum hydroxamates have failed in cancer clinical trials due to their low overall efficacy and side effects (Turk B (2006) *Nat Rev Drug Discov* 5(9):785-799).

Accordingly, there is a need for new enzyme inhibitors (e.g., selective inhibitors), such as MMP inhibitors. Additionally, there is a need for new methods to identify such inhibitors (e.g., selective MMP inhibitors).

SUMMARY OF THE INVENTION

Accordingly, certain embodiments of the invention provide a recombinant antibody, or a fragment thereof, comprising a heavy chain complementarity-determining region 3 (CDR-H3) that is at least 18 amino acids in length, wherein the antibody or fragment thereof is an inhibitor of matrix metalloproteinase (MMP)-14.

Certain embodiments of the invention provide an antibody, or a fragment thereof, comprising a heavy chain complementarity-determining region 3 (CDR-H3) comprising an amino acid sequence having at least about 80% sequence identity to a sequence selected from the group consisting of:

```
                                         (SEQ ID NO: 29)
GWRVYADRGHVRGYFRVWYGMDY, (SEQ ID NO: 30)
IMKIKRNSLKFRGFVPLQMQYVMDY, (SEQ ID NO: 31)
KDLLKTNRLTTRYKKSVSVGYGMDY, (SEQ ID NO: 32)
SCVWACCACRYWSGSDSHYAMDY, (SEQ ID NO: 33)
PGRHLQTTFKGYQFKYSRYIYAMDY, (SEQ ID NO: 34)
VLNIFMDVGAARFPGLVRYGMDY, (SEQ ID NO: 36)
RYGSDVFCVGCFFGVRLSYVMDY, (SEQ ID NO: 37)
SDSWVQGRDFCYYSAWVGYGMDY, (SEQ ID NO: 38)
VSNRYNRSSASIAGLQLFRPYGMDY, (SEQ ID NO: 39)
FKNADFAAGGQWSKMLIARMYAMDY, (SEQ ID NO: 43)
HSRDGWQHWFGNWAGLHSYGMDY, (SEQ ID NO: 44)
HCLLRSRRCEMSTKTRELNVYRYAMDY, (SEQ ID NO: 45)
GSLRRDFNLVVRSSWDIRSNYVMDY, (SEQ ID NO: 46)
WLRVSLKSGVYKVLARAVELDEYVMDY,
and (SEQ ID NO: 47)
GVRGNKLRLLSSRSGRMESHYVMDY.
```

Certain embodiments of the invention provide an antibody, or a fragment thereof, comprising a heavy chain variable region ($V_H$) having at least about 80% sequence identity to a sequence selected from the group consisting of: SEQ ID NO:49, SEQ ID NO:51, SEQ ID NO:53, SEQ ID NO:55, SEQ ID NO:57, SEQ ID NO:59, SEQ ID NO:63, SEQ ID NO:67, SEQ ID NO:69, SEQ ID NO:71, SEQ ID NO:73, SEQ ID NO:75, SEQ ID NO:77, SEQ ID NO:81, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:111, SEQ ID NO:113, SEQ ID NO:115, SEQ ID NO:117 and SEQ ID NO:119.

Certain embodiments of the invention provide a composition comprising an antibody, or fragment thereof, as described herein and physiologically-acceptable, non-toxic carrier.

Certain embodiments of the invention provide a nucleic acid encoding an antibody, or fragment thereof, as described herein.

Certain embodiments of the invention provide an expression cassette comprising a nucleic acid described herein.

Certain embodiments of the invention provide a vector (e.g., a phagemid) comprising the expression cassette described herein.

Certain embodiments of the invention provide a cell comprising a vector described herein.

Certain embodiments of the invention provide a phage particle comprising a vector described herein.

Certain embodiments of the invention provide a method of inhibiting the enzymatic activity of matrix metalloproteinase (MMP)-14, comprising contacting MMP-14 with an antibody, or a fragment thereof, as described herein.

Certain embodiments of the invention provide a method for treating cancer in a mammal, comprising administering an effective amount of an antibody, or a fragment thereof, as described herein to the mammal.

Certain embodiments of the invention provide an antibody, or a fragment thereof, as described herein for the prophylactic or therapeutic treatment of cancer.

Certain embodiments of the invention provide the use of an antibody, or a fragment thereof, as described herein to prepare a medicament for the treatment of cancer in a mammal. Certain embodiments of the invention provide an antibody, or a fragment thereof, as described herein for use in medical therapy.

Certain embodiments of the invention provide a kit comprising antibody, or a fragment thereof, as described herein, packaging material, and instructions for administering the antibody, or a fragment thereof, to a mammal to treat cancer.

The invention also provides processes and intermediates disclosed herein that are useful for preparing an antibody of the invention, or a fragment thereof.

BRIEF DESCRIPTION OF THE FIGURES

(FIG. 2A) Dose-response curves of binding affinity (circle) and inhibition $IC_{50}$ (triangle) of purified Fabs. 1 µM of quenched-fluorescent substrate peptide and 1 nM cdMMP-14 were used in FRET inhibition assays. (FIG. 2B) Binding selectivity toward MMP-14 (circles) over MMP-2 (triangles) and MMP-9 (squares) tested by ELISA.

(FIG. 3A) Binding kinetics of 10 nM (dotted line), 15 nM (long dashed line), and 20 nM (solid line) Fab 3A2 to cdMMP-14 measured by surface plasmon resonance. In average, $K_{on}$=3.68×10$^5$ (1/Ms), $K_{off}$=1.79× 10$^{-3}$ (1/s), and $K_D$=4.76 nM. (FIG. 3B) Fab 3A2 inhibited cdMMP-14 proteolytic activity on the peptide substrate with a potency of 9.7±1.2 nM, of the same order of magnitude as n-TIMP-2 (5.1±2.4 nM) and GM6001 (2.1±0.6 nM). (FIG. 3C) Competitive ELISA of Fab 3A2 with n-TIMP-2. Two folds serially diluted n-TIMP-2 (starting at 12 µM) and Fab 3A2 at fixed 10 nM were incubated with biotinylated cdMMP-14 immobilized on streptavidin coated wells, then detected by anti-Fab-HRP. 3A2 directly competed with n-TIMP-2 when binding to MMP-14, suggesting that their binding sites were at least partially overlapped. (FIG. 3D) Lineweaver-Burk plots of MMP-14 with 0, 250, 500 nM Fab 3A2. Unaltered $V_{max}$ and increased $K_m$ in the presence of Fab indicate a typical competitive inhibition. (FIG. 3E) Epitope determination by competitive ELISA and inhibition assays. Six MMP-14 single-site mutants (T190A, F198A, Y203A, F204A, N231A and F260A) were functionally expressed in periplasmic space of E. coli without refolding. 10 nM Fab 3A2 was incubated with increasing amounts of MMP-14 mutant and captured by surface immobilized wild-type MMP-14. The dose-response curves were generated by detecting bound 3A2 with anti-Fab-HRP. All the mutants showed a binding response except F260A, demonstrating that F260 is important position for 3A2 binding. Inhibition assay was performed using 50 nM MMP-14 mutant, 5 µM Fab 3A2, and 1 µM quenched fluorescent substrate.

(FIG. 4A) Gelatin zymography of MMP-14-dependent activation of pro-MMP-2. (FIG. 4B) Fab 3A2 inhibition on degradation of type I collagen mediated by cellular MMP-14.

FIGS. 5A-B. Understanding inhibition mechanisms by structure interpretation. (FIG. 5A) Top view of cdMMP-14 reaction site. Three histidine residuals of catalytic motif (HEXXHXXGXXH (SEQ ID NO:1)) coordinate the catalytic zinc (sphere). P259, F260 and Y261 form the wall of S1' cleft, which is specific for each MMPs. Six mutation sites for epitope mapping are noted. F260 is a part of the specificity determining loop, but it is also a mutation site of chosen. Competitive ELISA and inhibition assays (FIG. 3E) suggested that 3A2 and 3D9 bound at F260 (circled in dotted line) and F204 (circled in dashed line) respectively. (FIG. 5B) Side view of MMP-14 reaction cleft and vicinity as electrostatic surface model. Protruding F260 is responsible for the formation of a relatively deep S1' cleft with the catalytic zinc (sphere) at the bottom of the cleft. The side chains of six mutation sites, specificity determining loop residues, and three histidnes chelating a $Zn^{2+}$, are displayed as sticks. The concave active site is predominately negatively charged. Images were generated using PyMOL based on MMP-14 crystal structure (PDB 1bqq).

(FIG. 6A) CDR-H3 length distributions. The CDR-H3 length of camelid antibodies shows a bimodal distribution, distinctly different from Gaussian distribution of human and murine antibodies with averages at 12 and 9 aa respectively. The sequences of antibodies were obtained from IMGT, Kabat and abYsis antibody databases, with numbers of sequences used for statistics indicated in the inserted table. (FIG. 6B) Amino acid compositions of human and camelid CDR-H3s and a customized degenerate codon called XYZ. Camelid antibodies carry more cysteine, less hydrophobic residues (Phe, Val, Ile), more positively charged residues (Arg, Lys), and more hydrophilic residues (Gly, Ser, Thr, Asn). To mimic these features, a degenerate codon XYZ was custom-designed to bias the diversity toward the amino acid usage in camelid CDR-H3 sequences. The inserted table indicates nucleotide proportions of XYZ at each of the three codon positions. For each amino acid, human is shown on the left, Camelid in the middle and XYZ on the right.

(FIG. 8A) Non-reducing SDS-PAGE of purified long CDR-H3 Fabs. Typical yields of Fabs were 0.5-2 mg/L in *E. coli* after purification. (FIG. 8B) SEC of purified Fab 3A2 using an analytical Superdex 75 10/300 GL column (GE Health). Fab 3A2 was monomeric without detectable level of aggregates.

(FIG. 10A) After phage panning toward MMP-14, monoclonal phage ELISA identified 6 unique Fab clones. CDR-H3 sequences and length are shown in the table. These Fabs were cloned, expressed, and purified for ELISA.

FIG. 10A discloses SEQ ID NOS 127-132, respectively, in order of appearance. (FIG. 10B) In FRET inhibition assay, 1 µM quenched-fluorescent substrate and 1 nM cdMMP-14 were used. Although all the isolated Fab showed excellent binding affinities, none of them exhibited inhibition function.

FIG. 11. Sequence alignment of catalytic domains of human MMP-2 (SEQ ID NO:133), -9 (SEQ ID NO:134) and -14 (SEQ ID NO:135). The active site (HEXXHXXGXXH (SEQ ID NO:1)) and the S1' regions are underlined. The mutation sites chosen for epitope mapping are boxed. Identity residues are marked with asterisk (*). The residues of strong similarity are marked with colon (:). The residues of weakly similarity are marked with period (.). The residues of non-identity are unmarked. Sequence identity among three MMPs is 37.43%. Sequence similarity among three MMPs is 29.05%.

FIGS. 12A-D. The 3A2 Fab reduces both the frequency and the size of melanoma metastatic nodules in mice. FIG. 12A, Left, The status of MMP-2 (gelatin zymography; top panel) and MT1-MMP (Western blotting with the AB8345 antibody; bottom panel) in B16F1-mock and B16F1-mMT1 cells. Right, the fluorescent MP-3653 reporter (25 nM) reports the presence of the catalytically active MT1-MMP in B16F1-mMT1 cells but not in B16F1-mock cells. DAPI. Scale bar, 10 FIG. 12B, Schematic representation of the injection protocol. Athymic mice received a single i.v. injection of B16F1-mock or B16F1-mMT1 on day 1 followed by the 3A2 Fab administration i.p. (10-15 mg/kg) on days 1-12. Mice were euthanized and the lungs harvested on day 23. FIG. 12C, Top, Representative images of the lungs obtained from the intact control, B16F1-mock, B16F1-mMT1 and B16F1-mock+3A2 animal groups. Scale bar, 5 mm. Bottom, Western blotting (WB) of the lung extracts (20 µg total protein each) using the MT1-MMP AB8345 antibody. FIG. 12D, The weight and the number of the pulmonary metastatic lesions in the B16F1-mock, B16F1-mMT1 and B16F1-mock+3A2 mice. Normal, the lungs from the intact mice control. **, P<0.05; NS, not significant.

FIGS. 15A-C. Antibody repertoire analysis of phage panned long CDR-H3 libraries. (FIG. 15A) CDR-H3 length distribution. (FIG. 15B) Enrichment of positively charged residues (R, H, K) at CDR-H3. (FIG. 15C) Amino acid composition changes at each position (92-100M) of CDR-H3 with 25 aa. Residues were grouped according to biochemical properties: positively charged (R, H, K), negatively charged (D, E), polar (S, T, N, Q), and hydrophobic (A, I, L, M, F, W, Y, V). The percentage changes from the library Og to R3 are listed, positions with >20% change were highlighted in bold boxes.

(FIG. 19A) Lineweaver-Burke plots of cdMMP-14 at the presence of 0, 150, 300 nM Fab R2C7. Unaltered $V_{max}$ and increased $K_m$ with increasing Fab concentrations indicate a competitive inhibition mode of R2C7. (FIG. 19B) Competitive ELISA with TIMP-2. Fab R2C7 was mixed with varying concentrations of TIMP-2 in solution before addition to an ELISA plate coated with 100 nM cdMMP-14, and the signals were developed by using anti-Fab-HRP and the associated substrate. (FIG. 19C) R2C7 epitope mapping by inhibition assays. Four positions T190, F198, F204, and F260 surrounding the catalytic cleft of cdMMP-14 were chosen for alanine mutagenesis. Compared to wt cdMMP-14, F260A and F204A cannot be inhibited by Fab R2C7. (FIG. 19D) R2C7 epitope image generated using PyMOL based on MMP-14 crystal structure (PDB 1bqq), showing the catalytic zinc (solid black), site-directed mutagenesis positions, the three histidine residues of the catalytic motif HEXXHXXGXXH (SEQ ID NO:1), and the residues forming the wall of S1' cleft. Determined locations of R2C7 binding are circled.

DETAILED DESCRIPTION

Figure 1:
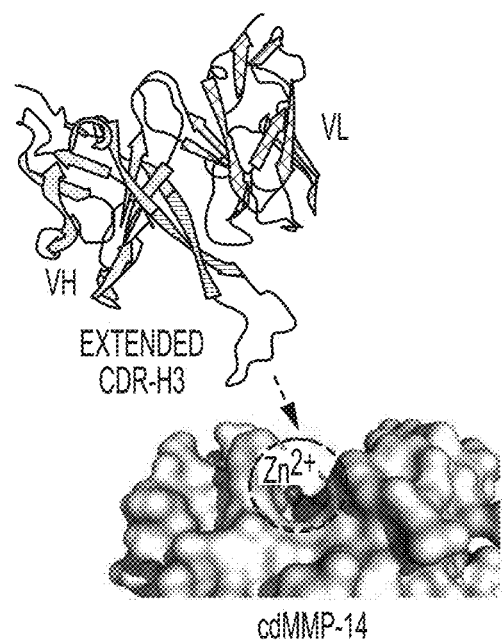
FIG. 1. Scheme that convex antibody paratope formed by an extended CDR-H3 mediates enzyme inhibition. The active site of matrix metalloproteinase-14 catalytic domain (cdMMP-14) has a concave structure with the catalytic $Zn^{2+}$ at the bottom of the pocket (sphere). Fab 3A2 ($V_H$—heavy chain; $V_L$—light chain) binds to cdMMP-14 reaction pocket through its long, 27 residue CDR-H3 loop. Model of Fab 3A2 was generated using antibody structure prediction server SAbPred (Dunbar, et al. (2016) Nucleic Acids Res, 44 (W1): W474-W478) based on 3A2 sequence (Table 2). Images were generated by using PyMOL.

Described herein is a general method for the discovery of monoclonal antibodies able to inhibit catalytic activities of enzymes (e.g. biomedically important proteases). This method has astonishingly high hit rates, e.g., >65% of isolated affinity antibodies are inhibitory, which is a significant improvement compared to current technologies for inhibitory antibody generation (a ~2% hit rate of inhibitory antibodies out of affinity clones). This method is achieved by creating custom-designed synthetic antibody libraries encoding ultra long CDRs (e.g. 20-30 aa long CDR-H3), which form convex shaped paratopes that directly bind to the concave structured active sites of target enzymes and block their catalytic function. Using this method, a panel of highly potent and high selective monoclonal antibody Fab fragments, which target matrix metalloproteinase (MMP)-14, has been discovered. For example, as described in the Examples, Fab 3A2 competitively inhibited MMP-14 at physiological environments with a binding affinity of 4.85 nM, an inhibition potency of Ki=10 nM, and selectivity of $>10^5$ over other highly homologous MMPs. This novel paratope design has great potential for many biomedically important but challenging targets to conventional antibody techniques.

Compositions of the Invention

Antibodies or Fragments Thereof

Certain embodiments of the invention provide an antibody or a fragment thereof (e.g., a recombinant antibody or fragment thereof) comprising a heavy chain complementarity-determining region 3 (CDR-H3) that is at least 18 amino acids in length. In certain embodiments, the antibody or fragment thereof is an inhibitor of matrix metalloproteinase (MMP)-14.

Thus, certain embodiments of the invention provide an antibody or a fragment thereof comprising a heavy chain complementarity-determining region 3 (CDR-H3) that is at least 18 amino acids in length, wherein the antibody or fragment thereof is an inhibitor of matrix metalloproteinase (MMP)-14.

The term "inhibitor of MMP-14" as used herein refers to an antibody or fragment thereof that is capable of inhibiting the function of MMP-14 (e.g., inhibits enzymatic activity, e.g., inhibits protease cleavage activity). For example, in certain embodiments, the antibody, or fragment thereof, detectably inhibits the biological activity of MMP-14 as measured, e.g., using an assay described herein. In certain embodiments, the antibody, or fragment thereof, inhibits the biological activity of MMP-14 by at least about 5%, at least about 10%, at least about 20%, at least about 30%, at least about 40%, at least about 50%, at least about 60%, at least about 70%, at least about 80%, or at least about 90%. In certain embodiments, the antibody or fragment thereof is a selective inhibitor of MMP-14. For example, an antibody of the invention may be at least 5, at least 10, at least 50, at least 100, at least 500, or at least 1,000 fold selective for MMP-14 over another MMP in a selected assay (e.g., an assay described in the Examples herein).

In certain embodiments, the CDR-H3 is between about 18 to about 50 amino acids in length. In certain embodiments, the CDR-H3 is between about 18 to about 40 amino acids in length. In certain embodiments, the CDR-H3 is between about 18 to about 30 amino acids in length. In certain embodiments, the CDR-H3 is between about 23 to about 27 amino acids in length. In certain embodiments, the CDR-H3 is about 23 amino acids in length. In certain embodiments, the CDR-H3 is about 25 amino acids in length. In certain embodiments, the CDR-H3 is about 27 amino acids in length.

In certain embodiments, the antibody or fragment thereof comprises a convex shaped paratope.

In certain embodiments, the antibody, or fragment thereof, comprises an amino acid sequence having at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a sequence described herein (e.g., a CDR-H3 sequence described herein).

In certain embodiments, the antibody, or fragment thereof, comprises an amino acid sequence (e.g., comprises a CDR-H3 sequence) having at least about 80% sequence identity to:

```
                                     (SEQ ID NO: 8)
VKLQKDKSHQWIRNLVATPYGRYVMDY, (SEQ ID NO: 9)
GIKGLVFTGSQMKMLRRGNYNWYVMDY, (SEQ ID NO: 10)
RLMAYHGSCSSRLCQTAISPQRYAMDY, (SEQ ID NO: 11)
IGVNAWAVKMSQRMLATRGSGWYVMDY, (SEQ ID NO: 12)
ATNEKFRRKSLQVRLLMRSWLAYAMDY, (SEQ ID NO: 13)
SKYGPASRQLASRTSWSGPRGKYGMDY, (SEQ ID NO: 14)
LYNGWLMVEGIGSAREGPTWYAMDY,
```

-continued

GVRGNKLRLLSSRSGLMESHYVMDY, (SEQ ID NO: 15)

SVHMKLSNKILSGWSWNNSFYAMDY, (SEQ ID NO: 16)

MSLHRNFNQQGRSRLLGRMPRTYGMDY, (SEQ ID NO: 17)

RPCKACRTRLELVRRGMDSGLRYGMDY, (SEQ ID NO: 18)

PTTSRVNKKLFRVSVLHPGSYGMDY, (SEQ ID NO: 19)

NGRYPGFLKRAHKRLLNFKAYVMDY, (SEQ ID NO: 20)

SQHAKKSTIIRMLEHQSRSGMQYVMDY, (SEQ ID NO: 21)

LDRDRYIHVGRAGNTYSNYYYVMDY, (SEQ ID NO: 22)

EIHMLSRQARYLRDGRRPRGSMYVMDY, (SEQ ID NO: 23)

GTSFQVRCVLYRLLSPGRYVMDY (SEQ ID NO: 24)

STAATTLSRMSRSYWTIQLPYGMDY, (SEQ ID NO: 25)

SARLRLRGNHDRRRSKSVYYRPYVMDY, (SEQ ID NO: 26)

NFRVESAGRPGKTVLRKDGKYAMDY, (SEQ ID NO: 27)

GWRVYADRGHVRGYFRVWYGMDY, (SEQ ID NO: 29)

IMKIKRNSLKFRGFVPLQMQYVMDY, (SEQ ID NO: 30)

KDLLKTNRLTTRYKKSVSVGYGMDY, (SEQ ID NO: 31)

SCVWACCACRYWSGSDSHYAMDY, (SEQ ID NO: 32)

PGRHLQTTFKGYQFKYSRYIYAMDY, (SEQ ID NO: 33)

VLNIFMDVGAARFPGLVRYGMDY, (SEQ ID NO: 34)

MAKDFRILASVRMWVLASRLYVMDY, (SEQ ID NO: 35)

RYGSDVFCVGCFFGVRLSYVMDY, (SEQ ID NO: 36)

SDSWVQGRDFCYYSAWVGYGMDY, (SEQ ID NO: 37)

VSNRYNRSSASIAGLQLFRPYGMDY, (SEQ ID NO: 38)

FKNADFAAGGQWSKMLIARMYAMDY, (SEQ ID NO: 39)

VGAWRVPSERMFTYPSARTRYAMDY, (SEQ ID NO: 40)

RDFGGFAGCLDGYVHVCWYAMDY, (SEQ ID NO: 41)

LAWKSDNRGSFAKLQFTLKMYGMDY, (SEQ ID NO: 42)

-continued

HSRDGWQHWFGNWAGLHSYGMDY, (SEQ ID NO: 43)

HCLLRSRRCEMSTKTRELNVYRYAMDY, (SEQ ID NO: 44)

GSLRRDFNLVVRSSWDIRSNYVMDY, (SEQ ID NO: 45)

WLRVSLKSGVYKVLARAVELDEYVMDY, (SEQ ID NO: 46)

GVRGNKLRLLSSRSGRMESHYVMDY (SEQ ID NO: 47)

or

MASIDLRMLSRMLAGPQFKVYGMDY. (SEQ ID NO: 48)

In certain embodiments, the antibody or fragment thereof comprises an amino acid sequence (e.g., comprises a CDR-H3 sequence) having at least about 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47 or SEQ ID NO:48.

In certain embodiments, the antibody or fragment thereof comprises an amino acid sequence (e.g., comprises a CDR-H3 sequence) having at least about 90% sequence identity to SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47 or SEQ ID NO:48.

In certain embodiments, the antibody or fragment thereof comprises an amino acid sequence (e.g., comprises a CDR-H3 sequence) having at least about 95% sequence identity to SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47 or SEQ ID NO:48.

In certain embodiments, the antibody or fragment thereof comprises an amino acid sequence (e.g., comprises a CDR-H3 sequence) having at least about 99% sequence identity to SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47 or SEQ ID NO:48.

In certain embodiments, the antibody or fragment thereof comprises SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47 or SEQ ID NO:48.

In certain embodiments, the antibody or fragment thereof comprises an amino acid sequence (e.g., a CDR-H3 sequence) having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:25, SEQ ID NO:27, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47 or SEQ ID NO:48.

In certain embodiments, the antibody or fragment thereof comprises an amino acid sequence (e.g., a CDR-H3 sequence) having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 or SEQ ID NO:27.

In certain embodiments, the antibody or fragment thereof comprises an amino acid sequence (e.g., a CDR-H3 sequence) having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or SEQ ID NO:21.

In certain embodiments, the antibody or fragment thereof comprises a CDR-H3 sequence consisting of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or SEQ ID NO:21.

In certain embodiments, the antibody or fragment thereof comprises an amino acid sequence (e.g., a CDR-H3 sequence) having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47 or SEQ ID NO:48.

In certain embodiments, the antibody or fragment thereof comprises an amino acid sequence (e.g., a CDR-H3 sequence) having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:29, SEQ ID NO:30, SEQ ID NO:31, SEQ ID NO:32, SEQ ID NO:33, SEQ ID NO:34, SEQ ID NO:36, SEQ ID NO:37, SEQ ID NO:38, SEQ ID NO:39, SEQ ID NO:42, SEQ ID NO:43, SEQ ID NO:44, SEQ ID NO:45, SEQ ID NO:46, SEQ ID NO:47 or SEQ ID NO:48.

In certain embodiments, the antibody or fragment thereof comprises an amino acid sequence (e.g., a CDR-H3 sequence) having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:29, SEQ ID NO:30, SEQ ID NO:31, SEQ ID NO:32, SEQ ID NO:33, SEQ ID NO:34, SEQ ID NO:36, SEQ ID NO:37, SEQ ID NO:38, SEQ ID NO:39, SEQ ID NO:43, SEQ ID NO:44, SEQ ID NO:45, SEQ ID NO:46 or SEQ ID NO:47.

In certain embodiments, the antibody or fragment thereof comprises an amino acid sequence (e.g., a CDR-H3 sequence) having at least about 90% sequence identity to SEQ ID NO:29, SEQ ID NO:30, SEQ ID NO:31, SEQ ID NO:32, SEQ ID NO:33, SEQ ID NO:34, SEQ ID NO:36, SEQ ID NO:37, SEQ ID NO:38, SEQ ID NO:39, SEQ ID NO:43, SEQ ID NO:44, SEQ ID NO:45, SEQ ID NO:46 or SEQ ID NO:47.

In certain embodiments, the antibody or fragment thereof comprises an amino acid sequence (e.g., a CDR-H3 sequence) having at least about 95% sequence identity to SEQ ID NO:29, SEQ ID NO:30, SEQ ID NO:31, SEQ ID NO:32, SEQ ID NO:33, SEQ ID NO:34, SEQ ID NO:36, SEQ ID NO:37, SEQ ID NO:38, SEQ ID NO:39, SEQ ID NO:43, SEQ ID NO:44, SEQ ID NO:45, SEQ ID NO:46 or SEQ ID NO:47.

In certain embodiments, the antibody or fragment thereof comprises an amino acid sequence (e.g., a CDR-H3 sequence) selected from the group consisting of SEQ ID NO:29, SEQ ID NO:30, SEQ ID NO:31, SEQ ID NO:32, SEQ ID NO:33, SEQ ID NO:34, SEQ ID NO:36, SEQ ID NO:37, SEQ ID NO:38, SEQ ID NO:39, SEQ ID NO:43, SEQ ID NO:44, SEQ ID NO:45, SEQ ID NO:46 or SEQ ID NO:47.

In certain embodiments, the antibody or fragment thereof comprises an amino acid sequence (e.g., a CDR-H3 sequence) comprising SEQ ID NO:30, SEQ ID NO:32, SEQ ID NO:34, SEQ ID NO:37, SEQ ID NO:38 or SEQ ID NO:47. In certain embodiments, the antibody or fragment thereof comprises an amino acid sequence (e.g., a CDR-H3 sequence) comprising: SEQ ID NO:30, SEQ ID NO:32 or SEQ ID NO:38. In certain embodiments, the antibody or fragment thereof comprises an amino acid sequence (e.g., a CDR-H3 sequence) comprising SEQ ID NO:32.

In certain embodiments, the antibody or fragment thereof comprises a CDR-H3 sequence consisting of SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47 or SEQ ID NO:48.

In certain embodiments, the antibody or fragment thereof comprises a CDR-H3 sequence consisting of SEQ ID NO:29, SEQ ID NO:30, SEQ ID NO:31, SEQ ID NO:32, SEQ ID NO:33, SEQ ID NO:34, SEQ ID NO:36, SEQ ID NO:37, SEQ ID NO:38, SEQ ID NO:39, SEQ ID NO:42, SEQ ID NO:43, SEQ ID NO:44, SEQ ID NO:45, SEQ ID NO:46, SEQ ID NO:47 or SEQ ID NO:48.

In certain embodiments, the antibody or fragment thereof comprises a CDR-H3 sequence consisting of SEQ ID NO:29, SEQ ID NO:30, SEQ ID NO:31, SEQ ID NO:32, SEQ ID NO:33, SEQ ID NO:34, SEQ ID NO:36, SEQ ID NO:37, SEQ ID NO:38, SEQ ID NO:39, SEQ ID NO:43, SEQ ID NO:44, SEQ ID NO:45, SEQ ID NO:46 or SEQ ID NO:47.

In certain embodiments, the antibody or fragment thereof comprises a CDR-H3 sequence consisting of SEQ ID NO:30, SEQ ID NO:32, SEQ ID NO:34, SEQ ID NO:37, SEQ ID NO:38 or SEQ ID NO:47. In certain embodiments, the antibody or fragment thereof comprises a CDR-H3 sequence consisting of SEQ ID NO:30, SEQ ID NO:32 or SEQ ID NO:38. In certain embodiments, the antibody or fragment thereof comprises a CDR-H3 sequence consisting of SEQ ID NO:32.

Certain embodiments of the invention provide an antibody, or fragment thereof, comprising an amino acid sequence having at least 80%, 85%, 90%, 95%, 99% or 100% sequence identity to VKLQKDKSHQWIRNL-VATPYGRYVMDY (SEQ ID NO:8). In certain embodiments, the antibody or fragment thereof comprises SEQ ID NO:8. In certain embodiments, an antibody fragment consists of SEQ ID NO:8. In certain embodiments, the antibody, or fragment thereof, is an inhibitor of matrix metalloproteinase (MMP)-14.

Certain embodiments of the invention provide an antibody, or fragment thereof, comprising an amino acid sequence having at least about 80%, 85%, 90%, 95%, 99% or 100% sequence identity to SCVWACCACRYWSGSD-SHYAMDY (SEQ ID NO:32). In certain embodiments, the antibody or fragment thereof comprises SEQ ID NO:32. In certain embodiments, an antibody fragment consists of SEQ ID NO:32. In certain embodiments, the antibody, or fragment thereof, is an inhibitor of matrix metalloproteinase (MMP)-14.

Certain embodiments of the invention provide an antibody, or a fragment thereof, comprising a heavy chain variable region ($V_H$) comprising a sequence having at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a sequence described herein (e.g., a $V_H$ sequence described herein).

Certain embodiments of the invention provide an antibody, or a fragment thereof, comprising a heavy chain variable region ($V_H$) comprising a sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a sequence selected from the group consisting of: SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119 and SEQ ID NO:121.

Certain embodiments of the invention provide an antibody, or a fragment thereof, comprising a heavy chain variable region ($V_H$) comprising a sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a sequence selected from the group consisting of: SEQ ID NO:49, SEQ ID NO:51, SEQ ID NO:53, SEQ ID NO:55, SEQ ID NO:57, SEQ ID NO:59, SEQ ID NO:63, SEQ ID NO:67, SEQ ID NO:69, SEQ ID NO:71, SEQ ID NO:73, SEQ ID NO:75, SEQ ID NO:77, SEQ ID NO:81, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:111, SEQ ID NO:113, SEQ ID NO:115, SEQ ID NO:117 and SEQ ID NO:119.

In certain embodiments, the $V_H$ comprises a sequence having at least about 90% sequence identity to a sequence selected from the group consisting of: SEQ ID NO:49, SEQ ID NO:51, SEQ ID NO:53, SEQ ID NO:55, SEQ ID NO:57, SEQ ID NO:59, SEQ ID NO:63, SEQ ID NO:67, SEQ ID NO:69, SEQ ID NO:71, SEQ ID NO:73, SEQ ID NO:75, SEQ ID NO:77, SEQ ID NO:81, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:111, SEQ ID NO:113, SEQ ID NO:115, SEQ ID NO:117 and SEQ ID NO:119.

In certain embodiments, the $V_H$ comprises a sequence having at least about 95% sequence identity to a sequence selected from the group consisting of: SEQ ID NO:49, SEQ ID NO:51, SEQ ID NO:53, SEQ ID NO:55, SEQ ID NO:57, SEQ ID NO:59, SEQ ID NO:63, SEQ ID NO:67, SEQ ID NO:69, SEQ ID NO:71, SEQ ID NO:73, SEQ ID NO:75, SEQ ID NO:77, SEQ ID NO:81, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:111, SEQ ID NO:113, SEQ ID NO:115, SEQ ID NO:117 and SEQ ID NO:119.

In certain embodiments, the $V_H$ comprises a sequence selected from the group consisting of: SEQ ID NO:49, SEQ ID NO:51, SEQ ID NO:53, SEQ ID NO:55, SEQ ID NO:57, SEQ ID NO:59, SEQ ID NO:63, SEQ ID NO:67, SEQ ID NO:69, SEQ ID NO:71, SEQ ID NO:73, SEQ ID NO:75, SEQ ID NO:77, SEQ ID NO:81, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:111, SEQ ID NO:113, SEQ ID NO:115, SEQ ID NO:117 and SEQ ID NO:119.

In certain embodiments, the $V_H$ comprises a sequence selected from the group consisting of: SEQ ID NO:49, SEQ ID NO:51, SEQ ID NO:53, SEQ ID NO:55, SEQ ID NO:57, SEQ ID NO:59, SEQ ID NO:63, SEQ ID NO:67, SEQ ID NO:69, SEQ ID NO:71, SEQ ID NO:73, SEQ ID NO:75, SEQ ID NO:77 and SEQ ID NO:81.

In certain embodiments, the $V_H$ comprises SEQ ID NO:49, SEQ ID NO:51, SEQ ID NO:57 or SEQ ID NO:59.

In certain embodiments, the $V_H$ comprises SEQ ID NO:49.

In certain embodiments, the $V_H$ comprises a sequence selected from the group consisting of: SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:111, SEQ ID NO:113, SEQ ID NO:115, SEQ ID NO:117 and SEQ ID NO:119.

In certain embodiments, the $V_H$ comprises SEQ ID NO:91, SEQ ID NO:95, SEQ ID NO:99, SEQ ID NO:103, SEQ ID NO:105 or SEQ ID NO:119.

In certain embodiments, the $V_H$ comprises SEQ ID NO:91, SEQ ID NO:95, or SEQ ID NO:105.

In certain embodiments, the $V_H$ comprises SEQ ID NO:95.

In certain embodiments, the $V_H$ consists of a sequence selected from the group consisting of: SEQ ID NO:49, SEQ ID NO:51, SEQ ID NO:53, SEQ ID NO:55, SEQ ID NO:57, SEQ ID NO:59, SEQ ID NO:63, SEQ ID NO:67, SEQ ID NO:69, SEQ ID NO:71, SEQ ID NO:73, SEQ ID NO:75, SEQ ID NO:77 and SEQ ID NO:81.

In certain embodiments, the $V_H$ consists of a sequence selected from the group consisting of: SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:111, SEQ ID NO:113, SEQ ID NO:115, SEQ ID NO:117 and SEQ ID NO:119.

In certain embodiments, the antibody, or a fragment thereof, comprises a light chain variable region ($V_L$) comprising a sequence having at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a sequence described herein (e.g., a $V_L$ sequence described herein).

In certain embodiments, the antibody, or a fragment thereof, further comprises a light chain variable region ($V_L$) comprising a sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a sequence selected from the group consisting of: SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120 and SEQ ID NO:122.

In certain embodiments, the antibody, or a fragment thereof, further comprises a light chain variable region ($V_L$) comprising a sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a sequence selected from the group consisting of: SEQ ID NO:50, SEQ ID NO:52, SEQ ID NO:54, SEQ ID NO:56, SEQ ID NO:58, SEQ ID NO:60, SEQ ID NO:64, SEQ ID NO:68, SEQ ID NO:70, SEQ ID NO:72, SEQ ID NO:74, SEQ ID NO:76, SEQ ID NO:78, SEQ ID NO:82, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:112, SEQ ID NO:114, SEQ ID NO:116, SEQ ID NO:118 and SEQ ID NO:120.

In certain embodiments, the $V_L$ comprises a sequence having at least about 90% sequence identity to a sequence selected from the group consisting of: SEQ ID NO:50, SEQ ID NO:52, SEQ ID NO:54, SEQ ID NO:56, SEQ ID NO:58, SEQ ID NO:60, SEQ ID NO:64, SEQ ID NO:68, SEQ ID NO:70, SEQ ID NO:72, SEQ ID NO:74, SEQ ID NO:76, SEQ ID NO:78, SEQ ID NO:82, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:112, SEQ ID NO:114, SEQ ID NO:116, SEQ ID NO:118 and SEQ ID NO:120.

In certain embodiments, the $V_L$ comprises a sequence having at least about 95% sequence identity to a sequence selected from the group consisting of: SEQ ID NO:50, SEQ ID NO:52, SEQ ID NO:54, SEQ ID NO:56, SEQ ID NO:58, SEQ ID NO:60, SEQ ID NO:64, SEQ ID NO:68, SEQ ID NO:70, SEQ ID NO:72, SEQ ID NO:74, SEQ ID NO:76, SEQ ID NO:78, SEQ ID NO:82, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:112, SEQ ID NO:114, SEQ ID NO:116, SEQ ID NO:118 and SEQ ID NO:120.

In certain embodiments, the $V_L$ comprises a sequence selected from the group consisting of: SEQ ID NO:50, SEQ ID NO:52, SEQ ID NO:54, SEQ ID NO:56, SEQ ID NO:58, SEQ ID NO:60, SEQ ID NO:64, SEQ ID NO:68, SEQ ID NO:70, SEQ ID NO:72, SEQ ID NO:74, SEQ ID NO:76, SEQ ID NO:78, SEQ ID NO:82, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:112, SEQ ID NO:114, SEQ ID NO:116, SEQ ID NO:118 and SEQ ID NO:120.

In certain embodiments, the $V_L$ comprises a sequence selected from the group consisting of: SEQ ID NO:50, SEQ ID NO:52, SEQ ID NO:54, SEQ ID NO:56, SEQ ID NO:58, SEQ ID NO:60, SEQ ID NO:64, SEQ ID NO:68, SEQ ID NO:70, SEQ ID NO:72, SEQ ID NO:74, SEQ ID NO:76, SEQ ID NO:78 and SEQ ID NO:82.

In certain embodiments, the $V_L$ comprises SEQ ID NO:50, SEQ ID NO:52, SEQ ID NO:58 or SEQ ID NO:60.

In certain embodiments, the $V_L$ comprises SEQ ID NO:50.

In certain embodiments, the $V_L$ comprises a sequence selected from the group consisting of: SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:112, SEQ ID NO:114, SEQ ID NO:116, SEQ ID NO:118 and SEQ ID NO:120.

In certain embodiments, the $V_L$ comprises SEQ ID NO:92, SEQ ID NO:96, SEQ ID NO:100, SEQ ID NO:104, SEQ ID NO:106 or SEQ ID NO:120.

In certain embodiments, the $V_L$ comprises SEQ ID NO:92, SEQ ID NO:96, or SEQ ID NO:106.

In certain embodiments, the $V_L$ comprises SEQ ID NO:96.

In certain embodiments, the $V_L$ consists of a sequence selected from the group consisting of: SEQ ID NO:50, SEQ ID NO:52, SEQ ID NO:54, SEQ ID NO:56, SEQ ID NO:58, SEQ ID NO:60, SEQ ID NO:64, SEQ ID NO:68, SEQ ID NO:70, SEQ ID NO:72, SEQ ID NO:74, SEQ ID NO:76, SEQ ID NO:78 and SEQ ID NO:82.

In certain embodiments, the $V_L$ consists of a sequence selected from the group consisting of: SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:112, SEQ ID NO:114, SEQ ID NO:116, SEQ ID NO:118 and SEQ ID NO:120.

In certain embodiments, the $V_L$ is linked (e.g., through a linker or a direct bond, such as a peptide bond) to a light chain constant region. In certain embodiments, the $V_H$ is linked to at least one heavy chain constant region (e.g., 1, 2, or 3). In certain embodiments, the heavy and light chains are linked via one or more disulfide bonds.

In certain embodiments, the antibody or fragment thereof is a recombinant antibody or fragment thereof. In certain embodiments, the antibody or fragment thereof is a chimeric antibody or fragment thereof. In certain embodiments, the antibody or fragment thereof is humanized.

In certain embodiments, an antibody of the invention is a monoclonal antibody or a fragment thereof.

In certain embodiments, antibody, or fragment thereof, is a fragment. In certain embodiments, the fragment comprises an antigen-binding domain or a variable region. For example, in certain embodiments, the fragment is a Fab, F(ab')$_2$, Fv, single-chain Fv (scFv), CDR (e.g., CDR-H3), diabody (diabodies), linear antibody or a multispecific antibody prepared from an antibody fragment. In certain embodiments, the fragment is a Fragment antigen-binding (Fab) fragment (e.g., a Fab comprising a human antibody scaffold). In other embodiments, the fragment is a CDR-H3.

Thus, in certain embodiments, the fragment consists of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47 or SEQ ID NO:48.

In certain embodiments, the fragment consists of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 or SEQ ID NO:27.

In certain embodiments, the fragment consists of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or SEQ ID NO:21.

In certain embodiments, the fragment consists of SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47 or SEQ ID NO:48.

In certain embodiments, the fragment consists of SEQ ID NO:29, SEQ ID NO:30, SEQ ID NO:31, SEQ ID NO:32, SEQ ID NO:33, SEQ ID NO:34, SEQ ID NO:36, SEQ ID NO:37, SEQ ID NO:38, SEQ ID NO:39, SEQ ID NO:42, SEQ ID NO:43, SEQ ID NO:44, SEQ ID NO:45, SEQ ID NO:46, SEQ ID NO:47 or SEQ ID NO:48.

In certain embodiments, the fragment consists of SEQ ID NO:29, SEQ ID NO:30, SEQ ID NO:31, SEQ ID NO:32, SEQ ID NO:33, SEQ ID NO:34, SEQ ID NO:36, SEQ ID NO:37, SEQ ID NO:38, SEQ ID NO:39, SEQ ID NO:43, SEQ ID NO:44, SEQ ID NO:45, SEQ ID NO:46 or SEQ ID NO:47.

In certain embodiments, the fragment consists of SEQ ID NO:30, SEQ ID NO:32, SEQ ID NO:34, SEQ ID NO:37, SEQ ID NO:38 or SEQ ID NO:47. In certain embodiments, the fragment consists of SEQ ID NO:30, SEQ ID NO:32 or SEQ ID NO:38. In certain embodiments, the fragment consists of SEQ ID NO:32.

Certain embodiments of the invention provide an antibody or fragment thereof as described herein.

Certain embodiments of the invention provide a method as described herein for making an antibody of the invention or fragment thereof.

Certain embodiments of the invention provide an antibody or fragment thereof made by a method as described herein.

Certain embodiments of the invention provide a composition comprising an antibody or fragment thereof and physiologically-acceptable, non-toxic carrier. In certain embodiments, the composition is a pharmaceutical composition and the carrier is a pharmaceutically acceptable carrier.

As used herein, the term "antibody" includes a single-chain variable fragment (scFv or "nanobody"), humanized, fully human or chimeric antibodies, single-chain antibodies, diabodies, and antigen-binding fragments of antibodies that do not contain the Fc region (e.g., Fab fragments). In certain embodiments, the antibody is a human antibody or a humanized antibody. A "humanized" antibody contains only the three CDRs (complementarity determining regions) and sometimes a few carefully selected "framework" residues (the non-CDR portions of the variable regions) from each donor antibody variable region recombinantly linked onto the corresponding frameworks and constant regions of a human antibody sequence. A "fully humanized antibody" is created in a hybridoma from mice genetically engineered to have only human-derived antibody genes or by selection from a phage-display library of human-derived antibody genes.

A scFv is a fusion protein of the variable region of the heavy ($V_H$) and light chains ($V_L$) of an immunoglobulin that is connected by means of a linker peptide. The linker is usually short, about 10-25 amino acids in length. If flexibility is important, the linker will contain a significant number of glycines. If solubility is important, serines or theonines will be utilized in the linker. The linker may link the amino-terminus of the $V_H$ to the carboxy-terminus of the $V_L$, or the linker may link the carboxy-terminus of the $V_H$ to the amino-terminus of the $V_L$. Divalent (also called bivalent) scFvs can be generated by linking two scFvs. For example, a divalent scFv can be made by generating a single peptide containing two $V_H$ and two $V_L$ regions. Alternatively, two peptides, each containing a single $V_H$ and a single $V_L$ region can be dimerized (also called "diabodies"). Holliger et al., "Diabodies: small bivalent and bispecific antibody fragments," PNAS, July 1993, 90:6444-6448. Bivalency allows antibodies to bind to multimeric antigens with high avidity, and bispecificity allows the cross-linking of two antigens.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are typically produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention may comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more specifically at least 75%, even more specifically at least 80%, still more specifically at least 85%, yet more specifically at least 90%, and most specifically at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov).

Polyclonal and monoclonal antibodies can be prepared by methods known to those skilled in the art.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al. (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

The antibodies of the present invention also include antibodies which comprise complementarity-determining regions (CDRs), or regions functionally equivalent to CDRs. The term "functionally equivalent" refers to comprising amino acid sequences similar to the amino acid sequences of CDRs of any of the monoclonal antibodies isolated in the Examples. The term "CDR" refers to a region in an antibody variable region (also called "V region"), and determines the specificity of antigen binding. The H chain and L chain each have three CDRs, designated from the N terminus as CDR1, CDR2, and CDR3. There are four regions flanking these CDRs: these regions are referred to as "framework," and their amino acid sequences are highly conserved. The CDRs can be transplanted into other antibodies, and thus a recombinant antibody can be prepared by combining CDRs with the framework of a desired antibody. One or more amino acids of a CDR can be modified without losing the ability to bind to its antigen. For example, one or more amino acids in a CDR can be substituted, deleted, and/or added.

In certain embodiments, an amino acid residue is mutated into one that allows the properties of the amino acid sidechain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). The letters within parenthesis indicate the one-letter amino acid codes. Amino acid substitutions within each group are called conservative substitutions. It is well known that a polypeptide comprising a modified amino acid sequence in which one or more amino acid residues is deleted, added, and/or substituted can retain the original biological activity (Mark D. F. et al., Proc. Natl. Acad. Sci. U.S.A. 81:5662-5666 (1984); Zoller M. J. and Smith M., Nucleic Acids Res. 10: 6487-6500 (1982); Wang A. et al., Science 224: 1431-1433; Dalbadie-McFarland G. et al., Proc. Natl. Acad. Sci. U.S.A. 79: 6409-6413 (1982)). The number of mutated amino acids is not limited, but in general, the number falls within 40% of amino acids of each CDR, and specifically within 35%, and still more specifically within 30% (e.g., within 25%). The identity of amino acid sequences can be determined as described herein.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, may be obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., Nature 321: 522-525 (1986); Reichmann et al., Nature 332: 323-329 (1988); Presta Curr. Op. Struct. Biol. 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., Cancer Res. (1993) 53, 851-856).

As described herein, an antibody of the invention or a fragment thereof may comprise a synthetic CDR-H3. Additionally, an antibody of the invention may also be a recombinant antibody (e.g., a humanized or chimeric antibody) or a fragment thereof. Accordingly, such an antibody of the invention or fragment thereof would not be a product of nature. Additionally, an antibody of the invention or a fragment thereof may comprise markedly different characteristics (e.g., structural, functional and/or other properties) as compared to naturally occurring antibody with a long CDR3.

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')$_2$, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., Journal of Biochemical and Biophysical Methods 24:107-117 (1992); Brennan et al., Science 229:81 (1985); Co, M. S. et al., J. Immunol., 1994, 152, 2968-2976; Better, M. & Horwitz, A. H., Methods in Enzymology, 1989, 178, 476-496, Academic Press, Inc.; Plueckthun, A. & Skerra, A., Methods in Enzymology, 1989, 178, 476-496, Academic Press, Inc.; Lamoyi, E., Methods in Enzymology, 1989, 121, 663-669; Bird, R. E. et al., TIBTECH, 1991, 9, 132-137).

An "Fv" fragment is the smallest antibody fragment, and contains a complete antigen recognition site and a binding site. This region is a dimer ($V_H$-$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a specific antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of $F(ab')_2$. Other chemically crosslinked antibody fragments are also known to those skilled in the art. Pepsin digestion of an antibody yields two fragments; one is a $F(ab')_2$ fragment which comprises two antigen-binding domains and can cross-react with antigens, and the other is the remaining fragment (referred to as pFc'). Herein, an antibody fragment equivalent to that obtained by pepsin digestion is referred to as a "$F(ab')_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab')$_2$-SH fragments can be recovered directly from hosts, such as E. coli, and then allowed to form $F(ab')_2$ fragments by chemical crosslinking (Carter et al., Bio/Technology 10:163-167 (1992)). In an alternative method, $F(ab')_2$ fragments can be isolated directly from a culture of recombinant hosts.

The term "diabody (Db)" refers to a bivalent antibody fragment constructed by gene fusion (for example, P. Holliger et al., Proc. Natl. Acad. Sci. USA 90: 6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, such as a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A.), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., J. Biomed. Mater. Res. 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP: 133,988).

Nucleic Acids, Expression Cassettes, Vectors and Cells

Certain embodiments of the invention provide a nucleic acid encoding an antibody or fragment thereof as described herein. In certain embodiments, the nucleic acid further comprises a promoter.

Certain embodiments of the invention provide an expression cassette comprising a nucleic acid as described herein and a promoter.

Certain embodiments of the invention provide a vector (e.g., a phagemid) comprising an expression cassette as described herein.

Certain embodiments of the invention provide a cell comprising a vector as described herein.

Certain embodiments of the invention provide a phage particle comprising a vector as described herein.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucl. Acids Res., 19:508 (1991); Ohtsuka et al., JBC, 260:2605 (1985); Rossolini et al., Mol. Cell. Probes, 8:91 (1994). A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

By "portion" or "fragment," as it relates to a nucleic acid molecule, sequence or segment of the invention, when it is linked to other sequences for expression, is meant a sequence having at least 80 nucleotides, more specifically at least 150 nucleotides, and still more specifically at least 400 nucleotides. If not employed for expressing, a "portion" or "fragment" means at least 9, specifically 12, more specifically 15, even more specifically at least 20, consecutive nucleotides, e.g., probes and primers (oligonucleotides), corresponding to the nucleotide sequence of the nucleic acid molecules of the invention.

The terms "protein," "peptide" and "polypeptide" are used interchangeably herein.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, culture medium may represent less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, *Molecular Cloning: A Laboratory Manual*, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

"Genome" refers to the complete genetic material of an organism.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., *Mol. Biotech.*, 3:225 (1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

The following terms are used to describe the sequence relationships between two or more sequences (e.g., nucleic acids, polynucleotides or polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA, gene sequence or peptide sequence, or the complete cDNA, gene sequence or peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller, CABIOS, 4:11 (1988); the local homology algorithm of Smith et al., Adv. Appl. Math., 2:482 (1981); the homology alignment algorithm of Needleman and Wunsch, J M B, 48:443 (1970); the search-for-similarity-method of Pearson and Lipman, Proc. Natl. Acad. Sci. USA, 85:2444 (1988); the algorithm of Karlin and Altschul, Proc. Natl. Acad. Sci. USA, 87:2264 (1990), modified as in Karlin and Altschul, Proc. Natl. Acad. Sci. USA, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988); Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994). The ALIGN program is based on the algorithm of Myers and Miller, supra. The BLAST programs of Altschul et al., JMB, 215: 403 (1990); Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more specifically less than about 0.01, and most specifically less than about 0.001.

To obtain gapped alignments for comparison purposes, Gapped BLAST (in BLAST 2.0) can be utilized as described in Altschul et al., Nucleic Acids Res. 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of sequences for determination of percent sequence identity to another sequence may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH.

However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology Hybridization with Nucleic Acid Probes, part I chapter 2 "Overview of principles of hybridization and the strategy of nucleic acid probe assays" Elsevier, New York (1993). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more specifically about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_{max}$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82:488 (1985); Kunkel et al., Meth. Enzymol., 154:367 (1987); U.S. Pat. No. 4,873,192; Walker and Gaastra, Techniques in Mol. Biol. (MacMillan Publishing Co. (1983), and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art and are disclosed in Sambrook and Russell, supra. See also Innis et al., PCR Protocols, Academic Press (1995); and Gelfand, PCR Strategies, Academic Press (1995); and Innis and Gelfand, PCR Methods Manual, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

Methods of Use

Certain embodiments of the invention provide a method of inhibiting the enzymatic activity (e.g., inhibits protease cleavage activity) of matrix metalloproteinase (MMP)-14, comprising contacting MMP-14 with an antibody of the invention or a fragment thereof. In certain embodiments, MPP-14 collagenolysis is inhibited and/or activation of MMP-2 proenzyme is inhibited. Methods for measuring the enzymatic activity of MMP-14, collagenolysis and/or activation of MMP-2 proenzyme are known in the art. For example, in certain embodiments, an assay described herein may be used. In certain embodiments, an antibody of the invention or a fragment thereof inhibits the enzymatic activity of MMP-14, collagenolysis and/or activation of MMP-2 proenzyme by at least about 5%, at least about 10%, at least about 20%, at least about 30%, at least about 40%, at least about 50%, at least about 60%, at least about 70%, at least about 80%, at least about 90%, at least about 95%, at least about 99% or at least about 100%.

In certain embodiments, MMP-14 is contacted with an antibody of the invention or a fragment thereof in vitro, in vivo or ex vivo.

Certain embodiments of the invention provide a method for treating cancer in a mammal (e.g., a mammal in need thereof), comprising administering an effective amount of an antibody of the invention or a fragment thereof to the mammal.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, and melanoma.

In certain embodiments, the cancer is melanoma metastasis. In certain embodiments, the cancer is pulmonary melanoma metastasis.

In certain embodiments, the cancer is breast carcinoma, a squamous cell carcinoma (SCC) of the head and neck or vulva, primary and metastatic melanoma, bladder carcinoma, colorectal tumor, intestinal tumorigenesis, or an endometrial, lung or prostate adenocarcinoma.

Certain embodiments of the invention provide a pharmaceutical composition for use in the treatment of cancer, comprising an antibody of the invention or a fragment thereof, and a pharmaceutically acceptable carrier.

Certain embodiments of the invention provide an antibody of the invention or a fragment thereof for use in medical therapy.

Certain embodiments of the invention provide an antibody of the invention or a fragment thereof for the prophylactic or therapeutic treatment of cancer.

Certain embodiments of the invention provide the use of an antibody of the invention or a fragment thereof to prepare a medicament for the treatment of cancer in a mammal (e.g., a mammal in need thereof).

Administration

For in vivo use, an antibody of the invention, or fragment thereof, is generally incorporated into a pharmaceutical composition prior to administration. Within such compositions, one or more antibodies of the invention may be present as active ingredient(s) (i.e., are present at levels sufficient to provide a statistically significant effect on the symptoms of a relevant disease (e.g., cancer), as measured using a representative assay). A pharmaceutical composition comprises one or more such antibodies in combination with any pharmaceutically acceptable carrier(s) known to those skilled in the art to be suitable for the particular mode of administration. In addition, other pharmaceutically active ingredients (including other therapeutic agents) may, but need not, be present within the composition.

The term "therapeutically effective amount," in reference to treating a disease state/condition, refers to an amount of an antibody or fragment thereof either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat" and "treatment" refer to both therapeutic treatment and prophylactic or preventative measures, wherein the object is to prevent or decrease an undesired physiological change or disorder, such as the development of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

In certain embodiments, the present antibodies (i.e., antibody of the present invention or a fragment thereof) may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the antibody may be combined with one or more excipients and used in the form of ingestible tablets, buccal tablets, troches, capsules, elixirs, suspensions, syrups, wafers, and the like. Such compositions and preparations should contain at least 0.1% of an antibody of the present invention. The percentage of the compositions and preparations may, of course, be varied and may conveniently be between about 2 to about 60% of the weight of a given unit dosage form. The amount of antibody in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the antibody, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the antibody may be incorporated into sustained-release preparations and devices.

The antibody may also be administered intravenously or intraperitoneally by infusion or injection. Solutions of the antibody may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the antibody that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be useful to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the antibody in the required amount in the appropriate solvent with various of the other ingredients enumerated above, as required, followed by filter sterilization. In the case of sterile powders for the preparation of sterile injectable solutions, the methods of preparation are vacuum drying and the freeze drying techniques, which yield a powder of the antibody plus any additional desired ingredient present in the previously sterile-filtered solutions.

For topical administration, the present antibodies may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present antibodies can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the antibodies of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the antibodies of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of an antibody of the present invention required for use in treatment will vary with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Antibodies of the invention can also be administered in combination with other therapeutic agents and/or treatments, such as other agents or treatments that are useful for the treatment of cancer. Examples of such agents include chemotherapeutic agents. Examples of such treatments include radiation. Additionally, one or more antibodies of the invention, or fragments thereof, may be administered (e.g., a combination of monoclonal antibodies, or fragments thereof, may be administered). Accordingly, one embodiment the invention also provides a composition comprising an antibody of the invention, or a fragment thereof, at least one other therapeutic agent, and a pharmaceutically acceptable diluent or carrier. The invention also provides a kit comprising an antibody of the invention, or a fragment thereof, at least one other therapeutic agent, packaging material, and instructions for administering the an antibody of the invention, or a fragment thereof, and the other therapeutic agent or agents to an animal to treat cancer.

As used herein, the term "therapeutic agent" refers to any agent or material that has a beneficial effect on the mammalian recipient.

Screening Libraries

The MMP family members are promising drug targets in diversified pathologies. Clinical trial failures have taught that selective, rather than broad-specificity, inhibitors are required for successful MMP therapies. Achieving target selectivity with small-molecule MMP inhibitors, however, is exceedingly difficult. Because the antigen-binding sites in conventional antibodies are predominantly incompatible with the concave reaction pockets of MMPs, design of inhibitory antibodies, an attractive alternative for selective inhibition, is also challenging. As discussed herein, a human antibody library was synthesized, which encodes extended convex antigen-binding sites, and a panel of inhibitory Fabs that selectively and efficiently inhibited MMP-14, a promising drug target in cancer, was isolated. This library, as well as similar libraries, can be used for the generation of inhibitory antibodies targeting multiple additional enzymes.

Accordingly, certain embodiments of the invention provide a synthetic library comprising a plurality of independently selected nucleic acid molecules, wherein each nucleic acid molecule encodes an antibody, or a fragment thereof, comprising a complementarity-determining region (CDR) between about 18 to about 50 amino acids in length, wherein the CDR forms a convex shaped paratope, and wherein one or more of the encoded antibodies, or fragments thereof, are capable of inhibiting an enzyme.

As used herein, the term "plurality of nucleic acid molecules" means at least 10 (e.g., 10, 100, 1,000, 10,000, 100,000, 1,000,000, 1,000,000,000, 5,000,000,000, 10,000,000,000, etc.) nucleic acid molecules. The nucleic acid molecules are independently selected, and as such, may be the same or may be different. In certain embodiments, at least about 25%, 30%, 35%, 40%, 45%, 50%, 55%, 60%, 65%, 70%, 75%, 80%, 85%, 90%, 95%, 99% or 100% of the nucleic acid molecules within the plurality are different from the other nucleic acid molecules within the plurality.

In certain embodiments, the CDR is between about 20 to about 40 amino acids in length. In certain embodiments, the CDR is between about 20 to about 30 amino acids in length. In certain embodiments, the CDR is between about 23 to about 27 amino acids in length. In certain embodiments, the CDR is 23 amino acids in length. In certain embodiments, the CDR is about 25 amino acids in length. In certain embodiments, the CDR is about 27 amino acids in length.

In certain embodiments, the CDR is a heavy chain CDR. In certain embodiments, the CDR is CDR-3. In certain embodiments, the CDR is a heavy chain CDR-3 (i.e., CDR-H3). In certain embodiments, each nucleic acid molecule independently comprises a sequence encoding a CDR-H3 amino acid sequence having at least 80% sequence identity to $(X)_n$Tyr(Z)MetAspTyr (SEQ ID NO:28), wherein each X is independently any amino acid; Z is alanine, glycine or valine; and n is about 13 to about 45. In certain embodiments, n is about 15 to about 25. In certain embodiments, n is 18. In certain embodiments, n is 20. In certain embodiments, n is 22. In certain embodiments, Z is alanine. In certain embodiments, Z is glycine. In certain embodiments, Z is valine. In certain embodiments, each nucleic acid molecule independently comprises a sequence encoding a CDR-H3 amino acid sequence having at least 85%, 86%, 87%, 88%, 89%, 90%, 91%, 92%, 93%, 94%, 95%, 96%, 97%, 98%, 99% or 100% sequence identity to SEQ ID NO:28.

In certain embodiments, each nucleic acid molecule encodes an antibody, or a fragment thereof, comprising a human antibody scaffold. In certain embodiments, each nucleic acid molecule encodes an antibody, or a fragment thereof, comprising a human antibody scaffold and a CDR-H3 as described herein (e.g., SEQ ID NO:28). In certain embodiments, each nucleic acid molecule encodes an antibody, or a fragment thereof, comprising a heavy chain variable domain from the $V_H3$ gene family. In certain embodiments, the nucleic acid encodes an antibody, or a fragment thereof, comprising a light chain variable domain from the kappa light chain gene family. In certain embodiments, each nucleic acid molecule encodes an antibody fragment. In certain embodiments, each nucleic acid encodes a Fab fragment. In certain embodiments, each nucleic acid molecule encodes a Fab fragment comprising human antibody scaffold and a CDR-H3 described herein (e.g., SEQ ID NO:28) (e.g., a CDR-H3 as described herein is inserted in frame into a F Fab library described by Persson et al. (2013) *J Mol Biol* 425(4):803-811).

In certain embodiments, each nucleic acid molecule is comprised within an expression cassette. In certain embodiments, each expression cassette is comprised within a vector (e.g., a phagemid). As described herein, a library of the invention may be a phage library. Accordingly, in certain embodiments of the invention a phage particle comprises a vector as described herein. In certain embodiments, each encoded antibody, or fragment thereof, is a fusion protein. For example, in certain embodiments, each encoded antibody, or fragment thereof, is fused to a phage coat protein, such as pIII, and may be expressed and displayed on a viral surface.

As described herein, one or more of the encoded antibodies, or fragments thereof, which are derived from the synthetic antibody library, are capable of inhibiting an enzyme. The term "inhibiting an enzyme" refers to inhibiting the function of an enzyme (e.g., inhibits its catalytic function). Assays for measuring the function of an enzyme are known in the art, for example, an assay as described in the Examples. In certain embodiments, the antibody, or fragment thereof, inhibits the biological activity of the enzyme by at least about 5%, at least about 10%, at least about 20%, at least about 30%, at least about 40%, at least about 50%, at least about 60%, at least about 70%, at least about 80%, or at least about 90%. In certain embodiments, the antibody or fragment thereof is a selective inhibitor.

In certain embodiments, the enzyme is a protease. In certain embodiments, the enzyme is a matrix metalloproteinase (MMP). MMPs are a family of zinc-dependent endopeptidases. In certain embodiments, the MMP is a human MMP. In certain embodiments, the MMP is MMP-1, MMP-2, MMP-3, MMP-7, MMP-8, MMP-9, MMP-10, MMP-11, MMP-12, MMP-13, MMP-14, MMP-15, MMP-16, MMP-17, MMP-19, MMP-20, MMP-21, MMP-23A, MMP-23B, MMP-24, MMP-25, MMP-26, MMP-27 or MMP-28. In certain embodiments, the MMP is MMP-14. In certain embodiments, the MMP is MMP-2. In certain embodiments, the MMP is MMP-9. In certain embodiments, the enzyme is matriptase. In certain embodiments, the enzyme is renin. In certain embodiments, the enzyme is ACE. In certain embodiments, the enzyme is an HIV protease. In certain embodiments, the enzyme is bacterial neuraminidase. In certain embodiments, the enzyme is lysozyme. In certain embodiments, the enzyme is carbonic anhydrase.

In certain embodiments, the enzyme is an enzyme other than MMP-14. In certain embodiments, the enzyme is an enzyme other than a metalloproteinase (e.g., from the ADAM, ADAMTS or MT-SP family). In certain embodiments, the enzyme is an enzyme other than a protease. In certain embodiments, the enzyme is an enzyme other than a HIV enzyme. In certain embodiments, the enzyme is an enzyme other than an influenza enzyme.

Screening Methods

Certain embodiments of the invention provide a method of isolating an antibody, or a fragment thereof, capable of binding a target enzyme comprising the steps of:
  a) panning a phage library (e.g., a Fab phage library) as described herein comprising contacting phage particles with (i) the target enzyme; or (2) a domain of the target enzyme (e.g., a catalytic domain), and incubating for a time sufficient to allow binding of phage particles to said target enzyme or domain of the target enzyme;
  b) removing phage particles not bound to the target enzyme or the domain of the target enzyme (e.g., through one or more washing steps); and
  c) eluting the bound phage particles from step (b), which produces an aliquot of phage particles.

In certain embodiments, the method further comprises serially performing steps (a)-(c) using the aliquot of phage particles produced from step (c). For example, in certain embodiments, the method further comprises subjecting the aliquot of phage particles to steps (a)-(c) one or more times.

In certain embodiments, the phage particles in step (a) are contacted with a domain of the target enzyme. In certain embodiments, the domain is a catalytic domain.

In certain embodiments, the elution in step (c) is an epitope specific elution (i.e., an epitope specific elution reagent may be used). For example, the elution reagent may bind only properly folded enzymes (e.g., may bind the catalytic domain of a properly folded enzyme) and not misfolded enzymes. Accordingly, only phage particles that bind a properly folded epitope of interest (e.g., the active site of a catalytic domain) in a target enzyme are eluted.

In certain embodiments, the method further comprises sequencing DNA from the eluted phage particles from step (c).

In certain embodiments, the method further comprises performing a monoclonal ELISA assay using the eluted phage particles from step (c).

In certain embodiments, the target enzyme is a protease. In certain embodiments, the target enzyme is a matrix metalloproteinase (MMP). In certain embodiments, the MMP is a human MMP. In certain embodiments, the MMP is a MMP-1, MMP-2, MMP-3, MMP-7, MMP-8, MMP-9, MMP-10, MMP-11, MMP-12, MMP-13, MMP-14, MMP-15, MMP-16, MMP-17, MMP-19, MMP-20, MMP-21, MMP-23A, MMP-23B, MMP-24, MMP-25, MMP-26, MMP-27 or MMP-28. In certain embodiments, the MMP is MMP-14. In certain embodiments, the MMP is MMP-2. In certain embodiments, the MMP is MMP-9. In certain embodiments, the target enzyme is matriptase. In certain embodiments, the target enzyme is renin. In certain embodiments, the target enzyme is ACE. In certain embodiments, the target enzyme is an HIV protease. In certain embodiments, the target enzyme is ACE. In certain embodiments, the target enzyme is bacterial neuraminidase. In certain embodiments, the target enzyme is lysozyme. In certain embodiments, the target enzyme is carbonic anhydrase.

In certain embodiments, the target enzyme is an enzyme other than MMP-14. In certain embodiments, the target enzyme is an enzyme other than a metalloproteinase (e.g., from the ADAM, ADAMTS or MT-SP family). In certain embodiments, the target enzyme is an enzyme other than a protease. In certain embodiments, the target enzyme is an enzyme other than a HIV enzyme. In certain embodiments, the target enzyme is an enzyme other than an influenza enzyme.

Certain embodiments of the invention provide an antibody, or fragment thereof, isolated by a method described herein.

The invention will now be illustrated by the following non-limiting Examples.

Example 1. Convex Paratope Synthetic Libraries as a Source of Selective Protease Inhibitory Antibodies Abstract Proteases are frequent pharmacological targets and their inhibitors are valuable drugs in multiple pathologies. The catalytic mechanism and the active site fold, however, are largely conserved among the protease classes, making the development of the selective inhibitors exceedingly challenging. In a departure from the conventional strategies, the structure of those camelid antibodies was reviewed, which are known to inhibit enzyme reactions. It was hypothesized that the inhibitory capacity of these camelid antibodies is linked to their CDRs encoding the unusually long, convex-shaped paratopes. A human Fab antibody library (over $1.25 \times 10^9$ individual variants) was then synthesized, which carried the extended, 23-27 residue, CDR-H3 segments. As a proof-of-principle, the catalytic domain of MMP-14, a pro-malignant protease and a drug target in cancer, was employed as bait. In these screens, 20 binders were identified, from which 14 performed as the potent and selective inhibitors of MMP-14 rather than as broad-specificity antagonists. Specifically, Fab 3A2 bound to MMP-14 at the active pocket vicinity with a high, 4.8 nM, affinity and was similarly efficient (9.7 nM) in inhibiting the protease cleavage activity. It is suggested that the unconventional antibody techniques described here could be readily generalized to facilitate the design of the antibody inhibitors to many additional enzymes.

Results

Antibody-based MMP inhibitors are emerging both as research tools and potential therapeutic agents (Botkjaer et al., (2016) *Oncotarget* 7(13):16773-16792; Devy et al. (2009) *Cancer Res* 69(4):1517-1526; Sela-Passwell et al. (2012) *Nat Med* 18(1):143-147; Naito et al. (2012) *Biochemistry* 51(44):8877-8884), because of: (i) high affinity and specificity due to the large antigen-antibody interaction area and multiple complementarity-determining regions (CDRs); (ii) long half-life and well-defined action mechanisms; (iii) low immunogenicity and toxicity; and (iv) a large number of MMPs potentially targetable by antibodies (Drag et al., (2010) *Nat Rev Drug Discov* 9(9):690-701).

Natural proteinase inhibitors exhibit a convex shaped conformation that inserts into the enzyme active site and blocks the substrate access and/or the catalytic function (De Genst, et al. (2006) *Proc Natl Acad Sci USA* 103(12):4586-4591; Fernandez-Catalan, et al. (1998) *EMBO J* 17(17):

5238-5248; Desmyter, et al. (1996) *Nat Struct Biol* 3(9): 803-811). However, if a conventional hybridoma technology is employed, there is a low chance of generating antibodies with the convex antigen-binding sites (paratopes). The catalytic pocket is often buried inside a major cleft or a concave enzyme structure and as such is normally inaccessible by the cave-like, grooved or flat antigen-binding surface in human and murine antibodies (Lauwereys, et al. (1998) *EMBO J* 17: 3512-3520). In contrast, the dromedary antibodies are enriched in the long CDRs encoding the extended convex-shaped paratopes and, intriguingly, a large proportion of antibodies isolated from camel and llama, as compared with human and murine antibodies, binds the active site pockets and inhibits enzymatic reactions (De Genst, et al. (2006) *Proc Natl Acad Sci USA* 103(12):4586-4591; Desmyter, et al. (1996) *Nat Struct Biol* 3(9):803-811; Lauwereys, et al. (1998) *EMBO J* 17: 3512-3520; Schmitz et al., (2013) *Structure* 21(7):1214-1224). However, the camelid antibodies would evoke an immune response in humans, and both camel and llama are not readily available in either academia or industry.

Because it was suspected that the convex paratopes are inhibitory, novel human antibody libraries were designed in which the long, convex-shaped camelid-like paratopes were incorporated into the human antibody scaffold (Hoogenboom H R. (2005) *Nat Biotechnol* 23(9):1105-1116) (FIG. 1). In this current proof-of-principle study, these libraries were screened for the inhibitors of MMP-14, a pro-invasive and pro-metastatic human proteinase (Genis et al. (2006) *Cancer Metastasis Rev* 25(1): 77-86; Morrison et al., (2009) *Curr Opin Cell Biol* 21(5): 645-653). As a result of these screens, a panel of the selective Fabs were isolated with high inhibitory potency against MMP-14. It is submitted that this and the similar libraries that exhibit the long, convex paratopes will be a valuable source of the inhibitory antibodies capable of targeting multiple additional enzymes, the active pockets of which are not readily accessible by the conventional human antibodies.

Design and Construction of Long CDR-H3 Synthetic Fab libraries.

Figure 6A:
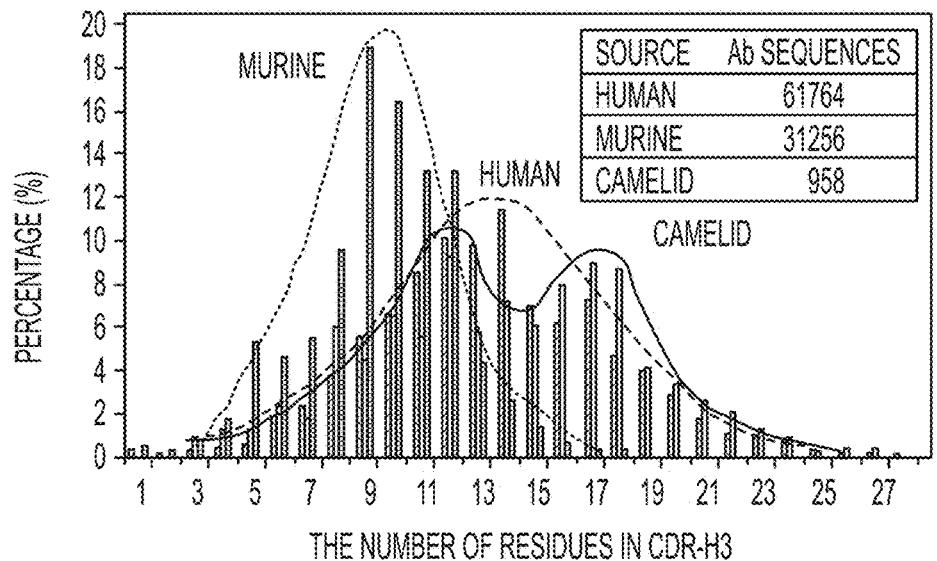
FIGS. 6A-B. Human, murine and camelid antibody repertoire analysis.

A large proportion of camelid heavy-chain antibodies ($V_H$Hs) exhibit enzyme-inhibiting functions. Structure studies suggest that inhibition is mediated by the extended $V_H$H CDR3s coding for the convex shaped paratopes that penetrate into the enzyme catalytic cleft (De Genst, et al. (2006) *Proc Natl Acad Sci USA* 103(12):4586-4591; Desmyter, et al. (1996) *Nat Struct Biol* 3(9):803-811; Lauwereys, et al. (1998) *EMBO J* 17: 3512-3520). The in-depth analysis of over 950 individual camelid antibodies from the IMGT, Kabat and abYsis databases determined that there is a bimodal distribution (with peaks at 12 and 19 residues) in their $V_H$H CDR3 length. A similar analysis of over 90,000 human and murine antibody sequences revealed that the length of their CDR-H3 is characterized by a single peak Gaussian distribution (12 and 9 residues, respectively) (FIG. 6A). In addition, the analysis suggests that relative to murine/human CDR-H3s, camelid $V_H$H CDR3 regions are enriched in cysteine, positively charged (Arg, Lys) and hydrophilic (Gly, Ser, Thr, Asn) residues while the level of hydrophobic residues (Phe, Val, Ile) is decreased. These amino acid preferences likely contribute to the additional disulfide bonds in camelid antibodies and, in general, to the integrity and improved solubility of the CDR3 loops (Nguyen et al., (2000) *EMBO J* 19(5):921-930; De Genst et al., (2006) *Dev Comp Immunol* 30(1-2): 187-198).

Figure 6B:
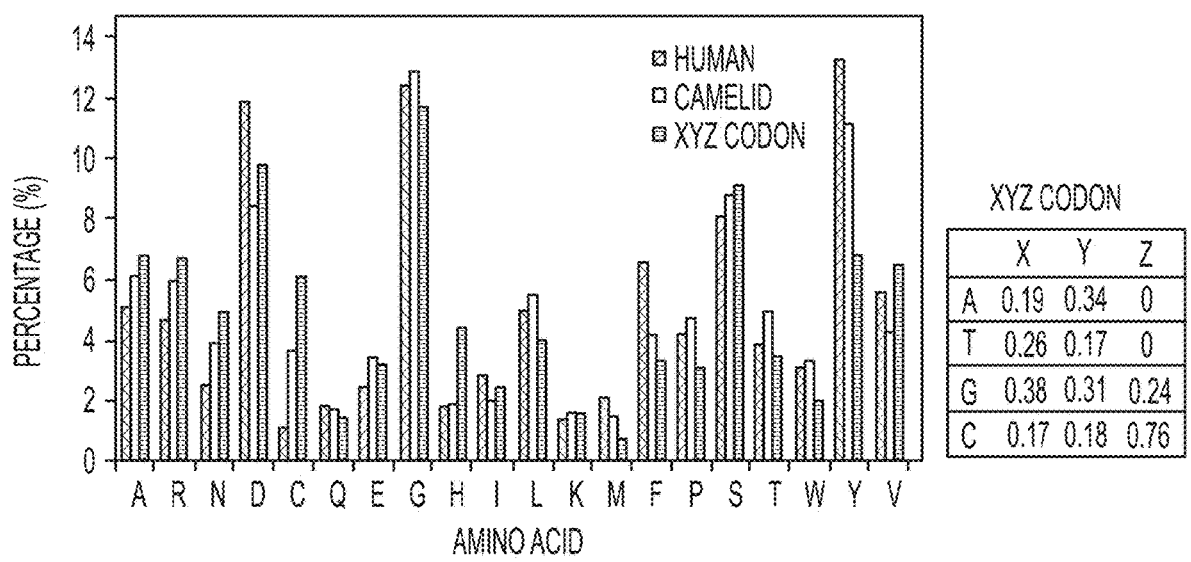
Figure 7:
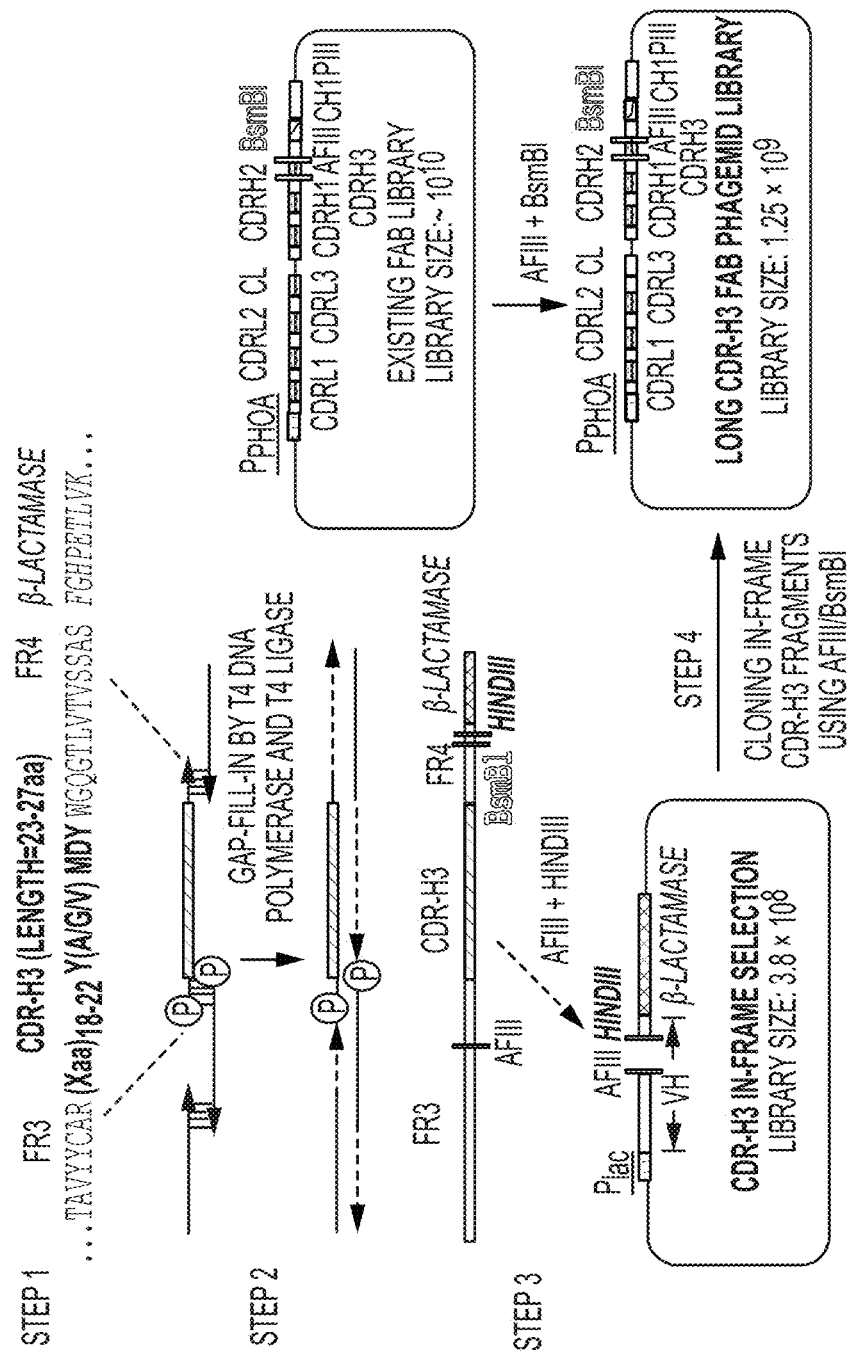
FIG. 7. Construction of synthetic antibody libraries with long CDR-H3s. (Step 1) Hybridization of degenerate oligonucleotides (Table 1) encoding long CDR-H3s with 23, 25 and 27 aa. (Step 2) CDR-H3 fragment assembly by T4 DNA polymerase and T4 DNA ligase. (Step 3) Assembled long CDR-H3 genes were subjected for full-length in-frame selection by fusing with β-lactamase. $3.8 \times 10^8$ CDR-H3s were generated after in-frame selection. (Step 4) Cloning the in-frame CDR-H3s into an existing Fab library to construct synthetic antibody library carrying long CDR-H3s with 23, 25 and 27 aa. The final library diversity was $1.25 \times 10^9$. Figure discloses SEQ ID NO: 126.

To mimic the amino acid usage in the camelid repertoire, a degenerate codon XYZ containing different proportions of the nucleotides at each of the three codon positions was custom-designed for its insertion into a human $V_H$ framework (FIG. 6B). Oligonucleotides encoding the 23, 25, and 27 residue long CDR-H3s were synthesized (Table 1 and FIG. 7, Step 1) and assembled using the mesophilic T4 DNA polymerase and T4 DNA ligase without amplification to achieve the high fidelity and low bias (FIG. 7, Step 2) (Ge et al., (2010) *Biotechnol Bioeng* 106(3):347-357).

TABLE 1

List of oligonucleotides for long CDR-H3 assembly

| Name | Oligonucleotide sequences |
|---|---|
| VH1* | ggccgtttcactataagcgcagacacatccaaaaac acagcctacctgcagatgaacagc (SEQ ID NO: 2) |
| VH2_23†, ‡ | P-ccgtgtattattgcgcgcgt(XYZ)$_{18}$(TAT) (GBN)atggactactggggtcaggg (SEQ ID NO: 3) |
| VH2_25†, ‡ | P-ccgtgtattattgcgcgcgt(NNS)$_{20}$(TAT) (GBN)atggactactggggtcaggg (SEQ ID NO: 4) |
| VH2_27†, ‡ | P-ccgtgtattattgcgcgcgt(NNS)$_{22}$(TAT) (GBN)atggactactggggtcaggg (SEQ ID NO: 5) |
| VH3*, ‡ | P-acgcgcgcaataatacacggcagtgtcctcagctct taagctgttcatctgcaggtaggc (SEQ ID NO: 6) |
| VH4* | tggatgaccgaagettgccgaggagacggtgaccagg gttccctgacccccagtagtccat (SEQ ID NO: 7) |

*Encoding for frame regions 3 and 4. Overlapping regions are underlined with annealing temperatures of -58° C.
†For CDR-H3s with 23, 25, 27 aa respectively. TAT encodes Tyr. GBN encodes Ala/Gly/Val. NNS contains equimolar quantities of two or four of the nucleotide bases and was used for CDR-H3s with 25 and 27 aa. XYZ codon contains different proportions of the nucleotides at each of the three codon positions to mimic compositions of camelid CDR-H3s (FIG. 6B), and was used for CDR-H3s with 23 aa.
‡VH2s and VH3 were 5' phosphorylated.

To remove the truncated and the reading-frame shifted fragments, the assembled CDR-H3 constructs were subjected to the full-length selection by their cloning into the N-terminal sequence of β-lactamase (FIG. 7, Step 3) (Seehaus et al., (1992) *Gene* 114(2):235-237). The diversity of the selected CDR-H3-23, -25, and -27 were 2.1, 0.85, and 0.80×10$^8$, respectively. DNA sequencing verified that 98% clones (129 from 131) were functional. Selected CDR-H3s were then incorporated into the synthetic Fab phage library (Persson, et al. (2013) *J Mol Biol* 425(4):803-811) to generate 1.25×10$^9$ Fab clones (4.6, 3.4, and 4.5×10$^8$ for CDR-H3-23, -25, and -27, respectively, FIG. 7, Step 4). Sequencing of the constructs indicated that 91% Fab clones (92 from 101) exhibited the full-length CDR-H3s with 23, 25 or 27 residues, and that the diversity in the other CDRs such as CDR-L3, -H1 and -H2 was still well preserved in the single VH/VL framework. In addition, 87% randomly picked clones (34 from 39) were able to produce detectable levels of the Fab-pill fusions suitable for phage panning.

Isolation of Anti-MMP-14 Inhibitory Antibodies. After three rounds of panning, the polyclonal phage ELISA suggested that anti-MMP-14 clones were significantly enriched in the isolated samples. The additional monoclonal ELISA of 288 randomly picked Fab phage clones identified 126 positive phage clones, from which 77 clones were sequenced resulting in the identification of the 20 unique clones with the long CDR-H3 regions (Table 2).

TABLE 2

Isolated Fabs from long CDR-H3 antibody library

| Rank* | Clone | CDRH3 sequence (Length)† | Repeats‡ | Affinity by ELISA (nM) | IC$_{50}$ by FRET§ Assay (nM) | Selectivity¶ over MMP-2/-9 |
|---|---|---|---|---|---|---|
| 1 | 3A2 | VKLQKDKSHQWIRNLVATPYGRYVMDY(27) (SEQ ID NO: 8) | 4 | 3.8 | 9.7 | Exclusive |
| 2 | 3E2 | GIKGLVFTGSQMKMLRRGNYNWYVMDY(27) (SEQ ID NO: 9) | 4 | 47 | 42 | Exclusive |
| 3 | 3D9 | RLMAYHGSCSSRLCQTAISPQRYAMDY(27) (SEQ ID NO: 10) | 1 | 6.4 | 61 | Exclusive |
| 4 | 2B5 | IGVNAWAVKMSQRMLATRGSGWYVMDY(27) (SEQ ID NO: 11) | 3 | 24 | 240 | Exclusive |
| 5 | 3G9 | ATNEKFRRKSLQVRLLMRSWLAYAMDY(27) (SEQ ID NO: 12) | 1 | 160 | 390 | 16.7 |
| 6 | 33D2 | SKYGPASRQLASRTSWSGPRGKYGMDY(27) (SEQ ID NO: 13) | 1 | 120 | 420 | 9.6 |
| 7 | 3F3 | LYNGWLMVEGIGSAREGPTWYAMDY(25) (SEQ ID NO: 14) | 3 | 34 | 970 | |
| 8 | 33F3 | GVRGNKLRLLSSRSGLMESHYVMDY(25) (SEQ ID NO: 15) | 4 | 1000 | 2300 | |
| 9 | 33D4 | SVHMKLSNKILSGWSWNNSFYAMDY(25) (SEQ ID NO: 16) | 1 | 460 | 3900 | |
| 10 | 32D1 | MSLHRNFNQQGRSRLLGRMPRTYGMDY(27) (SEQ ID NO: 17) | 4 | 350 | 4200 | |
| 11 | 3A6 | RPCKACRTRLELVRRGMDSGLRYGMDY(27) (SEQ ID NO: 18) | 2 | 980 | 4200 | |
| 12 | 33C4 | PTTSRVNKKLFRVSVLHPGSYGMDY(25) (SEQ ID NO: 19) | 1 | 220 | 4600 | |
| 13 | 3E9 | NGRYPGFLKRAHKRLLNFKAYVMDY(25) (SEQ ID NO: 20) | 22 | 51 | 6000 | |
| 14 | 32C2 | SQHAKKSTIIRMLEHQSRSGMQYVMDY(27) (SEQ ID NO: 21) | 1 | 150 | 8000 | |
| 15 | 32E10 | LDRDRYIHVGRAGNTYSNYYYVMDY(25) (SEQ ID NO: 22) | 1 | 9.7 | Non-inhibitory | |
| 16 | 32C11 | EIHMLSRQARYLRDGRRPRGSMYVMDY(27) (SEQ ID NO: 23) | 1 | 29 | Non-inhibitory | |
| 17 | 2H9 | GTSFQVRCVLYRLLSPGRYVMDY(23) (SEQ ID NO: 24) | 1 | 120 | Non-inhibitory | |
| 18 | 3B2 | STAATTLSRMSRSYWTIQLPYGMDY(25) (SEQ ID NO: 25) | 6 | 590 | Non-inhibitory | |
| 19 | 2E4 | SARLRLRGNHDRRRSKSVYYRPYVMDY(27) (SEQ ID NO: 26) | 2 | 840 | Non-inhibitory | |

TABLE 2 -continued

Isolated Fabs from long CDR-H3 antibody library

| Rank* | Clone | CDRH3 sequence (Length)† | Repeats‡ | Affinity by ELISA (nM) | $IC_{50}$ by FRET§ Assay (nM) | Selectivity¶ over MMP-2/-9 |
|---|---|---|---|---|---|---|
| 20 | 33F5 | NFRVESAGRPGKTVLRKDGKY AMDY(25) (SEQ ID NO: 27) | 1 | 1600 | Non-inhibitory | |

*Clones were ranked based on inhibition potency.
†Cysteine residues are underlined.
‡Based on sequencing results of 77 ELISA positive clones.
§14/20 (70%) of identified binding clones were inhibitory.
¶Only Fabs with an inhibition potency $IC_{50}$ <500 nM were measured. Exclusive selectivity indicated background ELISA signals for M MP-2/-9 up to 500 nM Fabs. Folds of selectivity were determined by the ratio of Fab concentrations, which gave the same ELISA signals, between MMP-2/-9 and MMP-14.

TABLE 3

Sequences for the light chain variable region (VL) and a heavy chain variable region (VH) from each clone shown in Table 2.

| Clone Name | VH or VL Chain | Sequence |
|---|---|---|
| 3A2 | VH | EVQLVESGGGLVQPGGSLRLSCAASGFNLSSSSMHWVRQAPGKGLEWVASIYP SYSYTYYADSVKGRFTISADTSKNTAYLQMNSLRAEDTAVYYCARVKLQKDKS HQWIRNLVATPYGRYVMDYWGQGTLVTVSSASTKGPSVFPLAPSSKSTSGGTA ALGCLVKDYFPEPVTVSWNSGALTSGVHTFPAVLQSSGLYSLSSVVTVPSSSLGT QTYICNVNHKPSNTKVDKKVEPKSCDKTHT (SEQ ID NO: 49) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQYGYPITFGQGTKVEIKRTVAA PSVFIFPPSDSQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 50) |
| 2B5 | VH | EVQLVESGGGLVQPGGSLRLSCAASGFNLSYSSMHWVRQAPGKGLEWVASIYP YSGYTYYADSVKGRFTISADTSKNTAYLQMNSLRAEDTAVYYCARIGVNAWA VKMSQRMLATRGSGWYVMDYWGQGTLVTVSSASTKGPSVFPLAPSSKSTSGG TAALGCLVKDYFPEPVTVSWNSGALTSGVHTFPAVLQSSGLYSLSSVVTVPSSSL GTQTYICNVNHKPSNTKVDKKVEPKSCDKTHT (SEQ ID NO: 51) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQSSSYPYSPITFGQGTKVEIKRT VAAPSVFIFPPSDSQLKSGTASVVCLLNNFYPREAKVQWKVDNALQSGNSQESV TEQDSKDSTYSLSSTLTLSKADYEKHKVYACEVTHQALSSPVTKSFNRGEC (SEQ ID NO: 52) |
| 3E9 | VH | EVQLVESGGGLVQPGGSLRLSCAASGFNLYYSSMHWVRQAPGKGLEWVASIYP SYGSTYYADSVKGRFTISADTSKNTAYLQMNSLRAEDTAVYYCARNGRYPGFL KRAHKRLLNFKAYVMDYWGQGTLVTVSSASTKGPSVFPLAPSSKSTSGGTAAL GCLVKDYFPEPVTVSWNSGALTSGVHTFPAVLQSSGLYSLSSVVTVPSSSLGTQT YICNVNHKPSNTKVDKKVEPKSCDKTHT (SEQ ID NO: 53) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQGSWYLITFGQGTKVEIKRTVA APSVFIFPPSDSQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 54) |
| 3F3 | VH | EVQLVESGGGLVQPGGSLRLSCAASGFNIYSSSMHWVRQAPGKGLEWVAYIYP YSGYTYYADSVKGRFTISADTSKNTAYLQMNSLRAEDTAVYYCARLYNGWLM VEGIGSAREGPTWYAMDYWGQGTLVTVSSASTKGPSVFPLAPSSKSTSGGTAAL GCLVKDYFPEPVTVSWNSGALTSGVHTFPAVLQSSGLYSLSSVVTVPSSSLGTQT YICNVNHKPSNTKVDKKVEPKSCDKTHT (SEQ ID NO: 55) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQGVYAAHPFTFGQGTKVEIK RTVAAPSVFIFPPSDSQLKSGTASVVCLLNNFYPREAKVQWKVDNALQSGNSQE SVTEQDSKDSTYSLSSTLTLSKADYEKHKVYACEVTHQGLSSPVTKSFNRGEC (SEQ ID NO: 56) |
| 3D9 | VH | EVQLVESGGGLVQPGGSLRLSCAASGFNIYSSSIHWVRQAPGKGLEWVASIYSS YGYTYYADSVKGRFTISADTSKNTAYLQMNSLRAEDTAVYYCARRLMAYHGS CSSRLCQTAISPQRYAMDYWGQGTLVTVSSASTKGPSVFPLAPSSKSTSGGTAA LGCLVKDYFPEPVTVSWNSSALTSGVHTFPAVLQSSGLYSLSSVVTVPSSSLGTQ TYICNVNHKPSNTKVDKKVEPKSCDKTHT (SEQ ID NO: 57) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQSSYSLITFGQGTKVEIKRTVA APSVFIFPPSDSQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 58) |

TABLE 3 -continued

Sequences for the light chain variable region (VL) and a heavy chain variable region (VH) from each clone shown in Table 2.

| Clone Name | VH or VL Chain | Sequence |
|---|---|---|
| 3E2 | VH | EVQLVESGGGLVQPGGSLRLSCAASGFNIYYYSIHWVRQAPGKGLEWVASIYPY SSYTYYADSVKGRFTISADTSKNTAYLQMNSLRAEDTAVYYCARGIKGLVFTGS QMKMLRRGNYNWYVMDYWGQGTLVTVSSASTKGPSVFPLAPSSKSTSGGTAA LGCLVKDYFPEPVTVSWNSGALTSGVHTFPAVLQSSGLYSLSSVVTVPSSSLGTQ TYICNVNHKPSNTKVDKKVEPKSCDKTHT (SEQ ID NO: 59) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQSSYSLITFGQGTKVEIKRTVA APSVFIFPPSDSQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 60) |
| 2H9 | VH | EVQLVESGGGLVQPGGSLRLSCAASGFNIYYSSMHWVRQAPGKGLEWVASIYP YSGYTYYADSVKGRFTISADTSKNTAYLQMNSLRAEDTAVYYCARGTSFQVRC VLYRLLSPGRYVMDYWGQGTLVTVSSASTKGP SVFPLAPSSKSTSGGTAALGCL VKDYFPEPVTVSWNSGALTSGVHTFPAVLQSSGLYSLSSVVTVP SSSLGTQTYIC NVNHKPSNTKVDKKVEPKSCDKTHT (SEQ ID NO: 61) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQSGYSYPFTFGQGTKVEIKRTV AAPSVFIFPPSDSQLKSGTASVVCLLNNFYPREAKVQWKVDNALQSGNSQESVT EQDSKDSTYSLSSTLTLSKADYEKHKVYACEVTHQGLSSPVTKSFNRGEC (SEQ ID NO: 62) |
| 3A6 | VH | EVQLVESGGGLVQPGGSLRLSCAASGFNISSYSIHWVRQAPGKGLEWVAYIYPS YGYTSYADSVKGRFTISADTSKNTAYLQMNSLRAEDTAVYYCARRPCKACRTR LELVRRGMDSGLRYGMDYWGQGTLVTVSSASTKGPSVFPLAPSSKSTSGGTAA LGCLVKDYFPEPVTVSWNSGALTSGVHTFPAVLQSSGLYSLSSVVTVPSSSLGTQ TYICNVNHKPSNTKVDKKVEPKSCDKTHT (SEQ ID NO: 63) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQAAYYLITFGQGTKVEIKRTVA APSVFIFPPSDSQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 64) |
| 2E4 | VH | EVQLVESGGGLVQPGGSLRLSCAASGFNLSYSYIHWVRQAPGKGLEWVAYISSS SGYTYYADSVKGRFTISADTSKNTAYLQMNSLRAEDTAVYYCARSARLRLRGN HDRRRSKSVYYRPYVMDYWGQGTLVTVSSASTKGPSVFPLAPSSKSTSGGTAA LGCLVKDYFPEPVTVSWNSGALTSGVHTFPAVLQSSGLYSLSSVVTVPSSSLGTQ TYICNVNHKPSNTKVDKKVEPKSCDKTHT (SEQ ID NO: 65) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQSSPSFPITFGQGTKVEIKRTVA APSVFIFPPSDSQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 66) |
| 33F3 | VH | EVQLVESGGGLVQPGGSLRLSCAASGFNISYSYMHWVRQAPGKGLEWVASISP YSGYTYYADSVKGRFTISAYTSKNTAYLQMNSLRAEDTAVYYCARGVRGNKL RLLSSRSGLMESHYVMDYWGQGTLVTVSSASTKGPSVFTLAPSSKSTSGGTAAL GCLVKDYFPEPVTVSWNSGALTSGVHTFPAVLQSSGLYSLSSVVTVPSSSLGTQT YICNVNHKPSNTKVDKKVEPKSCDKTHT (SEQ ID NO: 67) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQSSYSLIPITFGQGTKVEIKRTV AAPSVFIFPPSDSQLKSGTASVVCLLNNFYPREAKVQWKVDNALQSGNSQESVT EQDSKDSTYSLSSTLTLSKADYEKHKVYACEVTHQGLSSPVTKSFNRGEC (SEQ ID NO: 68) |
| 32D1 | VH | EVQLVESGGGLVQPGGSLRLSCAASGFNLYYSYMHWVRQAPGKGLEWVASISP YSGYTYYADSVKGRFTISADTSKNTAYLQMNSLRAEDTAVYYCARMSLHRNFN QQGRSRLLGRMPRTYGMDYWGQGTLVTVSSASTKGPSVFPLAPSSKSTSGGTA ALGCLVKDYFPEPVTVSWNSGALTSGVHTFPAVLQSSGLYSLISVVTVPSSSLGT QTYICNVNHKPSNTKVDKKVEPKSCDKTHT (SEQ ID NO: 69) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQYYSLITFGQGTKVEIKRTVAA PSVFIFPPSDSQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 70) |
| 33D4 | VH | EVQLVESGGGLVQPGGSLRLSCAASGFNIYYSSMHWVRQAPGKGLEWVASISP YSGSTYYADSVKGRFTISADTSKNTAYLQMNSLRAEDTAVYYCARSVHMKLSN KILSGWSWNNSFYAMDYWGQGTLVTVSSASTKGPSVFPLAPSSKSTSGGTAAL GCLVKDYFPEPVTVSWNSGALTSGVHTFPAVLQSSGLYSLSSVVTVPSSSLGTQT YICNVNHKPSNTKVDKKVEPKSCDKTHT (SEQ ID NO: 71) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQSSYSLITFGQGTKVEIKRTVA APSVFIFPPSDSQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 72) |

TABLE 3 -continued

Sequences for the light chain variable region (VL) and a heavy chain
variable region (VH) from each clone shown in Table 2.

| Clone Name | VH or VL Chain | Sequence |
|---|---|---|
| 3G9 | VH | EVQLVESGGGLVQPGGSLRLSCAASGFNIYYSSIHWVRQAPGKGLEWVASIYSY SGYTYYADSVKGRFTISADTSKNTAYLQMNSLRAEDTAVYYCARATNEKFRRK SLQVRLLMRSWLAYAMDYWGQGTLVTVSSASTKGPSVFPLAPSSKSTSGGTAA LGCLVKDYFPEPVTVSWNSGALTSGVHTFPAVLQSSGLYSLSSVVTVPSSSLGTQ TYICNVNHKPSNTKVDKKVEPKSCDKTHT (SEQ ID NO: 73) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQASYAASALITFGQGTKVEIKR TVAAPSVFIFPPSDSQLKSGTASVVCLLNNFYPREAKVQWKVDNALQSGNSQES VTEQDSKDSTYSLSSTLTLSKADYEKHKVYACEVTHQGLSSPVTKSFNRGEC (SEQ ID NO: 74) |
| 33D2 | VH | EVQLVESGGGLVQPGGSLRLSCAASGFNLYYSSIHWVRQAPGKGLEWVAYISSY SGYTSYADSVKGRFTISADTSKNTAYLQMNSLRAEDTAVYYCARSKYGPASRQ LASRTSWSGPRGKYGMDYWGQGTLVTVSSASTKGPSVFPLAPSSKSTSGGTAA LGCLVKDYFPEPVTVSWNSGALTSGVHTFPAVLQSSGLYSLSSVVTVPSSSLGTQ TYICNVNHKPSNTKVDKKVEPKSCDKTHT (SEQ ID NO: 75) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQAYGSYLITFGQGTKVEIKRTV AAPSVFIFPPSDSQLKSGTASVVCLLNNFYPREAKVQWKVDNALQSGNSQESVT EQDSKDSTYSLSSTLTLSKADYEKHKVYACEVTHQGLSSPVTKSFNRGEC (SEQ ID NO: 76) |
| 33C4 | VH | EVQLVESGGGLVQPGGSLRLSCAASGFNLYSSSMHWVRQAPGKGLEWVASIYP YYGYTYYADSVKGRFTISADTSKNTAYLQMNSLRAEDTAVYYCARPTTSRVNK KLFRVSVLHPGSYGMDYWGQGTLVTVSSASTKGPSVFPLAPSSKSTSGGTAALG CLVKDYFPEPVTVSWNSGALTSGVHTFPAVLQSSGLYSLSSVVTVPSSSLGTQTY ICNVNHKPSNTKVDKKVEPKSCDKTHT (SEQ ID NO: 77) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQASYLITFGQGTKVEIKRTVAA PSVFIFPPSDSQLKSGTASVVCLLNNFYPREAKVQWKVDNALQSGNSQESVTEQ DSKDSTYSLSSTLTLSKADYEKHKVYACEVTHQGLSSPVTKSFNRGEC (SEQ ID NO: 78) |
| 32E10 | VH | EVQLVESGGGLVQPGGSLRLSCAASGFNIYSYSMHWVRQAPGKGLEWVAYIYP YSGYTYYADSVKGRFTISADTSKNTAYLQMNSLRAEDTAVYYCARLDRDRYIH VGRAGNTYSNYYYVMDYWGQGTLVTVSSASTKGPSVFPLAPSSKSTSGGTAAL GCLVKDYFPEPVTVSWNSGALTSGVHTFPAVLQSSGLYSLSSVVTVPSSSLGTQT YICNVNHKPSNTKVDKKVEPKSCDKTHT (SEQ ID NO: 79) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQPWGAASLITFGQGTKVEIKRT VAAPSVFIFPPSDSQLKSGTASVVCLLNNFYPREAKVQWKVDNALQSGNSQESV TEQDSKDSTYSLSSTLTLSKADYEKHKVYACEVTHQGLSSPVTKSFNRGEC (SEQ ID NO: 80) |
| 32C2 | VH | EVQLVESGGGLVQPGGSLRLSCAASGFNLYYYSMHWVRQAPGKGLEWVAYISP YSSSTYYADSVKGRFTISADTSKNTAYLQMNSLRAEDTAVYYCARSQHAKKSTI IRMLEHQSRSGMQYVMDYWGQGTLVTVSSASTKGPSVFPLAPSSKSTSGGTAA LGCLVKDYFPEPVTVSWNSGALTSGVHTFPAVLQSSGLYSLSSVVTVPSSSLGTQ TYICNVNHKPSNTKVDKKVEPKSCDKTHT (SEQ ID NO: 81) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQSSYSLITFGQGTKVEIKRTVA APSVFIFPPSDSQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 82) |
| 3B2 | VH | EVQLVESGGGLVQPGGSLRLSCAASGFNFSSSSIHWVRQAPGKGLEWVASIYSS YSSTYYADSVKGRFTISADTSKNTAYLQMNSLRAEDTAVYYCARSTAATTLSR MSRSYWTIQLPYGMDYWGQGTLVTVSSASTKGPSVFPLAPSSKSTSGGTAALG CLVKDYFPEPVTVSWNSGALTSGVHTFPAVLQSSGLYSLSSVVTVPSSSLGTQTY ICNVNHKPSNTKVDKKVEPKSCDKTHT (SEQ ID NO: 83) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQSSYSLITFGQGTKVEIKRTVA APSVFIFPPSDSQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 84) |
| 33F5 | VH | EVQLVESGGGLVQPGGSLRLSCAASGFNLYYSYMHWVRQAPGKGLEWVAYISP SSSSTYYADSVKGRFTISADTSKNTAYLQMNSLRAEDTAVYYCARNFRVESAGR PGKTVLRKDGKYAMDYWGQGTLVTVSSASTKGPSVFPLAPSSKSTSGGTAALG CLVKDYFPEPVTVSWNSGALTSGVHTFPAVLQSSGLYSLSSVVTVPSSSLGTQTY ICNVNHKPSNTKVDKKVEPKSCDKTHT (SEQ ID NO: 85) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQSSVGLFTFGQGTKVEIKRTVA APSVFIFPPSDSQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 86) |

TABLE 3 -continued

Sequences for the light chain variable region (VL) and a heavy chain
variable region (VH) from each clone shown in Table 2.

| Clone Name | VH or VL Chain | Sequence |
|---|---|---|
| 32C11 | VH | EVQLVESGGGLVQPGGSLRLSCAASGFNLYYSSIHWVRQAPGKGLEWVASISSY SSYTYYADSVKGRFTISADTSKNTAYLQMNSLRAEDTAVYYCAREIHMLSRQA RYLRDGRRPRGSMYVMDYWGQGTLVTVSSASTKGPSVFPLAPSSKSTSGGTAA LGCLVKDYFPEPVTVSWNSGALTSGVHTFPAVLQSSGLYSLSSVVTVPSSSLGTQ TYICNVNHKPSNTKVDKKVEPKSCDKTHT (SEQ ID NO: 87) |
| | VL | DIQMTQSPSSLSASVGDRVTITCRASQSVSSAVAWYQQKPGKAPKLLIYSASSLY SGVPSRFSGSRSGTDFTLTISSLQPEDFATYYCQQYGAGLITFGQGTKVEIKRTVA APSVFIFPPSDSQLKSGTASVVCLLNNFYPREAKVQWKVDNALQSGNSQESVTE QDSKDSTYSLSSTLTLSKADYEKHKVYACEVTHQGLSSPVTKSFNRGEC (SEQ ID NO: 88) |

As expected, these CDR-H3 regions were enriched in basic (Arg and Lys) and hydrophilic (Asn, Gln, Thr and Ser) residues while of the levels of negatively charged (Asp and Glu) and hydrophobic (Ala, Leu, Val, Phe and Trp) residues was decreased, likely leading to a better solubility of Fabs and more efficient interactions with the negatively charged surface of the MMP-14 active site pocket (Fernandez-Catalan, et al. (1998) *EMBO J* 17(17): 5238-5248). Furthermore, several individual clones displayed a histidine residue in their CDR-H3 regions that was likely important for coordinating the active site zinc ion in MMP-14. Notably, there were no Cys in most of the CDR-H3s (except the 3D9, 3A6 and 2H9 clones), suggesting that the unpaired Cys residues interfere with the correct disulfide formation in the Fab constructs. In turn, the CDR-H3 loops of the 3D9 and 3A6 constructs exhibited two Cys residues each and, potentially were able to form intra-loop disulfide bonds.

Figure 8B:
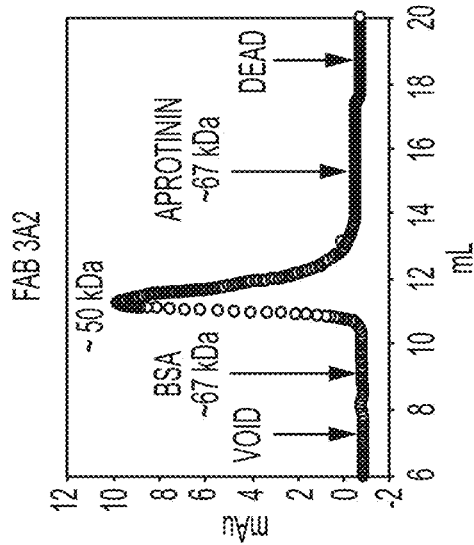
FIGS. 8A-B. SDS-PAGE of purified Fabs and size exclusion chromatography (SEC) analysis of Fab 3A2.
Figure 8A:
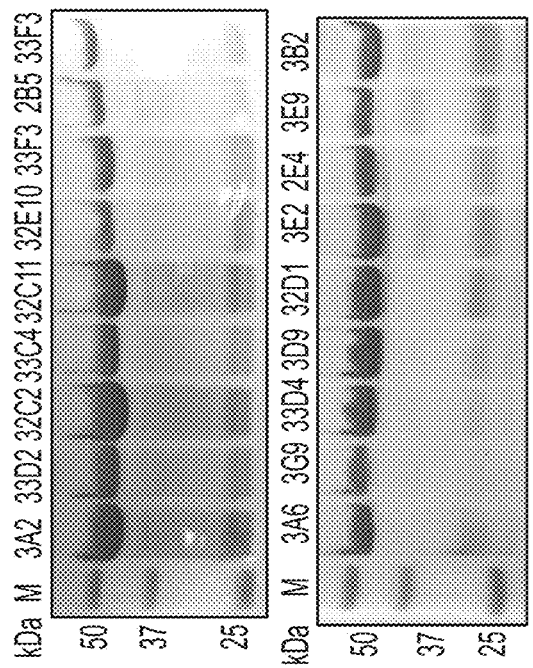

The 20 selected Fabs were then expressed in *E. coli* and isolated from the periplasmic fraction with a typical yield of the purified proteins of 0.5-2 mg per liter of medium (FIG. 8A). Size-exclusion chromatography confirmed that the isolated Fab samples were highly soluble and present as monomers in solution, without any significant level of aggregation (FIG. 8B). The purified Fab samples were stable for at least one month at 4° C. without visible aggregates or degradations verified by SDS-PAGE.

Figure 9A:
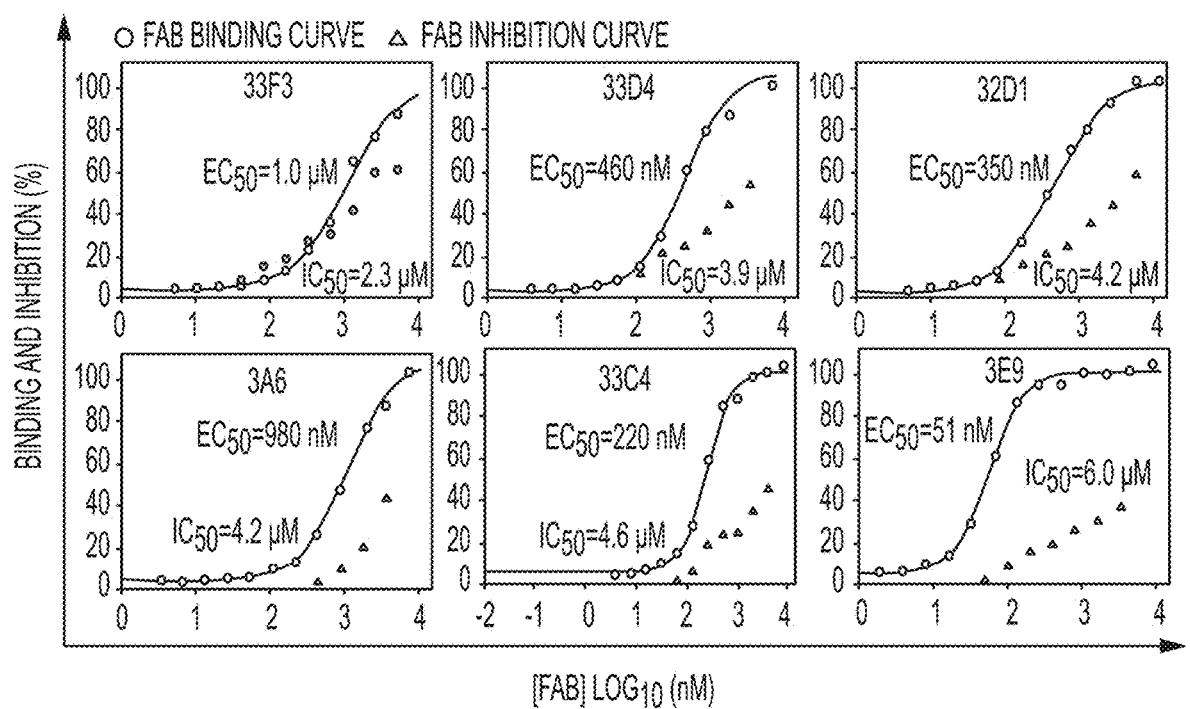
FIGS. 9A-B. Dose-response curves of binding affinity (circle) and inhibition $IC_{50}$ (triangle) of representative low potency inhibitory Fabs (FIG. 9A) and non-inhibitory Fabs (FIG. 9B). 1 µM of quenched-fluorescent substrate peptide and 1 nM cdMMP-14 were used in FRET inhibition assays.

The binding affinity of the purified Fabs with MMP-14 was measured using ELISA. The $EC_{50}$ value of the samples was in a 3.8-1,600 nM range (Table 2). The most efficient binders were 3A2 (3.8 nM), 3D9 (6.4 nM) and 32E10 (9.7 nM) while the $EC_{50}$ value of the additional five Fabs was between 24 and 51 nM (Table 2, FIG. 2A, FIG. 9).

Figure 9B:
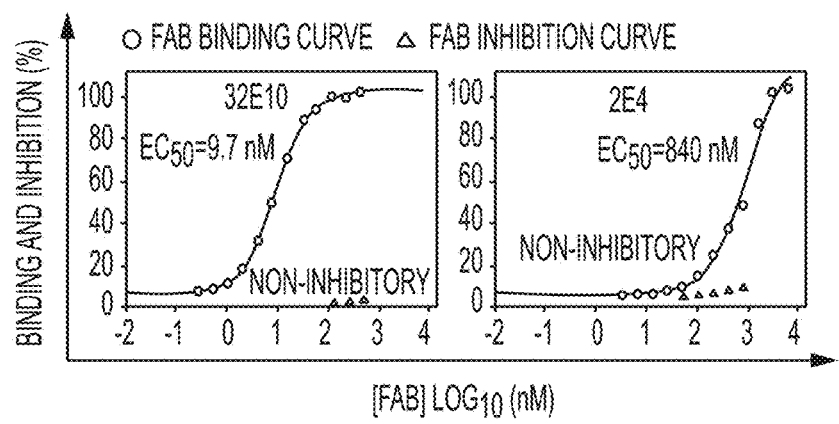

14 (70%) from the 20 Fabs that were purified inhibited MMP-14 proteolysis of the fluorescent peptide substrate (7-methoxycoumarin-4-yl)Acetyl-Pro-Leu-Gly-Leu-(3-[2, 4-dinitrophenyl]-L-2,3-diaminopropionyl)-Ala-Arg-NH$_2$ (SEQ ID NO:123) with the $IC_{50}$ value between 9.7 nM and 8 (Table 2). The presence of 70% of the inhibitory clones among the binders is remarkably high especially if compared with the previous studies of the inhibitory antibodies (Devy et al. (2009) *Cancer Res* 69(4):1517-1526; Zhang, et al. (2012) *FASEB J* 27(2): 581-589). The $IC_{50}$ value of Fabs 3A2, 3E2 and 3D9 was 9.7, 42 and 61 nM, respectively, while the $IC_{50}$ value of three additional Fabs was in a 240-420 nM range (Table 2 and FIG. 2A). Interestingly, Fab 3D9 showed a pH dependent manner of inhibition: its potency at pH 6.5 ($IC_{50}$=10.5 nM) was multi-fold higher than at neutral pH 7.5 ($IC_{50}$=65 nM) or weak alkaline pH 8.5 conditions ($IC_{50}$=157 nM). Likely this pH dependent behavior is at least partially attributed to the histidine protonation in its CDR-H3 sequence (Igawa et al., (2014) *Biochim Biophys Acta* 1844(11):1943-1950). Because cancer cells normally thrive in an acidic microenvironment (Griffiths J R (1991) *Br J Cancer* 64(3):425-427), this characteristic of Fab 3D9 and its derivatives could enhance their targeting selectivity towards tumor tissues with therapeutic benefits in cancer treatment. Fab 3E9, the most enriched clone that was isolated through phage panning (22 repeats), showed a moderate, 51 nM, binding capacity, but its inhibitory potency was low ($EC_{50}$=6.0 µM) (Table 2 and FIG. 9A). The enrichment of this clone was likely a result of high growth rate and/or high expression level relative to other Fab clones. Similarly, a few high affinity Fabs, e.g. 32E10 ($EC_{50}$=9.7 nM) did not inhibit MMP-14, suggesting that the efficient binding does not directly correlate with high inhibitory potency of the antibody (FIG. 9B).

Figure 2A:
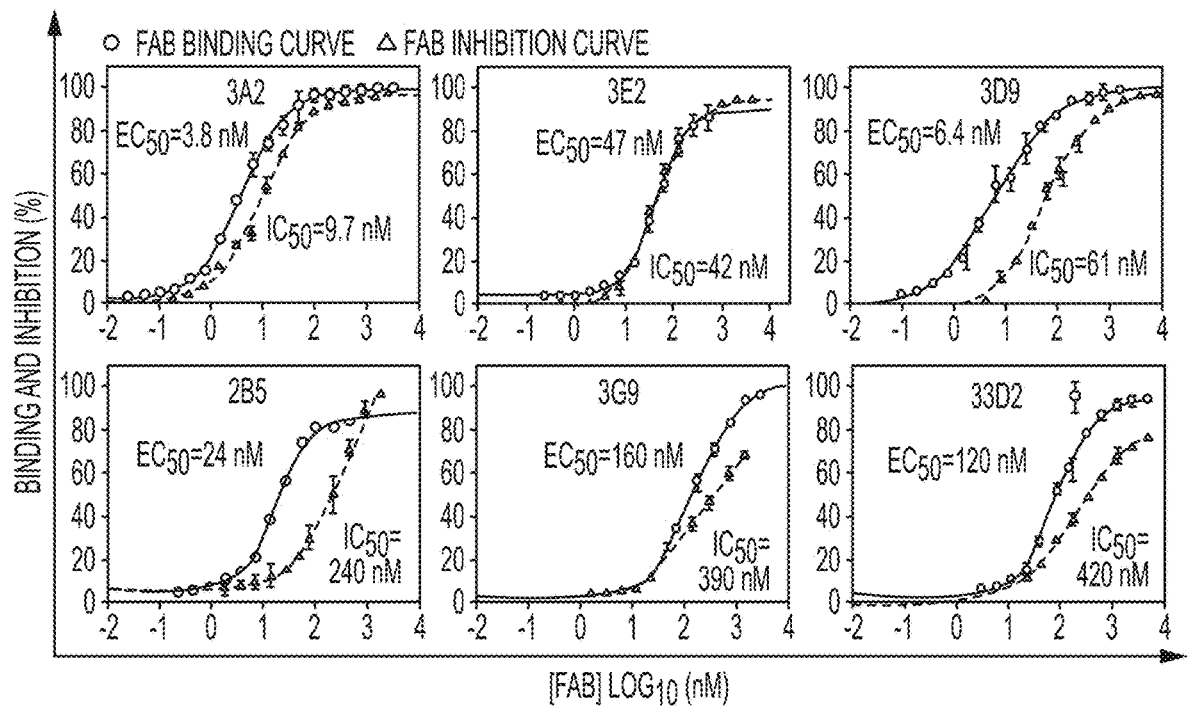
FIGS. 2A-B. Biochemical characterizations of representative high inhibitory potency Fabs.
Figure 2B:
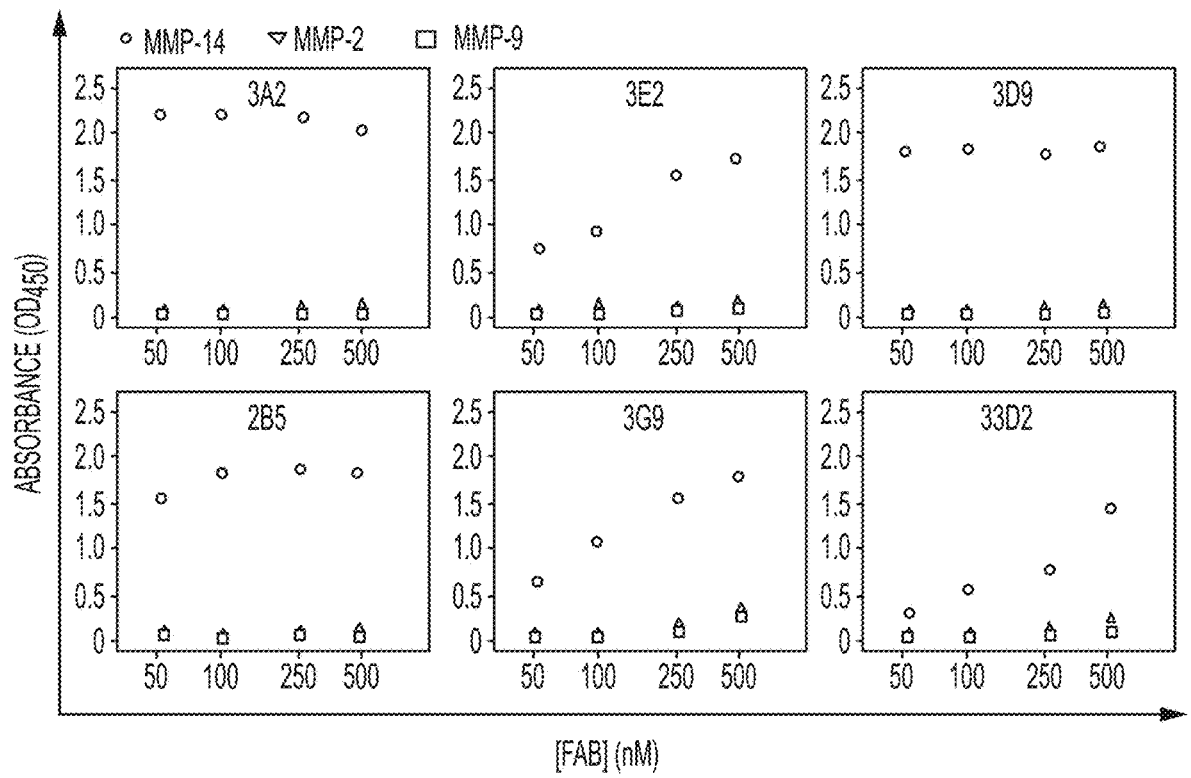

Because selectivity is the prime parameter for the MMP inhibitors, it was next assessed if the most promising Fabs cross-reacted with MMPs that are distinct from MMP-14. According to the ELISA results, all of the six Fabs that were tested were highly selective for MMP-14. Indeed, Fabs 3A2, 3E2, 3D9 and 2B5 were incapable of binding to MMP-2 and MMP-9 even at a high concentration of 500 nM. The two other Fabs, 33D2 and 3G9, were approximately 10- to 20-fold more selective for MMP-14 relative to MMP-2 and MMP-9 (FIG. 2B).

Fab 3A2 is a Highly Potent Competitive Inhibitor of MMP-14.

Figure 3A:
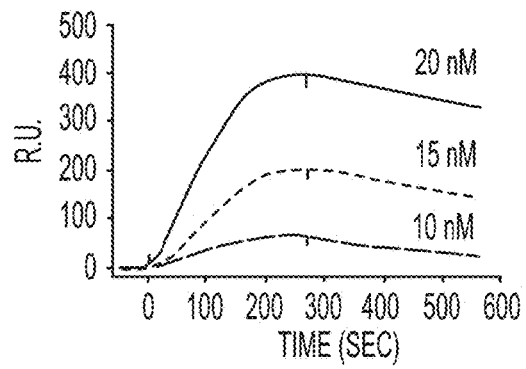
FIGS. 3A-E. Binding affinity and inhibition potency measurements, inhibitor type determination, and epitope mapping of Fab 3A2.

The most efficient inhibitor, Fab 3A2, was studied in a more detail to determine both its inhibitory mechanism and its binding mode. The binding kinetics of Fab 3A2 to MMP-14 was examined using surface plasmon resonance spectroscopy (FIG. 3A). A concentration-dependent saturable binding of 10-20 nM Fab 3A2 to immobilized MMP-14 was observed. Apparent equilibrium binding constants were determined using the steady-state region of sensograms with a kinetic association coefficient ($k_{on}$) equaled to 3.68× $10^5 M^{-1} s^{-1}$ and a kinetic dissociation coefficient ($k_{off}$) equaled to $1.79 \times 10^{-3} s^{-1}$. The equilibrium dissociation constant ($K_D$) calculated from the ratio $k_{off}/k_{on}$ was 4.76 nM and this value agreed well with the ELISA data (FIG. 2A).

Figure 3B:
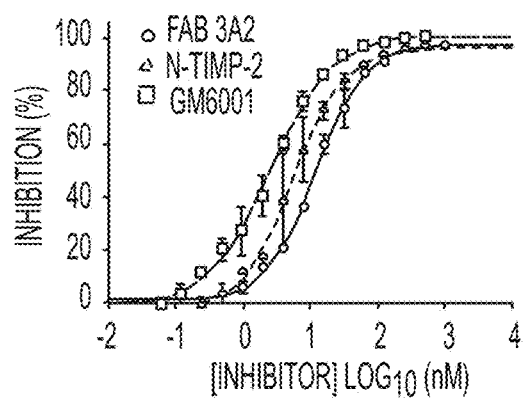
Figure 3C:
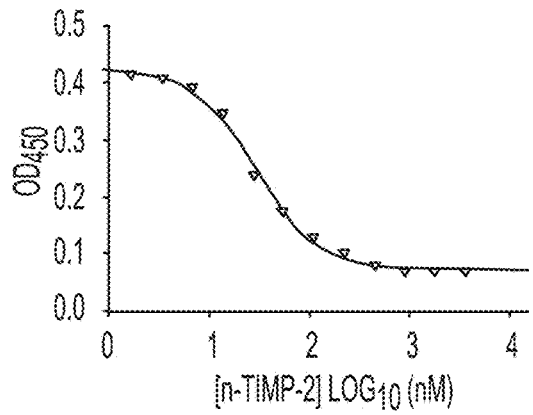
Figure 3D:
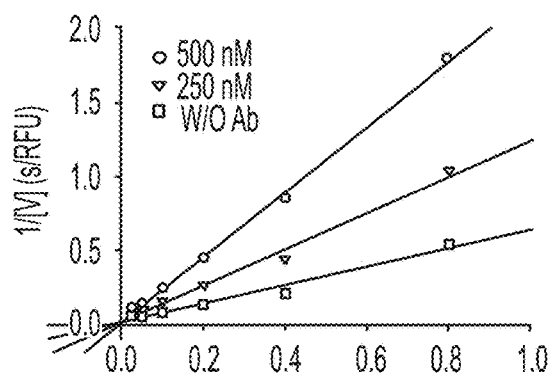

The inhibitory $IC_{50}$ value of Fab 3A2 was 9.7+1.2 nM and similar with that of the individual N-terminal inhibitory domain of tissue inhibitor of metalloproteinase-2 (n-TIMP-2, $IC_{50}$=5.1+2.4 nM) and GM6001, a potent, albeit nonselective, hydroxamate inhibitor of MMPs (2.1±0.6 nM) (FIG. 3B). Increasing concentrations of n-TIMP-2 reduced the binding of Fab 3A2 to MMP-14 (FIG. 3C), suggesting an overlap of their respective binding sites in MMP-14. To determine the type of inhibition, a series of kinetic assays in the presence of 0, 250, and 500 nM Fab 3A2 were performed. The obtained Lineweaver-Burk plots demonstrate an unchanged maximum velocity ($V_{max}$) and a decreased Michaelis constant ($K_m$) when Fab concentration increased, suggesting that Fab 3A2 performed as a competitive inhibitor of the MMP-14 proteolytic activity (FIG. 3D).

Figure 3E:
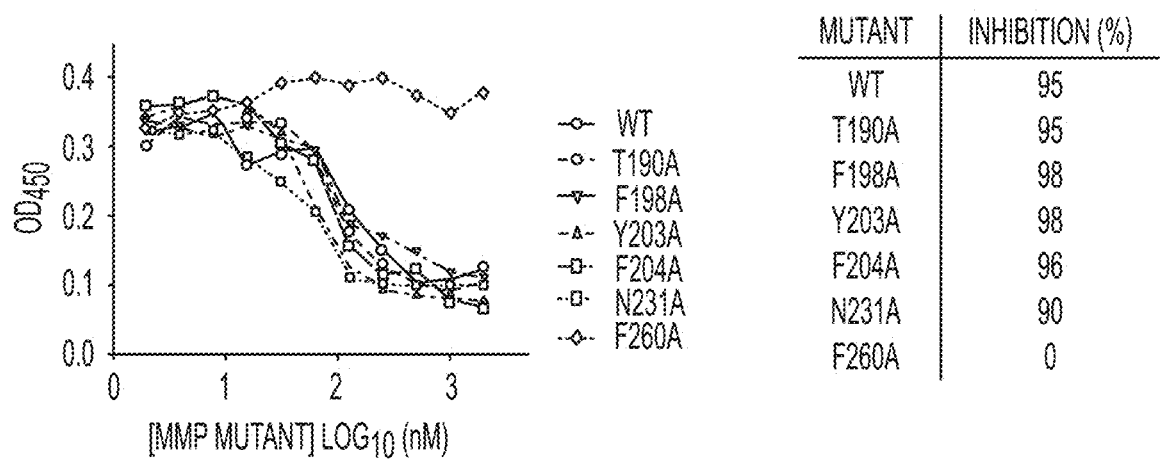

To identify the binding site of Fab 3A2, alanine scanning mutagenesis of MMP-14 was performed. Six residue positions (T190A, F198A, Y203A, F204A, N231A and F260A) in MMP-14 were selected for Ala substitution, based on the following criteria: (i) these selected residue positions are distinct in MMP-14 relative to MMP-2 and MMP-9 (FIG. 11); (ii) the residues are within a 15 Å distance from the catalytic $Zn^{2+}$; (iii) all of these residues exhibit an exposed respective side chain; and (iv) F260 is an essential component of the MMP-14 51' sub-site (Nagase H (2001) *Matrix Metalloproteinase Inhibitors in Cancer Therapy*, eds Clendeninn N J. and Appelt K (Humana Press), pp. 403-420; Gupta et al., (2012) *Matrix Metalloproteinase Inhibitors*, eds Gupta S P (Springer, Basel), pp. 35-56). The resulting MMP-14 mutant constructs were expressed in the periplasmic space of *E. coli* cells to produce active MMP-14 mutants without refolding (Nam et al., (2016) *Biotechnol Bioeng* 113(4):717-723). ELISA and inhibition assay results showed that the performance of the T190A, F198A, Y203A, F204A and N231A mutants did not differ significantly from the original MMP-14. In contrast, the F260A MMP-14 mutant lost its ability to bind to the Fab 3A2 and, consistently, the catalytic activity of this mutant was resistant to inhibition by Fab 3A2 (FIG. 3E). These results, especially when combined, imply that Fab 3A2 is a competitive inhibitor of MMP-14, that the binding site of this antibody overlaps with that of TIMP-2, and that the extended CDR-H3 loop of Fab 3A2 likely accesses the F260 residue from the S1' sub-site in the MMP-14 active site pocket.

To test if the most promising inhibitory Fabs were resistant to MMP-14 proteolysis (Farady et al., (2007) *J Mol Biol* 369(4):1041-1051), Fabs 3A2, 3E2, 3D9 and 2B5 were co-incubated with an excess of MMP-14 (at an enzyme-antibody ratio 1:10) for 16 hr at pH 7.5 and ambient temperature. No significant degradation of the antibodies was observed even under these harsh conditions.

Fab 3A2 Inhibits MMP-14 Collagenolysis and Activation of the MMP-2 Proenzyme.

Figure 4A:
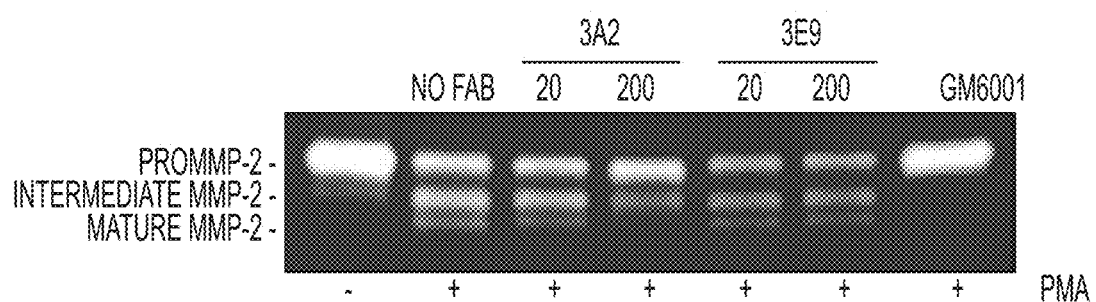
FIGS. 4A-B. Inhibition function of Fab 3A2 on MMP-14 proteolytic activities towards physiological substrates.

Activation of the MMP-2 proenzyme is the most well-known function of cell-surface MMP-14 (Strongin et al., (1995) *J Biol Chem* 270(10):5331-5338). To evaluate the effect of the Fab 3A2 on MMP-2 activation human fibrosarcoma HT1080 cells were used, which produce high levels of MMP-2 naturally. To stimulate activation of the MMP-2 proenzyme by cellular MMP-14, the cells were incubated with tetradecanoyl phorbol acetate, and then co-incubated with Fabs 3A2, 3E9 (a weak inhibitory Fab, $IC_{50}=6$ as the negative control), or GM6001 (a highly potent hydroxamate MMP inhibitor as the positive control). The status of MMP-2 was next analyzed by gelatin zymography (FIG. 4A). As expected at this high concentration of 10 µM, GM6001 totally repressed MMP-2 activation. The low, 200 nM, levels of Fab 3A2 significantly (over 80%) inhibited MMP-14-dependent MMP-2 activation in HT1080 cells. These results were consistent with peptide inhibition assays, confirming that Fab 3A2 inhibited MMP-14 with a high potency in fibrosarcoma cell line.

Figure 4B:
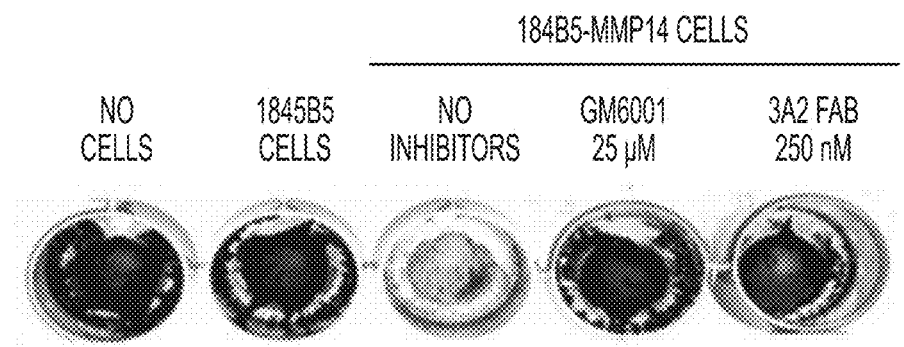

Because MMP-14 is a collagenase, whether Fab 3A2 affected MMP-14 collagenolysis was tested. For these purposes, human mammary epithelial 184B5 cells stably transfected with MMP-14 were employed (Golubkov et al., (2006) *Cancer Res* 66(21):10460-10465). As a control, the original 184B5 cells were used, which naturally produce a low level of MMP-14. Cells were plated on a layer of type I collagen with or without the inhibitors. Following incubation for 5 days, cells were gently detached and the collagen layer was fixed and then stained using Coomassie to visualize the degraded, unstained areas. FIG. 4B shows that collagen was almost completely degraded by 184B5-MMP14 cells. As expected, a high, 25 µM, concentration of GM6001 blocked collagenolysis. Similarly, Fab 3A2, however, at a low, 250 nM, concentration, significantly repressed collagenolysis in 184B5-MMP14 cells. These data suggest that Fab 3A2 performs as a potent and selective inhibitor of MMP-14 in cell-based assays and that this antibody represses MMP-14 proteolysis of its natural, physiologically-relevant substrates.

Discussion

Monoclonal antibodies (mAbs) are ubiquitous in biomedical research and medicine. A variety of methodologies have recently been developed for recombinant antibody discovery. The design of mAbs with the selective proteinase-inhibiting functions, however, remains a significant challenge because of (i) the low antigenicity of the catalytic centers that are normally buried deeply in the enzyme globule, and (ii) the lack of the reliable function-based selection methods. For example, in an attempt to isolate the antibodies capable of inhibiting serpase (a membrane-associated serine protease encoded by the fibroblast activation protein gene), 40 efficiently binding scFv clones were identified in a human naïve scFv phage display library (over $1 \times 10^{10}$ sequence variants), but only a single scFv construct exhibited inhibition function with a µM range potency (Zhang, et al. (2012) *FASEB J* 27(2): 581-589).

The inhibitor-binder ratio was significantly improved when a specific selection procedure was added to phage panning. Thus, the use of TIMP-2, a natural protein inhibitor of MMP-14, as an eluent of the antigen-binding clones from the MMP-14 bait led to the discovery of 12 inhibitory constructs from 70 affinity clones (a 17% hit rate). TIMP-2 binds to the native MMP-14 enzyme alone rather than to the misfolded and denatured species of the proteinase. The use of TIMP-2 thereby allows one to disregard those antibodies which bind to the denatured MMP-14 forms that are always present in the *E. coli*-derived recombinant proteins. Among these inhibitory clones was the original Fab prototype that was later transformed into mAb DX-2400, a potent and therapeutically efficacious inhibitor of MMP-14 (Devy et al. (2009) *Cancer Res* 69(4):1517-1526; Ager, et al. (2015) *J Natl Cancer Inst* 107(4)).

To support and extend these findings, the current methodology combined this epitope-specific elution with a novel synthetic antibody library design. This approach resulted in the identification of 14 novel inhibitory antibodies from the 20 isolated MMP-14 binders, i.e. with a high, 70%, hit rate. The rationale of the antibody repertoire design was based on the sequence analysis of the inhibitory $V_H$Hs and the crystal structures of the multiple VHH:enzyme complexes. These analyses revealed that the extended CDRs provided the enlarged antigen-binding surface and convex paratopes, which penetrated into the catalytic cleft and inhibited the enzymatic reaction (De Genst, et al. (2006) *Proc Natl Acad Sci USA* 103(12):4586-4591; Desmyter, et al. (1996) *Nat Struct Biol* 3(9):803-811). In addition to the camelid single domain antibodies, inhibitory antibodies were recently developed using the cow antibody scaffolding. In the latter, the protruding domains encoded by the ultra long, up to 60 residue, CDR-H3s are frequent (Liu, et al. (2015) *J Am*

*Chem Soc* 137(12):4042-4045; Zhang, et al. (2013) *Angew Chem Int Ed Engl* 52(32):8295-8298). In agreement, structural studies of the inhibitory antibodies also suggested that the insertion of the long CDR-H3 variable loops (up to 19 residues) into the substrate-binding pocket is required for potent inhibition of MT-SP1 (matriptase) (Schneider, et al. (2012) *J Mol Biol* 415(4): 699-715). Although the alternative inhibitory mechanisms are also known, including those which inactivate enzymes by inducing the conformational changes or by blocking the substrate access (Wu, et al. (2007) *Proc Natl Acad Sci USA* 104(50):19784-19789; Ganesan, et al. (2009) *Structure* 17(12):1614-1624), multiple inhibitory antibodies exhibit the unusually long CDR3s, implying that the extended CDRs are vital for enzyme inhibition. Therefore, the human antibody libraries carrying the long 23-27 residue CDR-H3s were designed and synthesized, which presumably formed the convex paratopes. The presence of these convex paratopes is infrequent in the natural human IgGs which, on average, exhibit the 12 residue long CDR-H3 segments (Wu et al., (1993) *Proteins* 16(1):1-7).

Figures 10A, 10B:
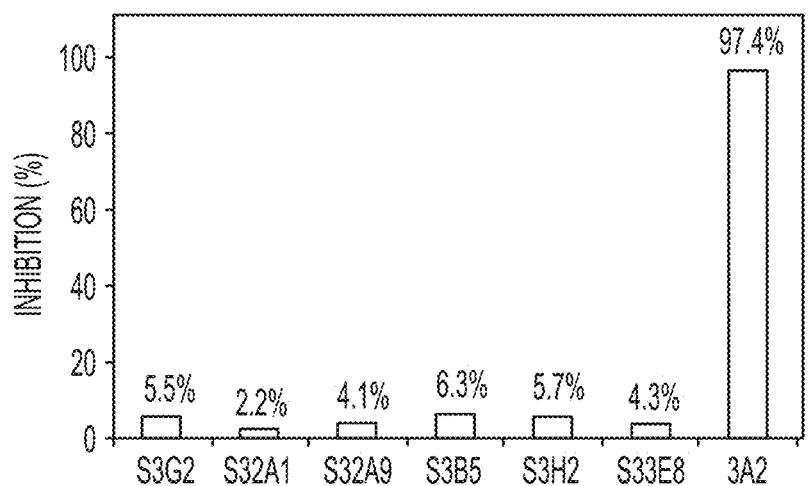
FIGS. 10A-B. Analysis of Fabs isolated from F library (1-17 aa CDR-H3, $3 \times 10^{10}$ diversity) (Persson, et al. (2013) *J Mol Biol* 425(4):803-811).

More specifically, the additional study in which a highly diversified antibody library ($3 \times 10^{10}$ variants) was employed, which exhibited the normal, 1-17 residue, CDR-H3s (Persson, et al. (2013) *J Mol Biol* 425(4):803-811), along with the n-TIMP-2 elution step in the course of phage panning, resulted in six individual Fabs. These Fabs bound to MMP-14 with a low nM affinity (FIG. 10A), however, none was inhibitory (FIG. 10B). These findings strongly support the hypothesis that the convex paratopes formed by the long CDR-H3 segments play an essential role in generating the inhibitory antibodies.

This current study resulted in the 14 inhibitory antibodies from which Fab 3A2, without any maturation, was highly potent against MMP-14. The inhibitory potency of this Fab was similar to that of n-TIMP-2, the natural inhibitor of MMPs, and GM6001, one of the most effective, albeit broad specificity, hydroxamate MMP inhibitors. In addition, Fab 3A2 was highly selective and did not exhibit off-target effects with other MMP family members such as MMP-2 and MMP-9. Importantly, Fab 3A2 efficiently repressed the activity of cellular MMP-14 on its physiological substrates such as MMP-2 and type I collagen. In addition to Fab 3A2, this research led to the discovery of other several potent inhibitors with the promising selectivity and potency against MMP-14 with the $IC_{50}$ value in a 42-240 nM range. This novel inhibitory Fab panel provides a rich pool of lead candidates for the further selection of therapeutics and fine-tuning of pharmacological properties through affinity maturation and solubility/stability improvement.

Mutagenesis of MMP-14 rather than a linear peptide approach (Shiryaev, et al. (2013) *Oncogenesis* 2:e80) followed by the expression of mutants in the periplasm of *E. coli* (Nam et al., (2016) *Biotechnol Bioeng* 113(4):717-723) allowed for the rough mapping of the Fab 3A2 epitope in the MMP-14 catalytic domain. This data indicates that Fab 3A2 targets the S1' pocket of MMP-14 and directly competes with both the substrate and n-TIMP-2 bindings (FIG. 5A). Approximately 25% of residues of the Fab 3A2 CDR-H3 residues are positively charged (Lys/Arg/His), suggesting potential interactions between the CDR-H3 loop and the negatively charged active site vicinity of MMP-14 (FIG. 5B). The additional epitope mapping studies with Fab 3D9 pointed to the involvement of F204 that is localized on the opposite site of the MMP-14 enzymatic cleft (FIG. 5A) suggesting a level of similarity between the inhibitory mechanisms of Fabs 3A2 and 3D9.

The MMP family members are promising drug targets in pathologies ranging from atherosclerosis and stroke to cancer and arthritis. The long CDR-H3 synthetic Fab libraries that were constructed have already been applied for identification of inhibitory antibodies to other MMPs including MMP-2 and MMP-9. It is highly likely that the general methodology that was developed and successfully used in this study could be readily re-employed to design the selective antibody inhibitors to the additional individual MMPs. These selective inhibitors can also be exploited as research tools to shed more light on the MMP functionality in normal and patho-physiological conditions. Furthermore, this antibody design technology could be generalized and applied to the targets outside of the MMP family. Overall, this proof-of-principle study suggests that the synthetic antibody libraries with the extended CDR-H3 segments have a potential to generate selective function-blocking antibodies to a number of enzymes in which druggable pockets are buried deeply inside the protein globule and which cannot be accessed by the antibodies designed by current methodologies.

Materials and Methods

Construction of Long CDR-113 Fab Phage Libraries.

Six degenerate polynucleotides (Table 1) encoding the randomized 23, 25 and 27 residue long CDR-H3 segments, and the partial framework region 3 (FR3) and FR4 were synthesized by IDT (Coralville, Iowa). To mimic the camelid antibody CDR3 repertoires, customized XYZ codons were synthesized using the following proportion of nucleotides: X=38% G, 19% A, 26% T and 17% C; Y=31% G, 34% A, 17% T and 18% C; and Z=24% G and 76% C. The XYZ codons were employed to construct the 23 residue long CDR-H3 fragments. The standard NNS codons were used for constructing the 25 and 27 residue long CDR-H3s. The long CDR-H3 fragments were assembled by overlap extension without PCR amplification using T4 DNA polymerase and T4 DNA ligase (Ge et al., (2010) *Biotechnol Bioeng* 106(3):347-357). The assembled long CDR-H3 fragments were gel purified, digested with AflII/HindIII and cloned into the C-terminus of the β-lactamase gene. CDR-H3 libraries were transformed into *E. coli* Jude-I (DH10B harboring the F' factor derived from XL1-Blue) and incubated on 2×YT agar plates supplemented with 0.5 mM isopropyl β-D-1-thiogalactopyranoside (IPTG) and 50 µg/ml ampicillin to remove stop codons and reading-frame shifts (Seehaus et al., (1992) *Gene* 114(2):235-237). Selected in-frame long CDR-H3 fragments were cloned into AflII/BsmBI sites on phagemids of a synthetic Fab antibody library (Persson, et al. (2013) *J Mol Biol* 425(4):803-811). The constructed Fab phage libraries carrying long CDR-H3s were transformed into *E. coli* XL1-Blue by electroporation and library quality was validated by DNA sequencing. The expression profile of dozens of randomly picked Fab phage clones was tested by Western blotting using the anti-FALG-horseradish peroxidase (HRP) conjugates.

Production and Biotinylation of MMP-2, MMP-9, MMP-14 and n-TIMP-2.

The catalytic domain of MMP-2 and MMP-14 was cloned, expressed, purified and refolded as described previously (Nam et al., (2013) *Biotechnol Bioeng* 110(11):2856-2864). The catalytic domain of MMP-9 was produced without refolding by soluble expression in the periplasmic place of *E. coli* (Nam et al., (2016) *Biotechnol Bioeng* 113(4): 717-723). Enzymatic activities of MMPs were analyzed by cleavage assays using a quenched fluorescent peptide substrate Mca-Lys-Pro-Leu-Gly-Leu-Dap(Dnp)-Ala-Arg-$NH_2$ (SEQ ID NO:124) (Bachem, Torrence, Calif.). The reactions were performed in TBS (50 mM Tris-HCl pH 7.5, 150 mM NaCl, 5 mM CaCl$_2$, 100 µM ZnCl$_2$) in the presence of 1-40 µM substrate and 10 nM MMPs. Fluorescent signals (RFU) with the excitation at 328 nm and the emission at 393 nm were monitored continuously with 10 sec intervals using a Synergy H4 microplate reader (BioTek, San Diego, Calif.) to determine K., and k$_{cat}$. The purified MMP-2, -9 and -14 catalytic domains were biotinylated using the EZ-Link Sulfo-NHS-LC-Biotin reagent (Pierce, Rockfold, Ill., USA) and applied in phage panning and ELISA. MMP-14 mutant genes were constructed by overlapping PCR and similarly expressed and isolated from the periplasm of E. coli. The N-terminal domain of TIMP-2 (n-TIMP-2) was produced by E. coli periplasmic expression and affinity-purified as previous study described (Nam et al., (2016) Biotechnol Bioeng 113(4):717-723).

Phage Panning and Monoclonal ELISA.

Standard protocols were applied for phage preparations and ELISA with modifications (Pardon, et al. (2014) Nat Protoc 9(3):674-693; Fellouse et al., (2013) Making and Using Antibodies, eds Matthew R. Kase (CRC press), pp. 151-172). Briefly, ~10$^{13}$ phage particles of the constructed long CDR Fab library were depleted by incubation in wells of a microtiter plate coated with streptavidin at ambient temperature for 1 hr with gentle shaking at 700 rpm. The streptavidin-depleted phage library was then transferred to wells of a microtiter plate coated with streptavidin and biotinylated MMP-14 and incubation was continued at ambient temperature for 1 hr. After washing 10 times with TBS containing 0.1% Tween 20 (TBST) and 5 times with TBS, MMP-14 binders were eluted by incubation with 6 µM n-TIMP-2 at ambient temperature for 1 hr. The remaining phages were further eluted with 100 mM triethylamine. In the second and the third rounds of selection, to increase stringency the wells were washed 20 times with TBST followed by 5 times with TBS. The antigen concentration was reduced to 2-fold in the third round. Monoclonal phage ELISA was performed in wells of a microtiter plate coated with streptavidin in 0.5% gelatin and then biotinylated MMP-14. The wells coated with biotinylated BSA, but not MMP-14, were used as a control. The coated plates were incubated with the supernatant aliquots of the monoclonal phage cultures. Anti-M13-HRP conjugate and TMB were added to develop the signals. The clones with the signal ratios of MMP-14 to BSA over 5 were considered positive.

Cloning, Expression and Purification of Fabs.

Selected Fab genes were cloned into the Fab expression vector containing the PhoA promoter, a STII leader peptide, and a His tag at the C-terminus of the heavy chain (Fellouse et al., (2013) Making and Using Antibodies, eds Matthew R. Kase (CRC press), pp. 151-172). After expression in E. coli BL21 at 30° C. overnight, Fabs were purified from the periplasmic fraction by Ni-NTA chromatography (Goldman et al., (2003) J Environ Monit 5(3):380-383), dialyzed against 50 mM HEPES, 150 mM NaCl, pH 6.8, and analyzed by SDS-PAGE. The concentrations of Fabs were measured with NanoDrop 2000 (Thermo Scientific, Waltham, Mass.).

Fab ELISA.

Purified Fab was serially diluted in MMP-14-coated wells followed by incubation at ambient temperature for 1 hr. Bound Fabs were detected using the anti-Fab-HRP conjugate. The half-maximal effective concentration (EC$_{50}$) was calculated from a four-parametric logistic curve-fitting analysis. In the competitive ELISA for epitope mapping, 10 nM Fab 3A2 was incubated with 0-2,000 nM MMP-14 mutants for 2 hr and transferred to the streptavidin-coated wells with biotinylated wild-type MMP-14 for 15 min. Bound Fab 3A2 was detected using the anti-Fab-HRP conjugate.

MMP Inhibition Assay.

The enzymatic activity of the wild type and mutant MMP-14 in the presence of inhibitory Fabs was measured at 37° C. by monitoring the hydrolysis of the fluorogenic peptide at $\lambda_{ex}$=328 nm and $\lambda_{em}$=393 nm (Knight et al., (1992) FEBS Lett 296(3):263-266). Typically, 0-8,000 nM Fab was incubated with 1 nM MMP-14 in TBS buffer for 1 hr at ambient temperature, then the reaction was initiated by adding the substrate to a final concentration of 1 µM. Fluorescence was recorded continuously for 30 min and the initial reaction rates and inhibition constants were calculated by fitting the data to the equation (1), where V$_i$ is initial velocity in the presence of the inhibitor, V$_0$ is the initial velocity in the absence of inhibitor, and [I] is the inhibitor concentration.

$$\frac{V_i}{V_0}\% = \frac{1}{1 + \frac{[I]}{IC_{50}}} \times 100 \qquad (1)$$

To determine the type of inhibition, the initial velocity of MMP-14 was measured as a function of substrate concentration (0-40 µM) at several fixed concentrations of Fab (0-500 nM). The values of apparent K$_m$ and V$_{max}$ were derived by linearization according to the Lineweaver-Burk equation.

Surface Plasmon Resonance Analysis Using Biacore.

MMP-14 was immobilized on a CM5 sensor chip via amine coupling. Fab samples (5-20 nM each) were injected over the surface for the binding experiments performed at 25° C. The data was processed using a monophasic model for nonlinear curve fitting with possible mass transport considered. Association and dissociation rate constants K$_{on}$ and K$_{off}$ were calculated using the BIAevaluation version 4.1 package (Pharmacia).

Gelatin Zymography.

Fibrosarcoma HT1080 cells, which expressed MMP-14 on cell surface, were stimulated for 24 hr in serum-free DMEM supplemented with 50 ng/ml tetradecanoyl phorbol acetate (Sigma-Aldrich, St. Louis, Mo.) alone or in the presence of the indicated concentration of Fabs. The status of MMP-2 in the conditioned medium aliquots was analyzed using a precast 10% acrylamide gel co-polymerized with 0.1% gelatin (Life Technologies, Grand Island, N.Y.). After electrophoresis, the gel was incubated twice for 30 min at ambient temperature in 2.5% Triton X-100 and then for 16-18 hrs at 37° C. in 50 mM Tris-HCl, pH 7.4 containing 10 mM CaCl$_2$, 1 µM ZnCl$_2$, and 0.02% NaN$_3$. The gel was then stained with Coomassie Blue R-250 to visualize the bands with gelatinolytic activity. The broad spectrum hydroxamate MMP inhibitor GM6001 (10 µM) was added to the cells and used as a positive control to inhibit MMP-14 catalytic activity.

MMP-14-Mediated Degradation of Type I Collagen.

24-well plates were coated with neutralized, chilled rat tail type I collagen (300 µg/ml, 350 µl in PBS) for 3 hrs at 37° C. and air dried for 16 hr. The collagen coating was washed with water and rehydrated for 2 hrs at 37° C. in 500 µl serum-free DMEM. The human mammary epithelial cells 184B5, which did not produce MMP-14, served as a negative control. 184B5-MMP14 was obtained by transfecting 184B5 with the full-length MMP-14 gene (Golubkov et al., (2006) *Cancer Res* 66(21):10460-10465). Cells (5×10$^4$) in DMEM-2% FBS were seeded onto the collagen wells and allowed to attach for 3 hr. The medium was then removed and replaced with 350 µl serum-free DMEM alone or DMEM containing 250 nM Fab or 50 µM GM6001. The cells were incubated for 5 days. At day 3, the medium was replaced with fresh serum-free DMEM alone or containing the molecules of interest. At day 5, cells were detached with 2 mM EDTA, and the collagen was then fixed with 4% paraformaldehyde and stained with Coomassie Blue R-250.

Example 2. Effects of 3A2 Fab on Reduction of Melanoma Metastasis

Results

3A2 Fab Reduces Pulmonary Melanoma Metastasis in Mice.

The potency of the 3A2 Fab in reducing the pulmonary metastasis in the experimental melanoma metastasis model was evaluated in mice. B16F1 cells were specifically selected for the in vivo studies because of their high metastatic propensity. To specifically focus on the MT1-MMP function in metastasis, B16F1-mMT1 cells with the enforced expression of murine MT1-MMP and control B16F1-mock cells transfected with the original plasmid alone were employed.

Multiple assays confirmed the overexpression of the functionally active MT1-MMP in B16F1-mMT1 relative to the B16F1-mock cell control. Thus, high level of MT1-MMP in B16F1-mMT1 cells was detected by Western Blotting with the MT1-MMP 3G4 antibody (FIG. 12A). Gelatin zymography demonstrated that B16F1-mMT1 cells (but not the B16F1-mock control) were capable of efficiently activating MMP-2. Finally, the fluorescent MP-3653 reporter (a liposome tagged with a fluorochrome and functionalized with a PEG-5000 chain spacer linked to an inhibitory hydroxamate warhead) that binds to the active cellular MT1-MMP alone and that does not interact with the MT1-MMP proenzyme or with the catalytically inactive MT1-MMP enzyme•TIMP-2 complex, readily highlighted B16F1-mMT1 cells but not the control cells (FIG. 12A). Based on these tests, it was concluded that the control B16F1-mock cells were deficient in MT1-MMP, while the stably transfected B16F1-mMT1 cells overexpressed this membrane protease.

Figures 13A, 13B, 13C:
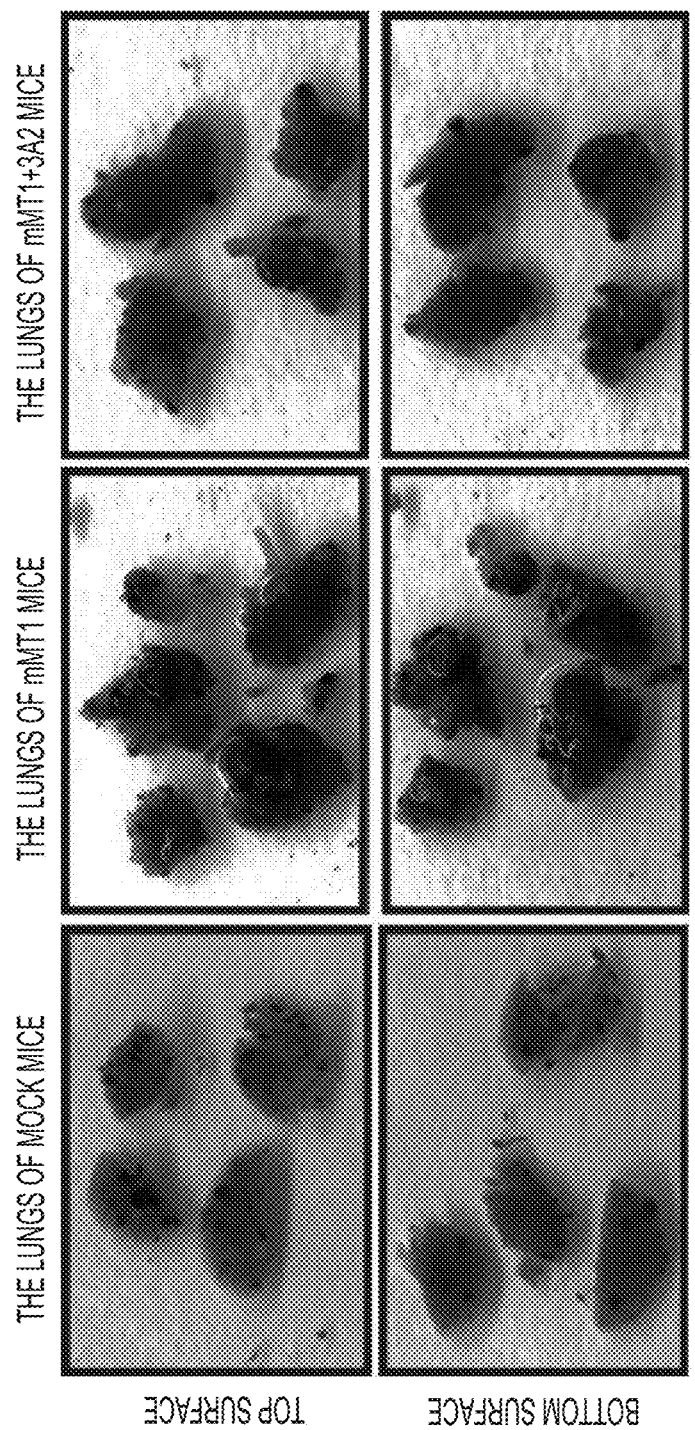
FIGS. 13A-C. Metastatic nodules in mice. Pulmonary melanoma metastatic nodules were counted at day 23 post-cell injection in (FIG. 13A) B16F1-mock (mock), (FIG. 13B) 16F1-mMT1 (mMT1 group) and (FIG. 13C) B16F1-mMT1+3A2 Fab (mMT1+3A2). Representative images are shown.

In these animal tests, B16F1-mMT1 cells were injected i.v. at day 1 into athymic nude mice (n=12, mMT1 mice). Mice injected with B16F1-mock cells (n=6, mock mice) served as a control. Six mice from the mMT1 group received five injections of the 3A2 Fab i.p. (10-15 mg/kg at day 1, 3, 5, 8 and 12) (FIG. 12B). Six other mMT1 mice and the mock mice (n=6) received an injection i.p. of vehicle alone. Additional three mice were left intact and did not receive cells and the antibody. At day 23, mice were euthanized, and their lungs were surgically removed, weighed and photographed (FIG. 12C-D, FIG. 13A-C). Western blotting analysis of the tissue extract confirmed the continuing expression of MT1-MMP in the mMT1 lungs. In turn, the lungs of the mock mice did not exhibit any noticeable levels of MT1-MMP. Because of the massive melanoma lesions, the lung weight in the mMT1 group (0.717±0.160 g) greatly exceeded that in the mock animals (0.239±0.047 g) and the intact mice (0.175±0.023 g). In agreement, the number of metastatic nodules in the mMT1 group (198±31) was approximately 4-fold higher relative to the mock control (55±10). Furthermore, the nodules were bigger in size in the mMT1 mice relative to the control animals (FIG. 13A-B). In general, these observations agree well with the results by others and support the pro-metastatic role of MT1-MMP in cancer. Importantly, the 3A2 antibody injections significantly reduced the lung weight (0.328±0.123 g) and both the number (95±28) and size of metastatic in mice from the mMT1+3A2 mice when (FIG. 13B-C), making these parameters similar to those that were recorded in the MT1-MMP-deficient mock control.

Materials and Methods

Melanoma Pulmonary Metastasis in Mice.

To readily develop pulmonary metastatic lesions, at day 1, 5-6 week-old female athymic Foxn1nu nude mice (Envigo, Indianapolis, Ind.) received a single tail vein injection of B16F1-mock and B16F1-mMT1 cells [0.2×10$^6$ in 0.2 ml Hank's Balanced Salt Solution (HBSS)]. Six and twelve animals received B16F1-mock and B16F1-mMT1 cells, respectively. Additional 3 mice were left intact and served as a control for normal behavior and the normal lung weight. At day 1, 3, 5, 8 and 12, six animals from the B16F1-mMT1 group also received an intraperitoneal injection (i.p.) of the 3A2 Fab (10-15 mg/kg in 150 µl HBSS), while other mice received the vehicle alone. At day 23, mice were euthanized according to the NIH guidelines. The lungs were harvested, washed in ice-cold PBS and weighed. For each mouse, the lungs were photographed and then sectioned (FIG. 13A-C). Metastatic nodules were counted using the digitized lobe images. The lung samples were next snap-frozen. The sections (0.15 mg each) of the lungs were extracted in 0.90 ml 20 mM Tris-HCl, pH 7.4, supplemented with 150 mM NaCl, 0.5% deoxycholate, 1% IGEPAL, 1% Triton X-100, 0.1% SDS, a protease inhibitor cocktail set III, 1 mM phenylmethylsulfonyl fluoride, 10 mM EDTA and 10 µM GM6001. The solubilized material was separated from the pellet by centrifugation (14,000×g; 30 min). The protein concentration was then adjusted in the samples to reach 3 mg/ml. Sample aliquots (20 µg total protein each) were then analyzed by Western blotting under non-reducing conditions with the MT1-MMP AB8345 antibody. All protocols for animal studies were reviewed and approved by the Institutional Animal Care and Use Committee at SBP Medical Discovery Institute.

Example 3: Identification of Highly Selective MMP-14 Inhibitory Fabs by Deep Sequencing Abstract Matrix metalloproteinase (MMP)-14 is an important target for cancer treatment due to its critical roles in tumor invasion and metastasis. Previous failures of all compound-based broad-spectrum MMP inhibitors in clinical trials suggest that selectivity is the key for a successful therapy. With inherent high specificity, monoclonal antibodies (mAbs) therefore arise as attractive inhibitors able to target the particular MMP of interest. As a routine screening method, enzyme-linked immunosorbent assays (ELISA) have been applied to panned phage libraries for the isolation of mAbs inhibiting MMP-14. However, because of suboptimal growth conditions and insufficient antibody expression associated with monoclonal ELISA, a considerable number of potentially inhibitory clones might not be identified. Taking advantage of next-generation sequencing (NGS), enrichment profiles of millions of antibody clones along three rounds of phage panning were monitored, and 20 Fab inhibitors of MMP-14 with inhibition IC$_{50}$ values of 10-4000 nM were identified. Among these inhibitory Fabs, 15 were not found by monoclonal phage ELISA. Particularly, Fab R2C7 exhibited an inhibition potency of 100 nM with an excellent selectivity to MMP-14 over MMP-9.

Inhibition kinetics and epitope mapping suggested that as a competitive inhibitor, R2C7 directly bound to the vicinity of the MMP-14 catalytic site. This study demonstrates that deep sequencing is a powerful tool to facilitate the systematic discovery of mAbs with protease inhibition functions.

INTRODUCTION

Matrix metalloproteinases (MMPs) are a class of zinc dependent endopeptidases responsible for tissue remodeling and extracellular matrix degradation. MMPs play important roles within various aspects of cancer pathology, including tumor growth, metastasis, and angiogenesis (Zarrabi et al., 2011. J. Biol. Chem. 286: 33167-33177; Udi et al., 2015. Structure. 23: 104-115; Golubkov et al., 2005. J. Biol. Chem. 280: 42237-42241). In particular, membrane type-1 matrix metalloproteinase also known as MMP-14 is a leading factor in cell migration due to its ability to cleave cell surface molecules such as CD44, pro-$\alpha_v$ integrin, and transglutaminase (Zarrabi et al., 2011. J. Biol. Chem. 286: 33167-33177; Kajita et al., 2001. J. Cell Biol. 153: 893-904; Baciu et al., 2003. Experimental Cell Research. 291: 167-175; Gingras D, et al., 2001. FEBS 507: 231-236). MMP-14 also processes proMMP-2 into active MMP-2, which promotes the migration of tumor cells (Udi et al., 2015. Structure. 23: 104-115; Deryugina et al., 2001. Experimental Cell Research. 263: 209-223). One of the major challenges with inhibiting MMP-14 as a therapy is the elimination of cross reactivity towards other MMPs. Mounting evidence has suggested that while many facets of MMP proteolytic action are pro-tumorigenic, some MMP family members exhibit tumor-suppressing effects in certain circumstances (Overall C M, Kleifeld O. 2006. Nat. Rev. Cancer. 6: 227-239; Kessenbrock et al., 2010. Cell. 141(1): 52-67)—e.g. MMP-8 favors host defense instead of stimulating tumor proliferation (Decock et al., 2011. J Cell Mol Med. 15:1254-1260), and MMP-9 exhibits opposing functions at different microenvironments (Egeblad M, Werb Z. 2002. Nat. Rev. Cancer. 2: 161-174). For these reasons, selectively blocking individual tumorigenesis-promoting MMPs in an appropriate timeframe is highly desired for a successful therapy. However, the catalytic domains of MMP family members share high amino acid similarity and their active sites are extensively conserved. As a consequence, development of small molecule inhibitors to distinguish different MMPs is extraordinarily difficult (Zucker S, Cao J. 2009. Cancer Biol Ther. 8:2371-2373). Chemical compound inhibitors, e.g. hydroxamates, targeting broad-spectrum MMPs all failed in clinical trials due to severe side effects and a lack of efficacy overall (Turk B. 2006. Nat Rev Drug Discov. 5: 785-799). The demand for highly selective MMP inhibitors makes monoclonal antibodies an attractive alternative for MMP inhibition (Devy L, et al. 2009. Cancer Res. 69:1517-1526; Ager et al., 2015. J Natl Cancer Inst.; 107(4); Schneider et al., 2012. J Mol Biol. 415:699-715; Sela-Passwell N, et al., 2011. Nat Med. 18:143-147; Bonvin P, et al., 2015. Antibodies. 4: 103-122; Smith A J. 2015. Journal of Biomolecular Screening. 20(4): 437-453).

A panel of inhibitory Fabs targeting MMP-14 with high potency and high selectivity has been isolated from a synthetic human antibody library carrying convex paratopes encoded by long CDR-H3 regions with 23-27 amino acids, inspired by camelid antibody repertoires (Nam D. Generation of Highly Selective Monoclonal Antibodies Inhibiting Tumorigenic Proteases [dissertation]. [California]: University of California, Riverside). Unlike human or murine antibodies that have CDR-H3s of 12 and 9 amino acids on average, a large portion of heavy chain antibodies produced by camels or llamas contain long CDR3s that penetrate concave structures of enzyme reaction pockets and inhibit enzymatic functions (Genst et al., 2006. Proc Natl Acad Sci USA. 103:4586-4591; Desmyter et al., 1996. Nat Struct Biol. 3:803-811; Lauwereys et al., 1998. EMBO J. 17(13): 3512-3520; Forsman A M M. 2008. Characterization of llama antibody fragments able to act as HIV-1 entry inhibitors. [PhD thesis][University College London]; Spinelli et al., 1996. Nat Struct Biol. 3:752-757). Using phage panning and monoclonal ELISA screening, 14 Fabs inhibiting MMP-14 were isolated from the constructed long CDR-H3 antibody library. Particularly, Fabs 3A2 and 3D9 exhibited nM potency competitive inhibition towards MMP-14 with no reactivity to MMP-2 or MMP-9. However, it has been demonstrated that standard ELISA screenings are incapable of recovering all the antibodies enriched by phage panning or other screening/selection processes (Ravn et al., 2013. Methods. 60(1): 99-110; Ravn et al., 2010. Nucleic Acids Research. 38: e193), for at least two reasons: (1) slow growth rates of certain enriched clones resulting in low cell density after propagation; (2) low expression levels of certain antibody proteins resulting in weak ELISA signals.

Figure 14:
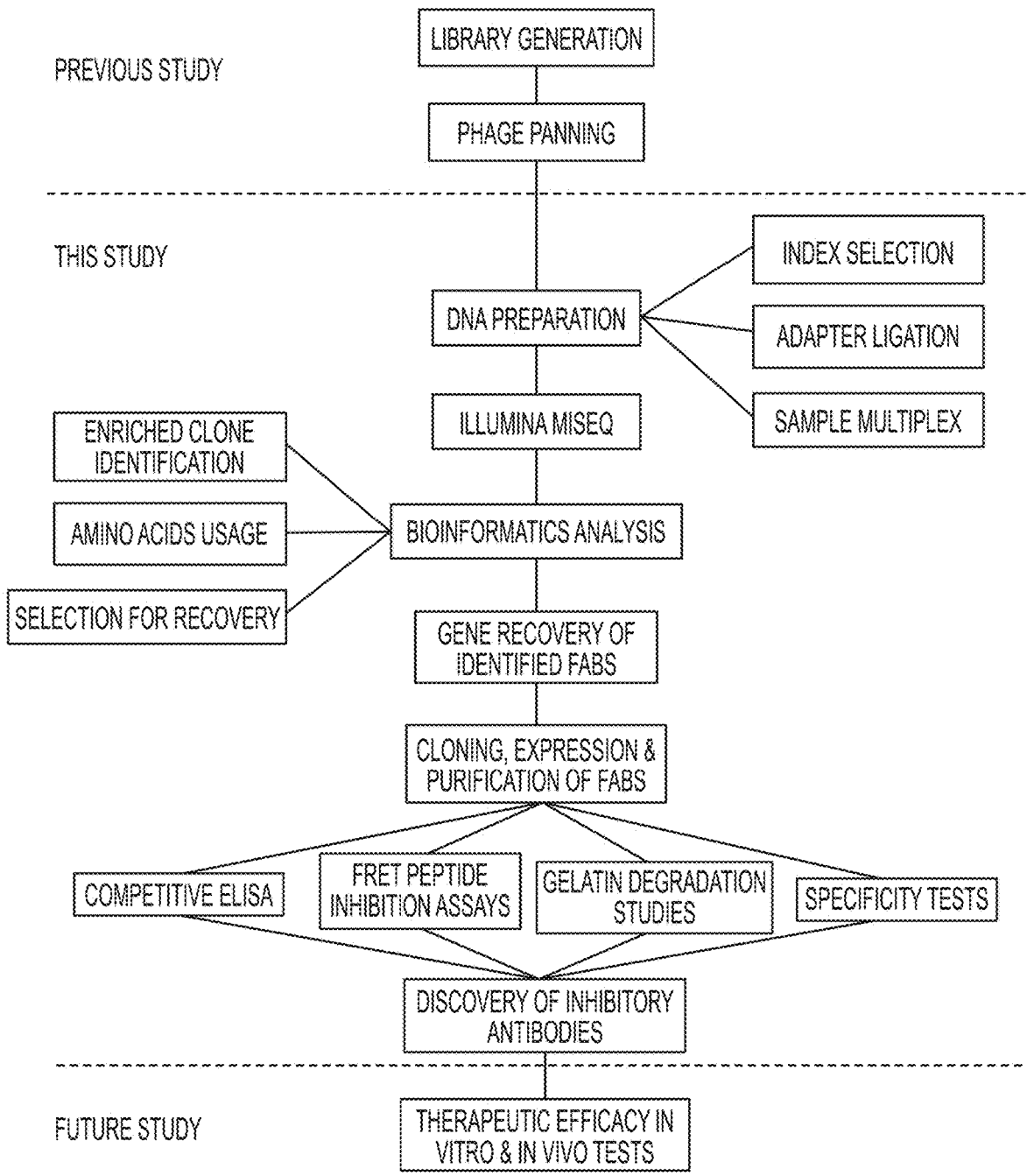
FIG. 14. Illumina sequencing and bioinformatics analysis for discovery of inhibitory antibodies. Synthetic antibody libraries carrying long CDR-H3 were constructed and subjected to three rounds of phage panning against cdMMP-14 (previous study, Nam D. Generation of Highly Selective Monoclonal Antibodies Inhibiting Tumorigenic Proteases [dissertation]. [California]: University of California, Riverside). Panned phage libraries were analyzed by deep sequencing to identify Fab clones inhibiting cdMMP-14, and isolated antibodies were characterized biochemically (this study). The therapeutic efficacy of discovered Fabs can be evaluated by vitro and in vivo tests (future study).

Next-generation sequencing (NGS) technologies have revolutionized multiple aspects of biological researches (Margulies et al. 2005. Nature. 437: 376-380; Pushkarev et al., 2009. Nature Biotechnol. 27: 847-850; Metzker M L. 2010. Nature Reviews Genetics. 11: 31-46; Georgiou et al., 2014. Nat Biotechnol. 32: 158-168), with profound impacts on discovery of specific and functional mAbs (WO2011146514; US20110312505; EP2572203; CA2799746; CN201180035306; Reddy et al., 2010. Nat Biotechnol. 28(9): 965-969; Zhua et al. 2013. Proc Natl Acad Sci USA. 110 (16): 6470-6475; Naqid I A, et al., 2016. Scientific Reports. 6: 24232). By high-resolution profiling of an antibody library's diversity, with sequence and frequency information on virtually all clones during screening process, NGS followed by in-depth analysis has been employed to discover many valuable mAbs not found by ELISA screenings (Ravn et al., 2010. Nucleic Acids Research. 38: e193; Ravn et al., 2013. Methods. 60(1): 99-110; Turner et al., 2016. PLoS ONE 11(2): e0149393). Encouraged by these studies, in-depth analysis to systematically identify and characterize enriched long CDR-H3 clones from the previously panned libraries may be performed (Nam D. Generation of Highly Selective Monoclonal Antibodies Inhibiting Tumorigenic Proteases [dissertation]. [California]: University of California, Riverside). In this study, the DNA samples for Illumina sequencing were prepared without PCR by direct ligation to custom-designed sequencing adapters to avoid introducing amplification bias. After high-throughput sequencing and bioinformatics analysis, the genes of the 29 most abundant Fab clones in the second and the third rounds of panning (R2 and R3) were rescued. Associated Fabs were then produced and tested for affinity, inhibition and selectivity (FIG. 14). Using this technique 20 inhibitory Fabs were identified, of which 15 were not found by previous ELISA screening. This study demonstrated that, as a supplement to ELISA, deep sequencing is a very powerful tool to facilitate the systematic discovery of antibodies with protease inhibitory functions.

Materials and Methods

Preparation of VII Library DNA for Deep Sequencing

Synthetic antibody Fab phage libraries ($1.25 \times 10^9$ variants) carrying extended CDR-H3 (23-27 amino acids) were constructed (Nam D. Generation of Highly Selective Monoclonal Antibodies Inhibiting Tumorigenic Proteases [dissertation]. [California]: University of California, Riverside) and subjected to three rounds of panning against the catalytic domain of MMP-14 (cdMMP-14), which was recombinantly expressed (Nam D, Ge X. 2015. Biotechnol. Bioeng. 113(4):717-23), purified, biotinylated, and immobilized on ELISA plates via biotin-BSA and streptavidin. *E. coli* cells infected with the eluted phages from each round of panning (R1, R2, and R3) as well as the original library (Og), were cultured 6 hours in 2×YT supplemented with 100 µg/ml ampicillin. The Fab library plasmids were miniprepped, and double digested with DraIII and BseRI, to isolate the fragments encoding VH FR2-CDR2-FR3-CDR3-FR4 (~280 bp) from gel electrophoresis (Zymo Research).

The Illumina sequencing adapters P5 and P7 were customized by introducing a DraIn overhang trinucleotide sequence TGG and a BseRI overhang binucleotide sequence TG at their 5' and 3' ends respectively. To distinguish DNA samples from various panning rounds, sequencing indexes selected from Illumina's Nextera Kit were used as the barcodes. To maintain an A+C to G+T ratio of 1:1 for each position of the adapter across the different libraries, IS indexes [N/S/E]501-504 and 17 indexes N703, N704, N709, and N710 were chosen for library samples Og, R1, R2, and R3 respectively. Both strands of modified P5 and P7 adapters containing the selected indexes were synthesized with 5' phosphorylation (IDT), and annealed by gradient cooling from 95° C. to 25° C. over 45 minutes in a thermocycler (Bio-Rad) to generate double stranded adapters.

Prepared libraries of VH fragments were directly ligated with assembled P5 and P7 adapters via the sticky ends, a non-PCR approach without the introduction of biases caused by amplification. Specifically, 400 ng of DNA at a 10:1 molar ratio of adapters to VH fragments was mixed in a 50 µL reaction containing 1,000 U of T4 DNA ligase (NEB). After incubation at 4° C. for 16 hours, unreacted adapters were removed from the ligated products (DNA clean up kit, Zymo Research). The purity and concentrations of adapter ligated VH fragments were determined by spectrophotometry and by RT-qPCR. VH libraries before and after 1, 2, and 3 rounds of panning were multiplexed based on their concentrations to generate a sequencing mixture with a 10:1:1:1 ratio. After multiplexing the quality of the library was checked using an Agilent 2100 Bioanalyzer.

Bioinformatics Analysis

The multiplexed library was subjected to deep sequencing using a MiSeq sequencer (Illumina). Deep sequencing data were analyzed using an automatic bioinformatics pipeline, which combines MATLAB, Perl, Excel, GSplit, and the Windows OS. Large raw FASTQ data files were first split into manageable pieces using GSplit. Each piece was then run through MATLAB to extract the DNA sequences and quality scores. The data was then passed to PERL to isolate high quality sequences containing in-frame CDR-H3 regions. The conserved sequences flanking the CDR-H3 were utilized as the searching motifs for identification of CDR-H3 (Reddy et al., 2010. Nat Biotechnol. 28(9): 965-969). Each clone was ranked and named according to its relative abundancy and library, e.g. clone R2C3 represents the third most abundant clone in the phage library after two rounds of panning.

Cloning, Expression and Purification of Fabs

Genes of identified highly abundant Fab clones were PCR amplified from their associated libraries using a universal forward primer recognizing the 5' of the Fab fragment and clone-specific reverse primers matching the unique CDR-H3 sequences. All the primers were designed to have a Tm of 72° C. After initial extraction a second extension PCR was performed to amplify and introduce a PpuMI cutting site at the 3' of the CDR-H3. A Fab phagemid (Farady et al., 2007. *J Mol Biol.* 369(4):1041-1051) was modified to introduce a PpuMI site via a silent mutation immediately downstream of the CDR-H3 region for direct cloning of amplified Fab genes using NsiI/PpuMI restriction sites. Ligated plasmids were cloned into *E. coli* Jude-I [(DH10B) F'::Tn10 (Tet$^r$)] cells for sequence confirmation, then transformed into BL21 electrocompetent cells for expression.

Fabs containing a 6× His tag (SEQ II) NO:125) at C-terminal of CH1 were produced by culturing transformed BL21 cells in 2×YT at 30° C. for 15 hours. After expression the periplasmic fractions were prepared by osmotic shock with 25% sucrose followed by treatments with lysozyme, EDTA and MgCb. Samples were centrifuged at 15,000×g for 15 minutes at 4° C. to obtain the supernatants containing the Fabs. Periplasmic solutions were then passed through a 0.22 µm filter and purified by using Ni-NTA agarose (Qiagen). Purified Fab samples were buffer exchanged into 50 mM HEPES (pH 7.5) by dialysis at 4° C. using SnakeSkin tubing (Fisher), and concentrated by using ultrafiltration centrifugation tubes with MWCO of 10 kDa (Amicon). The purity and concentration of produced Fabs were determined by SDS-PAGE and $OD_{280}$ absorption measurements.

Antibody Characterizations

Dose-dependent ELISA and specificity tests: cdMMP-9, cdMMP-14 and cdMMP-14 mutants were cloned and produced in their active format in periplasmic space of *E. coli* without refolding or activation (Nam D, Ge X. 2015. Biotechnol. Bioeng. 113(4):717-23). After labeling purified cdMMP-14 using EZ-Link Sulfo-NHS-LC biotinylation kit (Thermo Fisher), biotin-cdMMP-14 was incubated in a streptavidin coated ELISA plate (Thermo Scientific) blocked with biotin-BSA. After washing, 50 µL of 2 µM Fabs were then added to the first well and serially diluted to −1 nM and incubated for 30 minutes at 4° C. After washing, the ELISA signals were developed by anti-Fab-HRP (Sigma) and TMB (Thermo Scientific). The color development reaction was stopped by addition of H2504, and the absorptions at 450 nm were measured. Bindings of Fabs to cdMMP-9 were studied by competitive ELISA. Fabs were incubated with a gradient concentration of cdMMP-9 from 4 µM to 2 nM for 1.5 hours at room temperature. After incubation, samples were transferred to an ELISA plate coated with 100 nM cdMMP-14 and processed as described above.

FRET Inhibition Assays:

The functionality of purified Fabs to inhibit cdMMP-14 activity was tested by FRET assays. Typically, 1 µM of purified Fab was serially 2-fold diluted into assay buffer (50 mM Tris-HCl pH 7.5, 150 mM NaCl, 5 mM $CaCl_2$, 0.5 mM $ZnCl_2$), and incubated with 10 nM cdMMP-14 for 30 min at 4° C. The kinetic measurements were started with the addition of 1 µM M2350 peptide substrate (Bachem) and the fluorescence was monitored with excitation and emission wavelengths at 325 and 392 nm. To determine the type of inhibition Fabs were diluted to concentrations generating 70%, 50%, and 30% inhibition in HEPES assay buffer (50 mM HEPES pH 6.8, 150 mM NaCl, 5 mM $CaCl_2$, 0.5 mM $ZnCl_2$), and incubated with 10 nM cdMMP-14 at 4° C. for 30 min. For each Fab concentration, 50 µM to 2 mM FRET peptide substrates were added for kinetics measurements. Epitope mapping was performed by incubating 10 nM of each cdMMP-14 mutant with a gradient of 2 nM-5 µM R2C7 for 1 hour at room temperature before the addition of cdMMP-14 substrate and fluorescent monitoring as described above.

Gelatin Degradation Studies:

10 nM cdMMP-14 was incubated with 1 mg/mL gelatin (porcine skin, Sigma) in the absence or presence of 1 µM Fabs for 24 hours at room temperature, then samples were analyzed by 12% SDS-PAGE. A synthetic inhibitor GM6001 and a non-inhibitory Fab R2C17 were used as the positive and negative controls.

Results

Illumina Deep Sequencing of Long CDR-H3 Fab Libraries

Human Fab phage display libraries carrying CDR-H3 regions with 23, 25, and 27 aa in length were synthesized and subjected to three rounds of panning (R1, R2 and R3) against catalytic domain of MMP-14 (cdMMP-14) (Nam D. Generation of Highly Selective Monoclonal Antibodies Inhibiting Tumorigenic Proteases [dissertation]. [California]: University of California, Riverside). For each round, the bound phages were eluted by incubation with n-terminal domain of tissue inhibitors of metalloproteinases (n-TIMP-2), which is a native inhibitor of MMP-14 behaving in a competitive mode (Brew et al., 2000. Biochim Biophys Acta. 1477(1-2): 267-283). In principle, only the Fab phages directly interacting with the catalytic portion of MMP-14 or allosterically interfering n-TIMP-2 binding can be eluted off. Therefore, the combination of convex paratope library design with epitope-specific elution presumably results in enrichment of specific inhibitory antibodies. This hypothesis was partially confirmed by the panel of inhibitory Fabs isolated by ELISA screening in the previous study (Nam D. Generation of Highly Selective Monoclonal Antibodies Inhibiting Tumorigenic Proteases [dissertation]. [California]: University of California, Riverside). Aiming to fully understand the sequence landscape changes during the panning process and to systematically identify and characterize a large number of the most enriched antibody clones, libraries R1, R2, R3 and the original library before panning (Og) were subjected to Illumina NGS (FIG. 14). Briefly, Og, R1, R2, and R3 phagemids were purified, and their fragments encoding CDR-H3s with partial FR3 and FR4 regions were prepared by restriction digestion and direct ligation with custom-designed adapters for Illumina sequencing. This PCR free procedure should minimize the introduction of amplification bias, which is critical for frequency based antibody discovery (Ravn et al., 2010. Nucleic Acids Research. 38: e193; Ravn et al., 2013. Methods. 60(1): 99-110; Reddy et al., 2010. Nat Biotechnol. 28(9): 965-969; WO2011146514; US20110312505; EP2572203; CA2799746; CN201180035306; Zhua et al. 2013. Proc Natl Acad Sci USA. 110 (16): 6470-6475). RT-qPCR analysis showed that the assembled DNA samples had uniform melting temperatures, suggesting high quality and purity. The library DNA concentrations were quantified and the samples were multiplexed at a ratio of 10:1:1:1 (Og:R1:R2: R3) for sequencing. Analysis on an Agilent 2100 bioanalyzer further confirmed that the multiplexed DNA sample displayed sharp peaks associated with designed base pairs, indicating successful ligations with the flow cell adapters at both ends.

Sequencing raw data was de-multiplexed using unique indexes and processed in house to remove truncated and out of frame reads. Sequences either containing reading frame shifts due to sequencing errors or with low quality (quality scores less than 30) were excluded from further analysis. A total of $1.83 \times 10^6$, $1.09 \times 10^7$, $6.67 \times 10^6$, and $2.81 \times 10^5$ functional sequences were obtained for libraries Og, R1, R2, and R3 respectively, which accounted for 56-90% of the raw data (Table 4). Given that the library diversity usually decreased to $<10^5$ after the first round of biopanning, the Illumina results provided a considerable coverage and well represented the majority of R1, R2, and R3 library clones. The huge diversity ($1.25 \times 10^9$) of the original library cannot be fully covered in this study, however, the original library had yet to be enriched so full coverage is unnecessary.

TABLE 4

Statistics of deep sequencing results

|    | Raw Data   | In-Frame Full-Length CDR-H3s | In-Frame Full-Length/ Raw Data | Unique CDR-H3s | Unique/In-Frame Full-length | Frequency (copy numbers) of the most abundant clone |
|----|------------|------------------------------|--------------------------------|----------------|-----------------------------|-----------------------------------------------------|
| Og | 2,039,671  | 1,834,712                    | 89.95%                         | 1,834,576      | 99.99%                      | 0.000% (2)                                          |
| R1 | 19,488,812 | 10,941,297                   | 56.14%                         | 10,791,087     | 98.63%                      | 0.009% (981)                                        |
| R2 | 11,761,506 | 6,665,700                    | 56.67%                         | 6,229,221      | 93.45%                      | 0.129% (8600)                                       |
| R3 | 50,457     | 28,127                       | 55.74%                         | 19,906         | 70.77%                      | 1.888% (531)                                        |

Long CDR-H3s Enriched with Hydrophilic and Positively Charged Residues after Panning on MMP-14

As the most important region of antigen binding, CDR-H3s were focused for bioinformatics analysis (FIG. 14). Their sequences were recognized by using the signature motifs flanking N- and C-termini of CDR-H3s (Ravn et al., 2010. Nucleic Acids Research. 38: e193; Reddy et al., 2010. Nat Biotechnol. 28(9): 965-969). Analysis results indicated that the original library as expected, contained an even distribution of CDR-H3s with 23, 25, or 27 aa (30-37% each). Interestingly, after phage panning more than half of Fabs (58%) had 25 aa in their CDR-H3s, and the proportions of CDR-H3s with 23 or 27 aa decreased to 7 and 19% (FIG. 15A). Taking 25 aa CDR-H3s as an example, at each position of 92-100K, the Og library showed uniform usage of 20 amino acids, indicating constructed synthetic antibody libraries had high quality and well represented the diversity designs. During panning process, CDR-H3 amino acid usage distributions altered dramatically. Particularly, the average number of positively charged residues (Arg/His/Lys) steadily increased from 2.8 aa per CDR-H3 in Og to 3.3 in R1, 3.6 in R2, and finally 4.9 in R3 (FIG. 15B). This suggests the panning process enriched positively charged paratopes, which probably enhances interactions with the negatively charged MMP-14 catalytic cleft vicinity (Fernandez-Catalan et al., 1998. EMBO J. 17(17): 5238-5248). The usages of amino acids grouped according to physicochemical properties were further analyzed at individual residue positions of CDR-H3s. Results for CDR-H3s with 25 aa are shown in FIG. 15C, in which changes of 20% and more from Og to R3 are highlighted. Positively charged residues were enriched at positions 94, 99, 100, and 100C; proportions of negatively charged residues (Asp/Glu) increased at position 100I; polar residues (Ser/Thr/Asn/Gln) presented more at positions 92, 96, 97 and 100B; and hydrophobic residues (Ala/Ile/Leu/Met/Phe/Trp/Tyr/Val) presented less at position 96, 97, 99, 100C, 100D, 100I, and 100K. Overall, the increase of charged and hydrophilic residues with decrease of hydrophobic residues presumably improves Fab solubility, a phenomenon well documented in literatures (Nieba et al., 1997. Protein Eng. 10(4): 435-44; Lawrence M S, Phillips K J, Liu D R. 2007. Supercharging Proteins Can Impart Unusual Resilience. J Am Chem Soc 129: 10110-10112; Chiti et al., 2003. Nature. 424: 805-808).

Identification of Highly Abundant Fab Clones and Tracking their Enrichment Profiles After bioinformatics analysis of the entire libraries in general, individual Fab clones with the highest abundancies were identified for further studies. Limited by Illumina reading length capacity, the most diverse regions, CDR-H3s were chosen as the signature sequences to represent the associated Fabs in analysis, and the full VH and VL sequences of particular clones of interest were later recovered by PCR using specific primers (see, Table 6). For libraries Og, R1, R2 and R3, a total of $1.83 \times 10^6$, $1.08 \times 10^7$, $6.23 \times 10^6$, $1.99 \times 10^4$ different CDR-H3s were found (unique CDR-H3s, Table 4). The ratios between numbers of unique CDR-H3s over numbers of all in-frame full-length CDR-H3s in the associated library are 99.99% for Og, 96.63% for R1, 93.45% for R2 and 70.77% for R3. The copy numbers of each unique CDR-H3 sequences within R1, R2 and R3 were then counted, and their abundancies were calculated by dividing their copy numbers with the total number of functional CDR-H3s in that library. Results demonstrated that the most abundant clones in R1, R2, and R3 had frequencies of 0.009%, 0.129%, and 1.889% respectively, reflecting the quick enrichment progress during panning as expected. Because R1 enrichment was pre-mature, only R2 and R3 were used for Fab identification in the following analysis.

Due to the synthetic nature and relatively small dataset ($1.83 \times 10^6$) of Og library compared to constructed diversity ($1.25 \times 10^9$), majority of clones in Og presumably should have a single copy number. These results indeed indicated that 99.99% of Og CDR-H3s had a single copy, <0.01% CDR-H3s have two copies and there are no clones with more than two copies (Table 4). Consequently, the clones with the highest frequencies in R1, R2 or R3 are among the most enriched clones relative to Og, in which each clone has a low and even frequency. The 22 most abundant clones in R2 were identified with frequencies ranging from 0.13% to 0.02% (named as R2C1-R2C22 with their CDR-H3 sequences shown in Table 5). None of these 22 clones were present in Og (zero copies). In R1, the majority of these 22 clones had zero copies and only R2C3 and R2C19 had one copy.

Notably, the ranks and abundancies of these 22 clones in R3 were not always correlated with these in R2. More specifically, 15 clones such as R2C3, R2C4, and R2C6 exhibited further enrichments, i.e. a higher abundancy in R3 than R2. Because of this enrichment pattern, 7 of the 22 most abundant clones were discovered using traditional ELISA screening (Table 5) (Nam D. Generation of Highly Selective Monoclonal Antibodies Inhibiting Tumorigenic Proteases [dissertation]. [California]: University of California, Riverside). Clones R2C9, R2C10, and R2C17 displayed increased frequencies from Og to R1 and to R2, however their frequencies in R3 were similar to R2. These plateaus can be attributed to the balance between enrichment driven by panning and the depletion caused by slow cell growth. Interestingly, several top ranked clones in R2 such as R2C7, R2C18, and R2C22 showed declined frequencies in R3. As a consequence, these particular clones were not identified in ELISA screenings of R3 library, because of their low frequencies in R3 (<0.01% with rankings >10,000, Table 5).

Applying similar analysis, the 17 most abundant clones from R3 were also identified with frequencies ranging from 1.89% to 0.11%. For these 17 clones, 7 were not among the top 22 clones of R2. These 7 clones were named as R3Cx, in which x is the rank of that clone in R3. All R3Cx clones were not present in Og or R1, had relatively low frequencies in R2 (<0.01%), and quickly enriched in R3 (0.33-0.11%).

TABLE 5

In depth analysis of highly enriched clones from R2 and R3

| ID by NGS [1] | Sequence (CDR-H3 length) | % of R2 | % of R3 | Rank in R3 | Binding Affinity [2] | Inhibition potency | Yield (mg/L) |
|---|---|---|---|---|---|---|---|
| R2C1* | STAATTLSRMSRSYWTIQLPYGMDY (25) (SEQ ID NO: 25) | 0.13 | 1.89 | 1 | 590 nM | Non-Inhibitory | 1 |
| R2C2* | GVRGNKLRLLSSRSGLMESHYVMDY (25) (SEQ ID NO: 15) | 0.12 | 1.66 | 2 | 1.0 µM | 2.3 µM | 2 |
| R2C3* | PTTSRVNKKLFRVSVLHPGSYGMDY (25) (SEQ ID NO: 19) | 0.11 | 0.61 | 4 | 220 nM | 4.6 µM | 1 |
| R2C4 | GWRVYADRGHVRGYFRVWYGMDY (23) (SEQ ID NO: 29) | 0.10 | 0.53 | 3 | 10 µM** | 1.5 µM | 2 |
| R2C5 | IMKIKRNSLKFRGFVPLQMQYVMDY (25) (SEQ ID NO: 30) | 0.09 | 0.14 | 14 | 375 nM** | 50 nM | 3.5 |
| R2C6 | KDLLKTNRLTTRYKKSVSVGYGMDY (25) (SEQ ID NO: 31) | 0.07 | 0.53 | 5 | 2.4 µM | 2.4 µM | 1 |
| R2C7 | SCVWACCACRYWSGSDSHYAMDY (23) (SEQ ID NO: 32) | 0.06 | 0.01 | ~12500 | 153 nM | 100 nM | 1 |
| R2C8 | PGRHLQTTFKGYQFKYSRYIYAMDY (25) (SEQ ID NO: 33) | 0.05 | 0.16 | 12 | 1.2 µM | 1.2 µM | 3.5 |
| R2C9 | VLNIFMDVGAARFPGLVRYGMDY (23) (SEQ ID NO: 34) | 0.04 | 0.05 | ~4200 | 657 nM** | 80 nM | 0.75 |

TABLE 5 -continued

In depth analysis of highly enriched clones from R2 and R3

| ID by NGS [1] | Sequence (CDR-H3 length) | % of R2 | % of R3 | Rank in R3 | Binding Affinity [2] | Inhibition potency | Yield (mg/L) |
|---|---|---|---|---|---|---|---|
| R2C10 | MAKDFRILASVRMWVLASRLYVMDY (25) (SEQ ID NO: 35) | 0.04 | 0.03 | ~8400 | 360 nM | Non-Inhibitory | 0.5 |
| R2C11 | RYGSDVFCVGCFFGVRLSYVMDY (23) (SEQ ID NO: 36) | 0.03 | 0.03 | ~9100 | 750 nM | 600 nM | 0.75 |
| R2C12 | SDSWVQGRDFCYYSAWVGYGMDY (23) (SEQ ID NO: 37) | 0.03 | 0.05 | ~2600 | 150 nM | 150 nM | 0.5 |
| R2C13* | LYNGWLMVEGIGSAREGPTWYAMDY (25) (SEQ ID NO: 14) | 0.03 | 0.09 | 21 | 34 nM | 970 nM | <0.01 |
| R2C14 | VSNRYNRSSASIAGLQLFRPYGMDY (25) (SEQ ID NO: 38) | 0.03 | 0.05 | ~2600 | 1.2 µM** | 10 nM | 0.5 |
| R2C15* | SVHMKLSNKILSGWSWNNSFYAMDY (25) (SEQ ID NO: 16) | 0.03 | 0.07 | 28 | 460 nM | 3.9 µM | 2 |
| R2C16 | FKNADFAAGGQWSKMLIARMYAMDY (25) (SEQ ID NO: 39) | 0.03 | 0.10 | 17 | 1.8 µM | 5.5 µM | 2.4 |
| R2C17 | VGAWRVPSERMFTYPSARTRYAMDY (25) (SEQ ID NO: 40) | 0.03 | 0.02 | ~11000 | 2.1 µM | Non-Inhibitory | 0.4 |
| R2C18 | RDFGGFAGCLDGYVHVCWYAMDY (23) (SEQ ID NO: 41) | 0.02 | <0.01 | ~13000 | 430 nM | Non-Inhibitory | 0.5 |
| R2C19* | LDRDRYIHVGRAGNTYSNYYYVMDY (25) (SEQ ID NO: 22) | 0.03 | 0.17 | 11 | 9.7 nM | Non-Inhibitory | 0.5 |
| R2C20* | NFRVESAGRPGKTVLRKDGKYAMDY (25) (SEQ ID NO: 27) | 0.03 | 0.47 | 6 | 1.6 µM | Non-Inhibitory | 0.5 |
| R2C21 | LAWKSDNRGSFAKLQFTLKMYGMDY (25) (SEQ ID NO: 42) | 0.02 | 0.08 | 25 | Non-Binding** | 50 nM | 0.25 |
| R2C22 | HSRDGWQHWFGNWAGLHSYGMDY (23) (SEQ ID NO: 43) | 0.02 | <0.01 | ~13000 | 540 nM** | 75 nM | 0.15 |
| R3C7* | EIHMLSRQARYLRDGRRPRGSMYVMDY (27) (SEQ ID NO: 23) | 0.01 | 0.33 | 7 | 29 nM | Non-Inhibitory | 2 |
| R3C8 | HCLLRSRRCEMSTKTRELNVYRYAMDY (27) (SEQ ID NO: 44) | 0.01 | 0.30 | 8 | 1.3 µM | 5.4 µM | 1 |
| R3C9* | VKLQKDKSHQWIRNLVATPYGRYVMDY (27) (SEQ ID NO: 8) | 0.01 | 0.29 | 9 | 3.8 nM | 9.7 nM | 1 |
| R3C10 | GSLRRDFNLVVRSSWDIRSNYVMDY (25) (SEQ ID NO: 45) | <0.01 | 0.20 | 10 | 970 nM | 1.0 µM | 2 |
| R3C13 | WLRVSLKSGVYKVLARAVELDEYVMDY (27) (SEQ ID NO: 46) | 0.01 | 0.14 | 13 | 2.0 µM | 2.0 µM | 3 |
| R3C15 | GVRGNKLRLLSSRSGRMESHYVMDY (25) (SEQ ID NO: 47) | <0.01 | 0.14 | 15 | 57.5 nM | 170 nM | 4 |
| R3C16 | MASIDLRMLSRMLAGPQFKVYGMDY (25) (SEQ ID NO: 48) | 0.01 | 0.11 | 16 | Non-Binding** | 1.0 µM | 1 |

Notes:
[1] Clones were identified and ranked by their abundancies. Previously discovered Fabs by monoclonal phage ELISA are labeled as *.
[2] Fab genes were rescued by PCR and sub-cloned for expression. Purified Fabs were tested for binding affinity (by ELISA $EC_{50}$) and inhibition potency (by FRET $IC_{50}$). Fabs with EC50 >2 × $IC_{50}$ are labeled as **.

TABLE 6

Sequences for the light chain variable region (VL) and heavy chain variable region (VH) from each clone shown in Table 5.

| Clone Name | VH or VL Chain | Sequence |
|---|---|---|
| R2C4 | VH | EVQLVESGGGLVQPGGSLRLSCAASGFNLSYYYMHWVRQAPGKGLEWV AYISSYSGYTYYADSVKGRFTISADTSKNTAYLQMNSLRAEDTAVYYCAR GWRVYADRGHVRGYFRVWYGMDYWGQGTLVTVSSASTKGPSVFPLAPS SKSTSGGTAALGCLVKDYFPEPVTVSWNSGALTSGVHTFPAVLQSSGLYSL SSVVTVPSSSLGTQTYICNVNHKPSNTKVDKKVEPKSCDKTHT (SEQ ID NO: 89) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQGAGLITFGQGTKV EIKRTVAAPSVFIFPPSDSQLKSGTASVVCLLNNFYPREAKVQWKVDNALQ SGNSQESVTEQDSKDSTYSLSSTLTLSKADYEKHKVYACEVTHQGLSSPVT KSFNRGEC (SEQ ID NO: 90) |
| R2C5 | VH | EVQLVESGGGLVQPGGSLRLSCAASGFNLSSYYMHWVRQAPGKGLEWVA SIYPYSSYTSYADSVKGRFTISADTSKNTAYLQMNSLRAEDTAVYYCARIM KIKRNSLKFRGFVPLQMQYVMDYWGQGTLVTVSSASTKGPSVFPLAPSSK STSGGTAALGCLVKDYFPEPVTVSWNSGALTSGVHTFPAVLQSSGLYSLSS VVTVPSSSLGTQTYICNVNHKPSNTKVDKKVEPKSCDKTHT (SEQ ID NO: 91) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQSYGLFTFGQGTKV EIKRTVAAPSVFIFPPSDSQLKSGTASVVCLLNNFYPREAKVQWKVDNALQ SGNSQESVTEQDSKDSTYSLSSTLTLSKADYEKHKVYACEVTHQGLSSPVT KSFNRGEC (SEQ ID NO: 92) |
| R2C6 | VH | EVQLVESGGGLVQPGGSLRLSCAASGFNIYYSSMHWVRQAPGKGLEWVA YISPYYGYTSYADSVKGRFTISADTSKNTAYLQMNSLRAEDTAVYYCARK DLLKTNRLTTRYKKSVSVGYGMDYWGQGTLVTVSSASTKGPSVFPLAPSS KSTSGGTAALGCLVKDYFPEPVTVSWNSGALTSGVHTFPAVLQSSGLYSLS SVVTVPSSSLGTQTYICNVNHKPSNTKVDKKVEPKSCDKTHT (SEQ ID NO: 93) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQYVYPPFTFGQGTK VEIKRTVAAPSVFIFPPSDSQLKSGTASVVCLLNNFYPREAKVQWKVDNAL QSGNSQESVTEQDSKDSTYSLSSTLTLSKADYEKHKVYACEVTHQGLSSPV TKSFNRGEC (SEQ ID NO: 94) |
| R2C7 | VH | EVQLVESGGGLVQPGGSLRLSCAASGFNLSSSSMHWVRQAPGKGLEWVA SIYPYSGYTSYADSVKGRFTISADTSKNTAYLQMNSLRAEDTAVYYCARSC VWACCACRYWSGSDSHYAMDYWGQGTLVTVSSASTKGPSVFPLAPSSKS TSGGTAALGCLVKDYFPEPVTVSWNSGALTSGVHTFPAVLQSSGLYSLSSV VTVPSSSLGTQTYICNVNHKPSNTKVDKKVEPKSCDKTHT (SEQ ID NO: 95) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQSYHPLFTFGQGTK VEIKRTVAAPSVFIFPPSDSQLKSGTASVVCLLNNFYPREAKVQWKVDNAL QSGNSQESVTEQDSKDSTYSLSSTLTLSKADYEKHKVYACEVTHQGLSSPV TKSFNRGEC (SEQ ID NO: 96) |
| R2C8 | VH | EVQLVESGGGLVQPGGSLRLSCAASGFNISSSSIHWVRQAPGKGLEWVASI YPYYGSTSYADSVKGRFTISADTSKNTAYLQMNSLRAEDTAVYYCARPGR HLQTTFKGYQFKYSRYIYAMDYWGQGTLVTVSSASTKGPSVFPLAPSSKS TSGGTAALGCLVKDYFPEPVTVSWNSGALTSGVHTFPAVLQSSGLYSLSSV VTVPSSSLGTQTYICNVNHKPSNTKVDKKVEPKSCDKTHT (SEQ ID NO: 97) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQWGHHGYLITFGQG TKVEIKRTVAAPSVFIFPPSDSQLKSGTASVVCLLNNFYPREAKVQWKVDN ALQSGNSQESVTEQDSKDSTYSLSSTLTLSKADYEKHKVYACEVTHQGLSS PVTKSFNRGEC (SEQ ID NO: 98) |
| R2C9 | VH | EVQLVESGGGLVQPGGSLRLSCAASGFNIYSYSMHWVRQAPGKGLEWVA YIYPYSGYTYYADSVKGRFTISADTSKNTAYLQMNSLRAEDTAVYYCARV LNIFMDVGAARFPGLVRYGMDYWGQGTLVTVSSASTKGPSVFPLAPSSKS TSGGTAALGCLVKDYFPEPVTVSWNSGALTSGVHTFPAVLQSSGLYSLSSV VTVPSSSLGTQTYICNVNHKPSNTKVDKKVEPKSCDKTHT (SEQ ID NO: 99) |
| | VL | DIQMTQSPSSLSASVGDRVTITCRAGQDVSSAVAWYQQKPGKAPKLLIYSA STLHSGVPSRFSGSRSGTDFTLTISSLQPEDFATYYCQQSGPYSLFTFGQGTK VEIKRTVAAPSVFIFPP SDSQLKSGTASVVCLLNNFYPREAKVQWKVDNAL QSGNSQESVTEQDSKDSTYSLSSTLTLSKADYEKHKVYACEVTHQGLSSPV TKSFNRGEC (SEQ ID NO: 100) |

TABLE 6 -continued

Sequences for the light chain variable region (VL) and heavy chain variable region (VH) from each clone shown in Table 5.

| Clone Name | VH or VL Chain | Sequence |
|---|---|---|
| R2C11 | VH | EVQLVESGGGLVQPGGSLRLSCAASGFNLYYSSIHWVRQAPGKGLEWVA YIYPSYSYTYYADSVKGRFTISADTSKNTAYLQMNSLRAEDTAVYYCARR YGSDVFCVGCFFGVRLSYVMDYWGQGTLVTVSSASTKGPSVFPLAPSSKS TSGGTAALGCLVKDYFPEPVTVSWNSGALTSGVHTFPAVLQSSGLYSLSSV VTVPSSSLGTQTYICNVNHKPSNTKVDKKVEPKSCDKTHT (SEQ ID NO: 101) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQYVSSGSLITFGQGT KVEIKRTVAAPSVFIFPPSDSQLKSGTASVVCLLNNFYPREAKVQWKVDNA LQSGNSQESVTEQDSKDSTYSLSSTLTLSKADYEKHKVYACEVTHQGLSSP VTKSFNRGEC (SEQ ID NO: 102) |
| R2C12 | VH | EVQLVESGGGLVQPGGSLRLSCAASGFNISSSYMHWVRQAPGKGLEWVAS IYSYSSYTYYADSVKGRFTISADTSKNTAYLQMNSLRAEDTAVYYCARSD SWVQGRDFCYYSAWVGYGMDYWGQGTLVTVSSASTKGPSVFPLAPSSKS TSGGTAALGCLVKDYFPEPVTVSWNSGALTSGVHTFPAVLQSSGLYSLSSV VTVPSSSLGTQTYICNVNHKPSNTKVDKKVEPKSCDKTHT (SEQ ID NO: 103) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQGYYALFTFGQGTK VEIKRTVAAPSVFIFPPSDSQLKSGTASVVCLLNNFYPREAKVQWKVDNAL QSGNSQESVTEQDSKDSTYSLSSTLTLSKADYEKHKVYACEVTHQGLSSPV TKSFNRGEC (SEQ ID NO: 104) |
| R2C14 | VH | EVQLVESGGGLVQPGGSLRLSCAASGFNIYSSSIHWVRQAPGKGLEWVASI YSYSGYTYYADSVKGRFTISADTSKNTAYLQMNSLRAEDTAVYYCARVS NRYNRSSASIAGLQLFRPYGMDYWGQGTLVTVSSASTKGPSVFPLAPSSKS TSGGTAALGCLVKDYFPEPVTVSWNSGALTSGVHTFPAVLQSSGLYSLSSV VTVPSSSLGTQTYICNVNHKPSNTKVDKKVEPKSCDKTHT (SEQ ID NO: 105) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQSSYLITFGQGTKV EIKRTVAAPSVFIFPPSDSQLKSGTASVVCLLNNFYPREAKVQWKVDNALQ SGNSQESVTEQDSKDSTYSLSSTLTLSKADYEKHKVYACEVTHQGLSSPVT KSFNRGEC (SEQ ID NO: 106) |
| R2C16 | VH | EVQLVESGGGLVQPGGSLRLSCAASGFNIYSYSMHWVRQAPGKGLEWVA SISSYYGYTYYADSVKGRFTISADTSKNTAYLQMNSLRAEDTAVYYCARF KNADFAAGGQWSKMLIARMYAMDYWGQGTLVTVSSASTKGPSVFPLAPS SKSTSGGTAALGCLVKDYFPEPVTVSWNSGALTSGVHTFPAVLQSSGLYSL SSVVTVPSSSLGTQTYICNVNHKPSNTKVDKKVEPKSCDKTHT (SEQ ID NO: 107) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQYYSLITFGQGTKVE IKRTVAAPSVFIFPPSDSQLKSGTASVVCLLNNFYPREAKVQWKVDNALQS GNSQESVTEQDSKDSTYSLSSTLTLSKADYEKHKVYACEVTHQGLSSPVTK SFNRGEC (SEQ ID NO: 108) |
| R2C21 | VH | EVQLVESGGGLVQPGGSLRLSCAASGFNFSSSSIHWVRQAPGKGLEWVASI SSSYGYTYYADSVKGRFTISADTSKNTAYLQMNSLRAEDTAVYYCARLA WKSDNRGSFAKLQFTLKMYGMDYWGQGTLVTVSSASTKGPSVFPLAPSS KSTSGGTAALGCLVKDYFPEPVTVSWNSGALTSGVHTFPAVLQSSGLYSLS SVVTVPSSSLGTQTYICNVNHKPSNTKVDKKVEPKSCDKTHT (SEQ ID NO: 109) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQSVSWALFTFGQGT KVEIKRTVAAPSVFIFPPSDSQLKSGTASVVCLLNNFYPREAKVQWKVDNA LQSGNSQESVTEQDSKDSTYSLSSTLTLSKADYEKHKVYACEVTHQGLSSP VTKSFNRGEC (SEQ ID NO: 110) |
| R2C22 | VH | EVQLVESGGGLVQPGGSLRLSCAASGFNIYSSYMHWVRQAPGKGLEWVA SIYSSYGSTYYADSVKGRFTISADTSKNTAYLQMNSLRAEDTAVYYCARH SRDGWQHWFGNWAGLHSYGMDYWGQGTLVTVSSASTKGPSVFPLAPSS KSTSGGTAALGCLVKDYFPEPVTVSWNSGALTSGVHTFPAVLQSSGLYSLS SVVTVPSSSLGTQTYICNVNHKPSNTKVDKKVEPKSCDKTHT (SEQ ID NO: 111) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQYYHYGYYLITFGQ GTKVEIKRTVAAPSVFIFPPSDSQLKSGTASVVCLLNNFYPREAKVQWKVD NALQSGNSQESVTEQDSKDSTYSLSSTLTLSKADYEKHKVYACEVTHQGL SSPVTKSFNRGEC (SEQ ID NO: 112) |

TABLE 6 -continued

Sequences for the light chain variable region (VL) and heavy chain variable region (VH) from each clone shown in Table 5.

| Clone Name | VH or VL Chain | Sequence |
|---|---|---|
| R3C8 | VH | EVQLVESGGGLVQPGGSLRLSCAASGFNFSSSSIHWVRQAPGKGLEWVASI YPSYSYTYYADSVKGRFTISADTSKNTAYLQMNSLRAEDTAVYYCARHCL LRSRRCEMSTKTRELNVYRYAMDYWGQGTLVTVSSASTKGPSVFPLAPSS KSTSGGTAALGCLVKDYFPEPVTVSWNSGALTSGVHTFPAVLQSSGLYSLS SVVTVPSSSLGTQTYICNVNHKPSNTKVDKKVEPKSCDKTHT (SEQ ID NO: 113) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQWPVGSSYPITFGQG TKVEIKRTVAAPSVFIFPPSDSQLKSGTASVVCLLNNFYPREAKVQWKVDN ALQSGNSQESVTEQDSKDSTYSLSSTLTLSKADYEKHKVYACEVTHQGLSS PVTKSFNRGEC (SEQ ID NO: 114) |
| R3C10 | VH | EVQLVESGGGLVQPGGSLRLSCAASGFNIYYSSMHWVRQAPGKGLEWVA SISPYYGYTYYADSVKGRFTISADTSKNTAYLQMNSLRAEDTAVYYCARG SLRRDFNLVVRSSWDIRSNYVMDYWGQGTLVTVSSASTKGPSVFPLAPSS KSTSGGTAALGCLVKDYFPEPVTVSWNSGALTSGVHTFPAVLQSSGLYSLS SVVTVPSSSLGTQTYICNVNHKPSNTKVDKKVEPKSCDKTHT (SEQ ID NO: 115) |
| | VL | DIQMTQSP SSLSASVGDRVTITCRASQSVSSAVAWYQQKPGKAPKLLIYSA SSLYSGVPSRFSGSRSGTDFTLTISSLQPEDFATYYCQQSWPYPITFGQGTK VEIKRTVAAPSVFIFPPSDSQLKSGTASVVCLLNNFYPREAKVQWKVDNAL QSGNSQESVTEQDSKDSTYSLSSTLTLSKADYEKHKVYACEVTHQGLSSPV TKSFNRGEC (SEQ ID NO: 116) |
| R3C13 | VH | EVQLVESGGGLVQPGGSLRLSCAASGFNIYYSYMHWVRQAPGKGLEWVA SISSYSGSTSYADSVKGRFTISADTSKNTAYLQMNSLRAEDTAVYYCARWL RVSLKSGVYKVLARAVELDEYVMDYWGQGTLVTVSSASTKGPSVFPLAP SSKSTSGGTAALGCLVKDYFPEPVTVSWNSGALTSGVHTFPAVLQSSGLYS LSSVVTVPSSSLGTQTYICNVNHKPSNTKVDKKVEPKSCDKTHT (SEQ ID NO: 117) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQSGYYAWPITFGQG TKVEIKRTVAAPSVFIFPPSDSQLKSGTASVVCLLNNFYPREAKVQWKVDN ALQSGNSQESVTEQDSKDSTYSLSSTLTLSKADYEKHKVYACEVTHQGLSS PVTKSFNRGEC (SEQ ID NO: 118) |
| R3C15 | VH | EVQLVESGGGLVQPGGSLRLSCAASGFNISYSYMHWVRQAPGKGLEWVA SISPYSGYTYYADSVKGRFTISADTSKNTAYLQMNSLRAEDTAVYYCARG VRGNKLRLLSSRSGRMESHYVMDYWGQGTLVTVSSASTKGPSVFPLAPSS KSTSGGTAALGCLVKDYFPEPVTVSWNSGALTSGVHTFPAVLQSSGLYSLS SVVTVPSSSLGTQTYICNVNHKPSNTKVDKKVEPKSCDKTHT (SEQ ID NO: 119) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQAGSLFTFGQGTKV EIKRTVAAPSVFIFPPSDSQLKSGTASVVCLLNNFYPREAKVQWKVDNALQ SGNSQESVTEQDSKDSTYSLSSTLTLSKADYEKHKVYACEVTHQGLSSPVT KSFNRGEC (SEQ ID NO: 120) |
| R3C16 | VH | EVQLVESGGGLVQPGGSLRLSCAASGFNLYYSYMHWVRQAPGKGLEWV ASISPYSSSTSYADSVKGRFTISADTSKNTAYLQMNSLRAEDTAVYYCARM ASIDLRMLSRMLAGPQFKVYGMDYWGQGTLVTVSSASTKGPSVFPLAPSS KSTSGGTAALGCLVKDYFPEPVTVSWNSGALTSGVHTFPAVLQSSGLYSLS SVVTVPSSSLGTQTYICNVNHKPSNTKVDKKVEPKSCDKTHT (SEQ ID NO: 121) |
| | VL | DIQMTQSPSSLSASVGDRVTITCRASQSVSSAVAWYQQKPGKAPKLLIYSA SSLYSGVPSRFSGSRSGTDFTLTISSLQPEDFATYYCQQYYSYSSLITFGQGT KVEIKRTVAAPSVFIFPPSDSQLKSGTASVVCLLNNFYPREAKVQWKVDNA LQSGNSQESVTEQDSKDSTYSLSSTLTLSKADYEKHKVYACEVTHQGLSSP VTKSFNRGEC (SEQ ID NO: 122) |

Gene Rescue and Protein Production for Abundant Fabs

Fab genes of these 29 top ranked clones (22 from R2 and 7 from R3) were specifically amplified from their respective libraries by PCR using a universal forward primer recognizing N-terminal of the VL and a clone specific reverse primer recognizing unique CDR-H3 s. After secondary extension PCR to introduce a restriction site at the C-terminal of VH, the VL-CL-VH fragments were sub-cloned into a Fab expression plasmid. Successful gene extraction and cloning were confirmed by Sanger sequencing. The Fabs were produced in the periplasmic space of E. coli with typical yields of 0.5-2.0 mg purified proteins per litter of culture medium (Table 5). Most top ranked clones in particular were highly expressed compared to lower ranked ones, suggesting expression level affected enrichment progress during phage panning. Purified Fabs remained stable and functional at room temperature for at least 24 hours.

Discovery of a Panel of Inhibitory Fabs with High Selectivity

Figure 16:
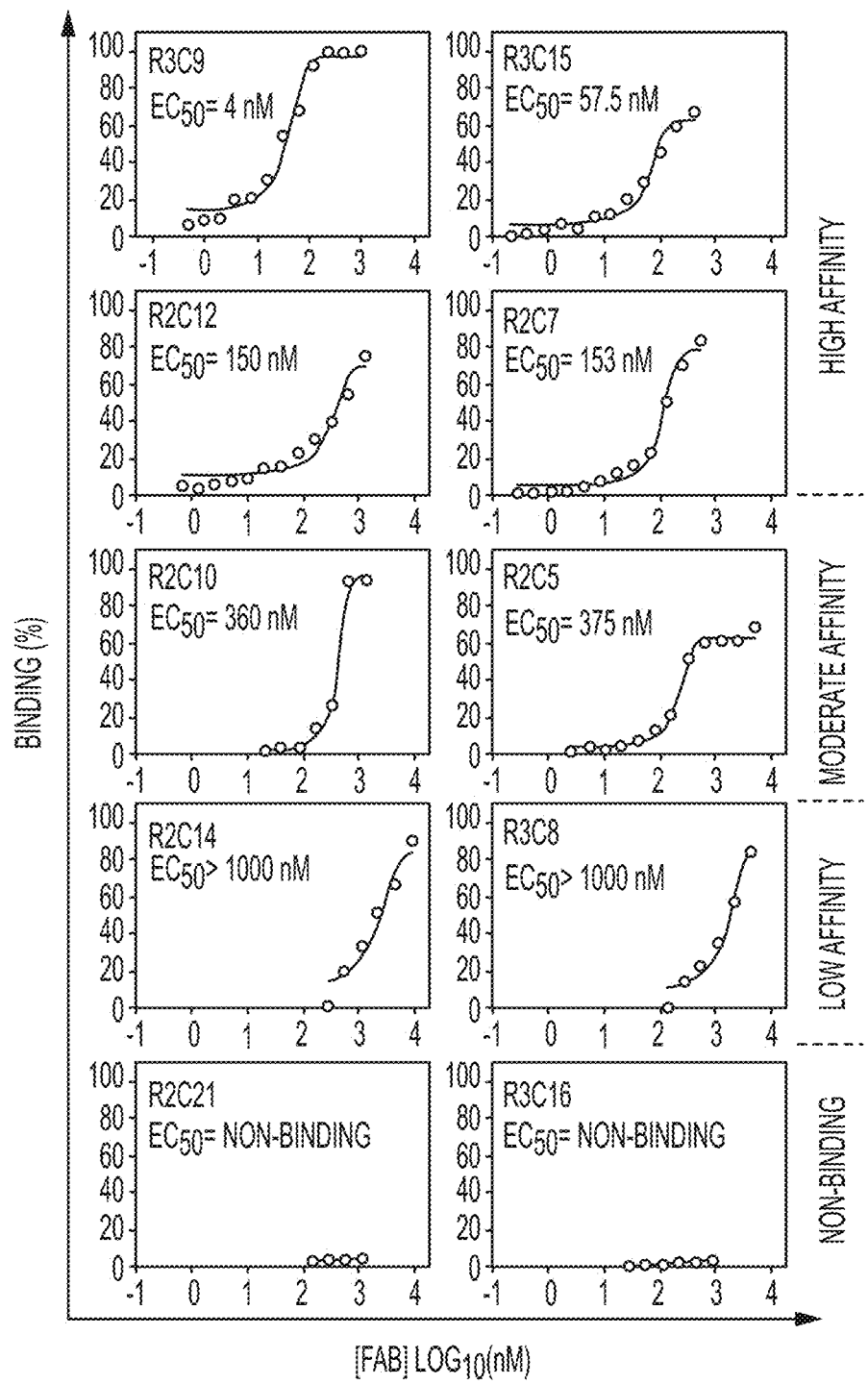
FIG. 16. Fab binding affinities measured by ELISA. ELISA studies were performed by reacting purified Fabs with immobilized cdMMP-14 followed by tagging with anti-Fab-HRP. Color was then developed by the addition of TMB and read on a spectrophotometer. A range of binding strengths from 4 nM to 10 µM was found, which is expected from a synthetic antibody library.

The binding affinities of purified Fabs were measured by ELISA and results indicated that majority of highly abundant clones (27/29) exhibited binding specificity to cdMMP- 14 with $EC_{50}$ values ranging from 4 nM to 3 µM (Table 5, FIG. 16). Among them, eight Fabs R2C1, R2C3, R2C12, R2C13, R2C19, R3C7, R3C9, R3C15 had relatively high affinities at 4-150 nM; five Fabs R2C5, R2C7, R2C10, R2C15, and R2C18 exhibited moderate affinities at 150-500 nM; and 14 other Fabs showed weak binding with $EC_{50}$ values at 0.5-3 µM. Given these Fabs were isolated from synthetic phage libraries, a broad range of affinities was expected.

Figure 17:
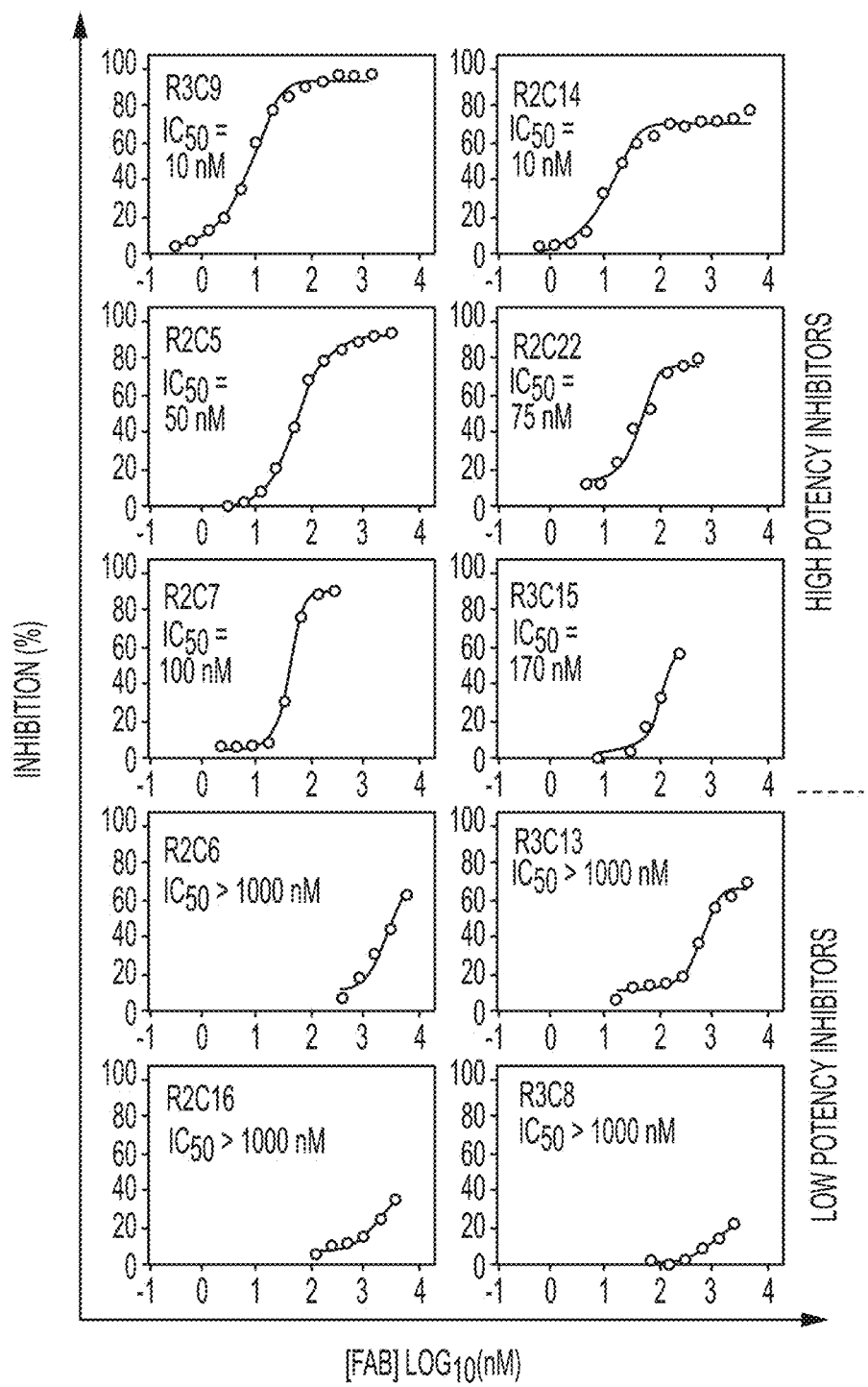
FIG. 17. Potencies of inhibitory Fabs by FRET assays. FRET assays were performed by reacting the purified Fabs with cdMMP-14 for 30 min then adding FRET peptide substrate. The increase in fluorescence was monitored for 1 hour to determine inhibitory function. A variety of inhibitory clones with potencies ranging from 10 nM to 8.0 µM was found.

More importantly, inhibition functions of the purified Fabs on cdMMP-14 were examined using a FRET peptide substrate to derive $IC_{50}$ curves (FIG. 17). Of the 29 highly abundant Fab clones identified from R2 and R3, 20 exhibited inhibition with $IC_{50}$ values ranging from 10 nM to 4 µM. Particularly, R2C14 and R3C9 had an inhibition potency of 10 nM; eight Fabs R2C5, R2C7, R2C9, R2C12, R2C13, R2C21, R2C22 and R3C15 exhibited inhibition potencies at 50-200 nM; and 10 other Fabs had weak inhibition with $IC_{50}$ 600 nM-4 µM.

Figure 18:
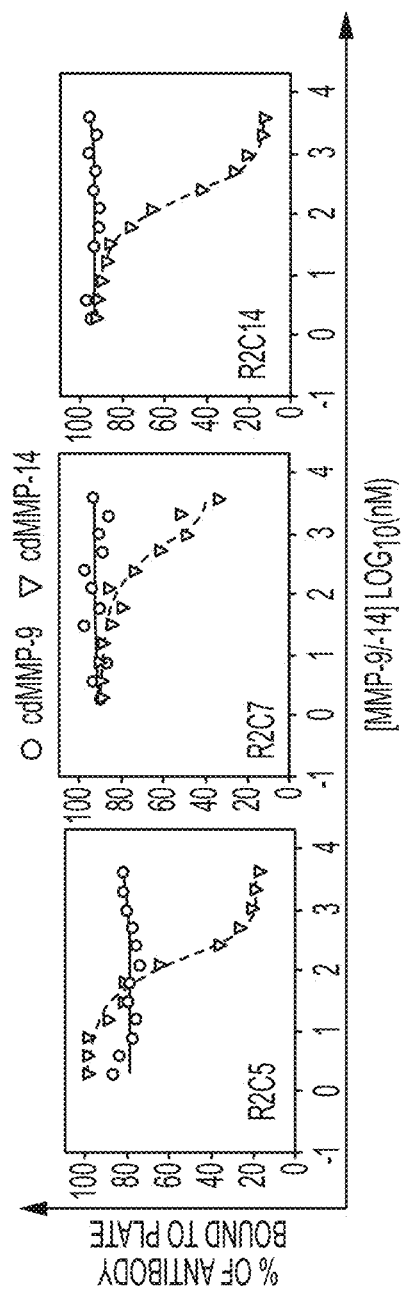
FIG. 18. Specificity tests by competitive ELISA. Fabs at their respective $IC_{50}$ concentrations were incubated with varying concentrations of cdMMP-9 or cdMMP-14 then added to ELISA plates coated with 100 nM cdMMP-14. Fabs bound to the cdMMP-14 on plates, even at high concentrations of cdMMP-9, indicating there are no interactions between Fabs and cdMMP-9. As the control experiments, when incubating with cdMMP-14 in solution, Fabs transferred from the plate to the solution as the concentration of cdMMP-14 in solution increased.

Three Fabs R2C5, R2C7, and R2C14 of high and moderate inhibition potencies (10-100 nM) but not found by ELISA screening in previous study were tested for their binding selectivity to cdMMP-14 over highly homologous cdMMP-9. Tests were performed by incubating Fabs at their $IC_{50}$ concentrations with varying concentrations of cdMMP-9 or cdMMP-14 then adding to an ELISA plate coated with streptavidin and biotinylated cdMMP-14. Fabs R2C5, R2C7 and R2C14 bound to cdMMP-14 on the plate even with high concentrations of cdMMP-9 in solution, indicating no interactions with cdMMP-9 (FIG. 18). While in control experiments, the amounts of Fabs binding to immobolized cdMMP-14 responded to concentrations of cdMMP-14 in solution as expected. Therefore, Fabs R2C5, R2C7 and R2C14 exhibited high selectivity to cdMMP-14. A further zymography test of Fab R2C7 demonstrated that it inhibited cdMMP-14 from degrading gelatin.

Inhibition Mechanism of R2C7

Figure 19B:
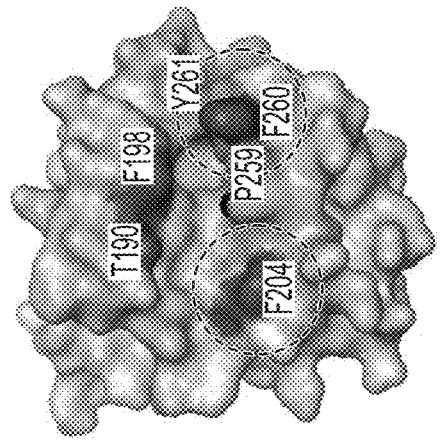
FIGS. 19A-D. Inhibition mechanism of R2C7.
Figure 19D:
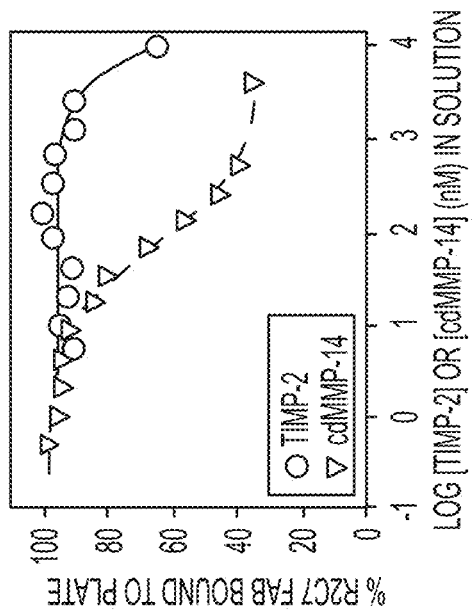
Figure 19A:
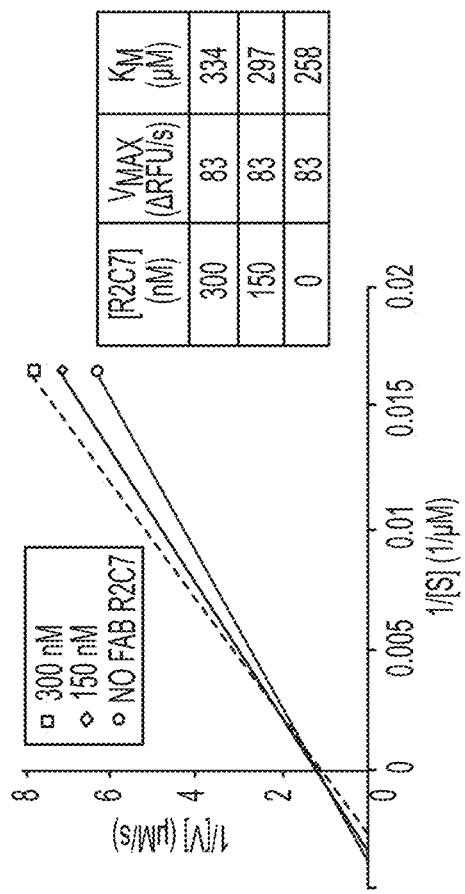

To determine the type of inhibition, a series of enzymatic activity assays in the presence of 0, 150, and 300 nM Fab R2C7 were performed. The obtained Lineweaver-Burk plots demonstrate an unchanged turnover rate ($V_{max}$) and an increased Michaelis constant ($K_m$) when Fab concentration was raised, indicating a competitive inhibition mode (FIG. 19A). Competitive ELISA with increased concentrations of n-TIMP-2 resulted in decreased amounts of Fab R2C7 bound to immobilized cdMMP-14 (FIG. 19B), suggesting that R2C7 and n-TIMP-2 directly competed on binding to cdMMP-14, and presumably their epitopes were at least partially overlapping. As the control experiments, when incubating with cdMMP-14 in solution, Fabs transferred from the solution to the plate as the concentration of cdMMP-14 in solution decreased to ~10 nM.

Figure 19C:
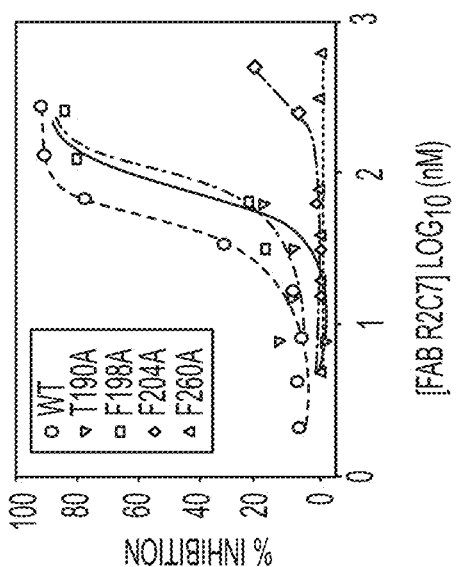

To further determine whether R2C7 is a direct or allosteric competitive inhibitor, binding site of Fab R2C7 was studied by alanine scanning mutagenesis of MMP-14. Four residue positions around reaction pocket of cdMMP-14 (T190A, F198A, F204A, and F260A) were selected for Ala substitution, and these cdMMP-14 mutants were prepared by periplasmic expression without refolding (Nam D, Ge X. 2015. *Biotechnol. Bioeng.* 113(4):717-23). Inhibition assays with FRET peptide substrate indicated that R2C7 lost its inhibition ability toward cdMMP-14 mutants F204A and F260A, while keeping the same level of inhibition potency toward T190A and F198A as wild type cdMMP-14 (FIG. 19C). Notably, F204 and F260 are responsible for the formation of a relatively deep S1' site of MMP-14 among MMP family (Chiti et al., 2003. *Nature*. 424: 805-808; Nagase H. 2001. Substrate Specificity of MMPs. Cancer Drug Discovery and Development. In: Clendeninn N J and Appelt K, editor. Matrix Metalloproteinase Inhibitors in Cancer Therapy. Springer. p 39-66), suggesting R2C7 binds to the reaction pocket vicinity of cdMMP-14 directly (FIG. 19D).

Discussion

The use of next generation high-throughput sequencing technologies on rounds of selected libraries is a powerful method for the identification of unique inhibitory clones. In conjugation with convex paratope antibody library design, an n-TIMP-2 elution method was used during the phage panning process to enrich the libraries in competitive inhibitory clones. Traditional ELISA screenings were performed on the third round panned library by randomly picking individual colonies. This method resulted in the discovery of some of the most abundant clones in R3, as well as a few random clones that were not necessarily abundant but nonetheless picked. One limitation with ELISA screening is that some clones enriched in R2 but declined in R3 will most likely be missed. For example, the seventh most abundant clone in R2, R2C7 is ranked ~12500 in R3 with a frequency of 0.01%. Clones such as R2C7 (with an inhibition potency of 100 nM), are valuable candidates for further development but are depleted in continual rounds of panning. Applying ELISA on R2 is not realistic either, because even the most enriched clones in R2 had a frequency of ~1/1000. Low abundancies and the large diversity of R2 make the likelihood of discovery relatively low. By NGS, laborious ELISA screenings is avoided and all enriched clones with their abundancies above the background can be identified and tracked along rounds of the panning process. Using this approach, many specific clones with high inhibition potencies, such as R2C7, R2C9, R2C12, and R2C22, were successfully discovered. In fact, 15 of 20 identified inhibitory Fabs were not found by ELISA, demonstrating the power of NGS.

All of the 29 highly abundant clones identified from R2 and R3 have zero copies in Og. Therefore their frequencies in R2 and R3 can be directly used to reflect their enrichment over Og. By tracking their frequencies during phage panning process, three patterns were found—rise, plateau, and decline (Table 5). The observed different enrichment and depletion patterns occur because phage panning is a multi-step process involving cell growth, Fab expression and display, and competitive binding. Suboptimal conditions at any of these steps can result in a decrease of abundancy. For example, an individual clone that grows slowly will be overtaken and gradually phased out by its faster growing competitors. This effect has nothing to do with the strength of the antibody, however it will still result in the stagnation or depletion of the clone relative to the total library in subsequent rounds of panning. Another major concern during the phage ELISA selection process is low expression levels of antibody molecules. A clone that binds strongly, but does not express well may not have a high enough signal to be selected; this results in the loss of the clone. Finally, individual clones will compete for binding sites on the bound MMP-14. This results in the loss of weaker binding yet potentially inhibitory clones.

Figure 20:
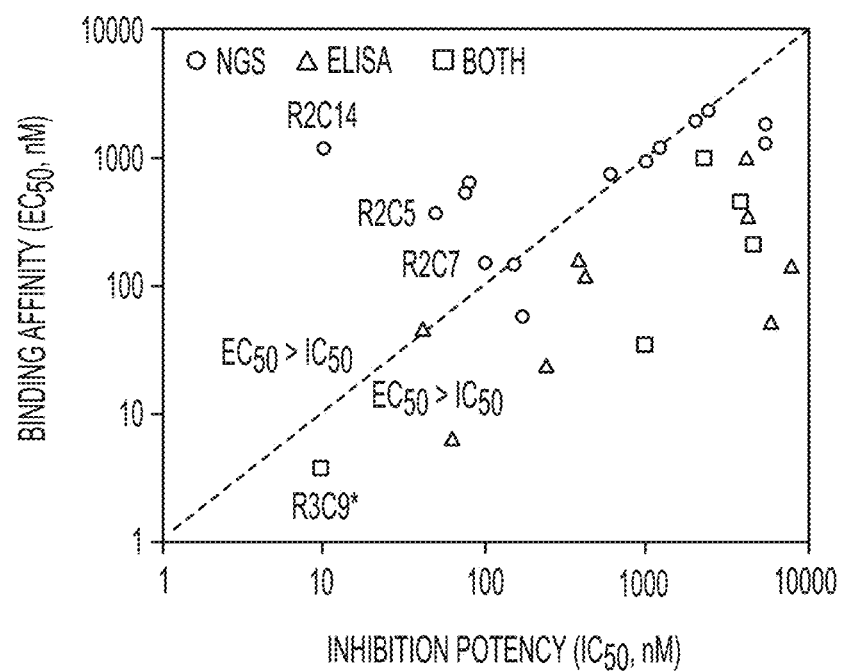
FIG. 20. Relationship between binding affinity and inhibition potency comparing the results from NGS (circles) and phage ELISA (triangles). The clones found by both methods are also shown (squares). The diagonal dashed line represents equal $EC_{50}$ and $IC_{50}$ values.

The 20 MMP-14 binding Fabs identified by ELISA in previous study were also tracked to monitor their enrichment profiles. As results show, 9 of the 20 clones were among the most abundant 29 clones identified by NGS. However, the remaining 11 clones have frequencies less than 0.01% in R2 and less than 0.05% in R3, thus are unlikely to be discovered by NGS and bioinformatics. FIG. 20 shows the correlations between binding affinity (EC$_{50}$) and inhibition potency (IC$_{50}$) of all the identified clones by either ELISA, or NGS or both methods. Overall, this chart clearly demonstrated that applying deep sequencing together with traditional ELISA serves as a powerful and practical strategy for efficient recovery of specific mAbs, consistent with others conclusion (Ravn et al., 2010. Nucleic Acids Research. 38: e193; Ravn et al., 2013. Methods. 60(1): 99-110). The large number of inhibitory clones yields many options for further engineering to improve affinity and potency. Notably, a few inhibitory Fabs, e.g. R2C5 and R2C14, exhibited higher inhibition IC$_{50}$ values than affinity EC$_{50}$ values. A likely explanation of this phenomenon is that these Fabs are suicide inhibitors and are slowly cleaved by high concentrations of cdMMP-14 (Farady et al., 2007. J Mol Biol. 369(4):1041-1051). Analysis of the theoretical cut sites of MMP-14, i.e. usually containing a positively charged residue at the P4 position and a hydrophobic residue at the P1' position, can guide future studies on site-specific mutagenesis to engineer cleavage resistant mAbs (Kridel et al., 2002. J Biol Chem. 26: 23788-23793).

Avoiding sequencing artifacts is critical for the success of frequency-based antibody discovery. PCR often introduces bias due to the differential amplification of some DNA templates over others. In this study, sequencing adapters were custom-designed for direct ligation with antibody CDR-H3 fragments prepared by phagemid extraction and restriction digestion. This procedure without amplification presumably minimized quantification biases caused by PCR.

In conclusion, combination of the convex paratope antibody library design with next-generation deep sequencing of panned libraries allowed us to identify a panel of highly potent and highly selective Fabs inhibiting cdMMP-14 not found by ELISA. Particularly, Fab R2C7 exhibited 100 nM inhibition potency by binding to the catalytic cleft vicinity of cdMMP-14. In addition to R2C7, several potent inhibitory Fabs e.g. R2C5 and R2C14, with IC$_{50}$ values at 10-50 nM with excellent selectivity were also isolated. And Fabs R2C5, R2C9, R2C12, R3C15 were found to be competitive inhibitors as well. This panel of inhibitory Fabs provides us a rich pool of lead candidates for further selection of suitable epitopes for therapeutics and optimization of pharmacological properties through affinity maturation and solubility/stability improvement. Besides MMP-14, several other MMP family members have been recognized playing important roles in variety of indications, therefore the methodology demonstrated in the current study can be readily applied for the generation of highly potent inhibitory mAbs targeting other MMPs of physiological significance. These highly selective inhibitors can also been used as research tools for better understanding of the not well-defined network of MMPs with their substrates.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An anti-MMP-14 antibody, or a fragment thereof, comprising:
   1) a $V_H$ comprising SEQ ID NO:49; and a $V_L$ comprising SEQ ID NO:50;
   2) a $V_H$ comprising SEQ ID NO:51; and a $V_L$ comprising SEQ ID NO:52;
   3) a $V_H$ comprising SEQ ID NO:53; and a $V_L$ comprising SEQ ID NO:54;
   4) a $V_H$ comprising SEQ ID NO:55; and a $V_L$ comprising SEQ ID NO:56;
   5) a $V_H$ comprising SEQ ID NO:57; and a $V_L$ comprising SEQ ID NO:58;
   6) a $V_H$ comprising SEQ ID NO:59; and a $V_L$ comprising SEQ ID NO:60;
   7) a $V_H$ comprising SEQ ID NO:63; and a $V_L$ comprising SEQ ID NO:64;
   8) a $V_H$ comprising SEQ ID NO:67; and a $V_L$ comprising SEQ ID NO:68;
   9) a $V_H$ comprising SEQ ID NO:69; and a $V_L$ comprising SEQ ID NO:70;
   10) a $V_H$ comprising SEQ ID NO:71; and a $V_L$ comprising SEQ ID NO:72;
   11) a $V_H$ comprising SEQ ID NO:73; and a $V_L$ comprising SEQ ID NO:74;
   12) a $V_H$ comprising SEQ ID NO:75; and a $V_L$ comprising SEQ ID NO:76;
   13) a $V_H$ comprising SEQ ID NO:77; and a $V_L$ comprising SEQ ID NO:78;
   14) a $V_H$ comprising SEQ ID NO:81; and a $V_L$ comprising SEQ ID NO:82;
   15) a $V_H$ comprising SEQ ID NO:89; and a $V_L$ comprising SEQ ID NO:90;
   16) a $V_H$ comprising SEQ ID NO:91; and a $V_L$ comprising SEQ ID NO:92;
   17) a $V_H$ comprising SEQ ID NO:93; and a $V_L$ comprising SEQ ID NO:94;
   18) a $V_H$ comprising SEQ ID NO:95; and a $V_L$ comprising SEQ ID NO:96;
   19) a $V_H$ comprising SEQ ID NO:97; and a $V_L$ comprising SEQ ID NO:98;
   20) a $V_H$ comprising SEQ ID NO:99; and a $V_L$ comprising SEQ ID NO:100;
   21) a $V_H$ comprising SEQ ID NO:101; and a $V_L$ comprising SEQ ID NO:102;
   22) a $V_H$ comprising SEQ ID NO:103; and a $V_L$ comprising SEQ ID NO:104;
   23) a $V_H$ comprising SEQ ID NO:105; and a $V_L$ comprising SEQ ID NO:106;
   24) a $V_H$ comprising SEQ ID NO:107; and a $V_L$ comprising SEQ ID NO:108;
   25) a $V_H$ comprising SEQ ID NO:111; and a $V_L$ comprising SEQ ID NO:112;
   26) a $V_H$ comprising SEQ ID NO:113; and a $V_L$ comprising SEQ ID NO:114;
   27) a $V_H$ comprising SEQ ID NO:115; and a $V_L$ comprising SEQ ID NO:116;
   28) a $V_H$ comprising SEQ ID NO:117; and a $V_L$ comprising SEQ ID NO:118; or
   29) a $V_H$ comprising SEQ ID NO:119; and a $V_L$ comprising SEQ ID NO:120.

2. The anti-MMP-14 antibody of claim 1, or a fragment thereof, comprising:
   1) a $V_H$ comprising SEQ ID NO:49; and a $V_L$ comprising SEQ ID NO:50;
   2) a $V_H$ comprising SEQ ID NO:57; and a $V_L$ comprising SEQ ID NO:58; or
   3) a $V_H$ comprising SEQ ID NO:59; and a $V_L$ comprising SEQ ID NO:60.

3. The anti-MMP-14 antibody of claim 2, or a fragment thereof, comprising a $V_H$ comprising SEQ ID NO:49; and a $V_L$, comprising SEQ ID NO:50.

4. The anti-MMP-14 antibody of claim 2, or a fragment thereof, comprising a $V_H$ comprising SEQ ID NO:57; and a $V_L$, comprising SEQ ID NO:58.

5. The anti-MMP-14 antibody of claim 2, or a fragment thereof, comprising a $V_H$ comprising SEQ ID NO:59; and a $V_L$, comprising SEQ ID NO:60.

6. The anti-MMP-14 antibody or fragment thereof, of claim 1, which is an antibody fragment.

7. The anti-MMP-14 antibody or fragment thereof, of claim 1, which is a Fab, F(ab')$_2$, Fv, single-chain Fv (scFv), diabody (diabodies), linear antibody or a multispecific antibody prepared from an antibody fragment.

8. A composition comprising an anti-MMP-14 antibody, or fragment thereof, as described in claim 1 and physiologically-acceptable, non-toxic carrier.

9. A kit comprising an anti-MMP-14 antibody, or a fragment thereof, as described in claim 1, packaging material, and instructions for administering the antibody, or a fragment thereof, to a mammal.

* * * * *

SEQUENCE LISTING

```
<160> NUMBER OF SEQ ID NOS: 135

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid

<400> SEQUENCE: 1

His Glu Xaa Xaa His Xaa Xaa Gly Xaa Xaa His
1               5                   10

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggccgtttca ctataagcgc agacacatcc aaaaacacag cctacctgca gatgaacagc       60
```

```
<210> SEQ ID NO 3
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5'-phosphorylated
<220> FEATURE:
<221> NAME/KEY: modified_base
<222> LOCATION: (21)..(74)
<223> OTHER INFORMATION: a, c, t or g
<220> FEATURE:
<221> NAME/KEY: modified_base
<222> LOCATION: (80)..(80)
<223> OTHER INFORMATION: a, c, t or g
<220> FEATURE:
<223> OTHER INFORMATION: See specification as filed for detailed
      description of substitutions and preferred embodiments

<400> SEQUENCE: 3
ccgtgtatta ttgcgcgcgt nnnnnnnnnn nnnnnnnnnn nnnnnnnnnn nnnnnnnnnn      60
nnnnnnnnnn nnnntatgbn atggactact ggggtcaggg                          100

<210> SEQ ID NO 4
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5'-phosphorylated
<220> FEATURE:
<221> NAME/KEY: modified_base
<222> LOCATION: (21)..(22)
<223> OTHER INFORMATION: a, c, t or g
<220> FEATURE:
<221> NAME/KEY: modified_base
<222> LOCATION: (24)..(25)
<223> OTHER INFORMATION: a, c, t or g
<220> FEATURE:
<221> NAME/KEY: modified_base
<222> LOCATION: (27)..(28)
<223> OTHER INFORMATION: a, c, t or g
<220> FEATURE:
<221> NAME/KEY: modified_base
<222> LOCATION: (30)..(31)
<223> OTHER INFORMATION: a, c, t or g
<220> FEATURE:
<221> NAME/KEY: modified_base
<222> LOCATION: (33)..(34)
<223> OTHER INFORMATION: a, c, t or g
<220> FEATURE:
<221> NAME/KEY: modified_base
<222> LOCATION: (36)..(37)
<223> OTHER INFORMATION: a, c, t or g
<220> FEATURE:
<221> NAME/KEY: modified_base
<222> LOCATION: (39)..(40)
<223> OTHER INFORMATION: a, c, t or g
<220> FEATURE:
<221> NAME/KEY: modified_base
<222> LOCATION: (42)..(43)
<223> OTHER INFORMATION: a, c, t or g
<220> FEATURE:
<221> NAME/KEY: modified_base
<222> LOCATION: (45)..(46)
<223> OTHER INFORMATION: a, c, t or g
<220> FEATURE:
<221> NAME/KEY: modified_base
<222> LOCATION: (48)..(49)
<223> OTHER INFORMATION: a, c, t or g
<220> FEATURE:
```

```
<221> NAME/KEY: modified_base
<222> LOCATION: (51)..(52)
<223> OTHER INFORMATION: a, c, t or g
<220> FEATURE:
<221> NAME/KEY: modified_base
<222> LOCATION: (54)..(55)
<223> OTHER INFORMATION: a, c, t or g
<220> FEATURE:
<221> NAME/KEY: modified_base
<222> LOCATION: (57)..(58)
<223> OTHER INFORMATION: a, c, t or g
<220> FEATURE:
<221> NAME/KEY: modified_base
<222> LOCATION: (60)..(61)
<223> OTHER INFORMATION: a, c, t or g
<220> FEATURE:
<221> NAME/KEY: modified_base
<222> LOCATION: (63)..(64)
<223> OTHER INFORMATION: a, c, t or g
<220> FEATURE:
<221> NAME/KEY: modified_base
<222> LOCATION: (66)..(67)
<223> OTHER INFORMATION: a, c, t or g
<220> FEATURE:
<221> NAME/KEY: modified_base
<222> LOCATION: (69)..(70)
<223> OTHER INFORMATION: a, c, t or g
<220> FEATURE:
<221> NAME/KEY: modified_base
<222> LOCATION: (72)..(73)
<223> OTHER INFORMATION: a, c, t or g
<220> FEATURE:
<221> NAME/KEY: modified_base
<222> LOCATION: (75)..(76)
<223> OTHER INFORMATION: a, c, t or g
<220> FEATURE:
<221> NAME/KEY: modified_base
<222> LOCATION: (78)..(79)
<223> OTHER INFORMATION: a, c, t or g
<220> FEATURE:
<221> NAME/KEY: modified_base
<222> LOCATION: (86)..(86)
<223> OTHER INFORMATION: a, c, t or g
<220> FEATURE:
<223> OTHER INFORMATION: See specification as filed for detailed
      description of substitutions and preferred embodiments

<400> SEQUENCE: 4
ccgtgtatta ttgcgcgcgt nnsnnsnnsn nsnnsnnsnn snnsnnsnns nnsnnsnnsn    60
nsnnsnnsnn snnsnnsnns tatgbnatgg actactgggg tcaggg                 106

<210> SEQ ID NO 5
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5'-phosphorylated
<220> FEATURE:
<221> NAME/KEY: modified_base
<222> LOCATION: (21)..(22)
<223> OTHER INFORMATION: a, c, t or g
<220> FEATURE:
<221> NAME/KEY: modified_base
<222> LOCATION: (24)..(25)
<223> OTHER INFORMATION: a, c, t or g
<220> FEATURE:
<221> NAME/KEY: modified_base
<222> LOCATION: (27)..(28)
<223> OTHER INFORMATION: a, c, t or g
<220> FEATURE:
<221> NAME/KEY: modified_base
<222> LOCATION: (30)..(31)
<223> OTHER INFORMATION: a, c, t or g
```

```
<220> FEATURE:
<221> NAME/KEY: modified_base
<222> LOCATION: (33)..(34)
<223> OTHER INFORMATION: a, c, t or g
<220> FEATURE:
<221> NAME/KEY: modified_base
<222> LOCATION: (36)..(37)
<223> OTHER INFORMATION: a, c, t or g
<220> FEATURE:
<221> NAME/KEY: modified_base
<222> LOCATION: (39)..(40)
<223> OTHER INFORMATION: a, c, t or g
<220> FEATURE:
<221> NAME/KEY: modified_base
<222> LOCATION: (42)..(43)
<223> OTHER INFORMATION: a, c, t or g
<220> FEATURE:
<221> NAME/KEY: modified_base
<222> LOCATION: (45)..(46)
<223> OTHER INFORMATION: a, c, t or g
<220> FEATURE:
<221> NAME/KEY: modified_base
<222> LOCATION: (48)..(49)
<223> OTHER INFORMATION: a, c, t or g
<220> FEATURE:
<221> NAME/KEY: modified_base
<222> LOCATION: (51)..(52)
<223> OTHER INFORMATION: a, c, t or g
<220> FEATURE:
<221> NAME/KEY: modified_base
<222> LOCATION: (54)..(55)
<223> OTHER INFORMATION: a, c, t or g
<220> FEATURE:
<221> NAME/KEY: modified_base
<222> LOCATION: (57)..(58)
<223> OTHER INFORMATION: a, c, t or g
<220> FEATURE:
<221> NAME/KEY: modified_base
<222> LOCATION: (60)..(61)
<223> OTHER INFORMATION: a, c, t or g
<220> FEATURE:
<221> NAME/KEY: modified_base
<222> LOCATION: (63)..(64)
<223> OTHER INFORMATION: a, c, t or g
<220> FEATURE:
<221> NAME/KEY: modified_base
<222> LOCATION: (66)..(67)
<223> OTHER INFORMATION: a, c, t or g
<220> FEATURE:
<221> NAME/KEY: modified_base
<222> LOCATION: (69)..(70)
<223> OTHER INFORMATION: a, c, t or g
<220> FEATURE:
<221> NAME/KEY: modified_base
<222> LOCATION: (72)..(73)
<223> OTHER INFORMATION: a, c, t or g
<220> FEATURE:
<221> NAME/KEY: modified_base
<222> LOCATION: (75)..(76)
<223> OTHER INFORMATION: a, c, t or g
<220> FEATURE:
<221> NAME/KEY: modified_base
<222> LOCATION: (78)..(79)
<223> OTHER INFORMATION: a, c, t or g
<220> FEATURE:
<221> NAME/KEY: modified_base
<222> LOCATION: (81)..(82)
<223> OTHER INFORMATION: a, c, t or g
<220> FEATURE:
<221> NAME/KEY: modified_base
<222> LOCATION: (84)..(85)
<223> OTHER INFORMATION: a, c, t or g
<220> FEATURE:
<221> NAME/KEY: modified_base
<222> LOCATION: (92)..(92)
<223> OTHER INFORMATION: a, c, t or g
<220> FEATURE:
<223> OTHER INFORMATION: See specification as filed for detailed
      description of substitutions and preferred embodiments
```

<400> SEQUENCE: 5
ccgtgtatta ttgcgcgcgt nnsnnsnnsn nsnnsnnsnn snnsnnsnns nnsnnsnnsn    60
nsnnsnnsnn snnsnnsnns nnsnnstatg bnatggacta ctggggtcag gg           112

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-phosphorylated

<400> SEQUENCE: 6
acgcgcgcaa taatacacgg cagtgtcctc agctcttaag ctgttcatct gcaggtaggc    60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tggatgaccg aagcttgccg aggagacggt gaccagggtt ccctgacccc agtagtccat    60

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Lys Leu Gln Lys Asp Lys Ser His Gln Trp Ile Arg Asn Leu Val
1               5                   10                  15

Ala Thr Pro Tyr Gly Arg Tyr Val Met Asp Tyr
            20                  25

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ile Lys Gly Leu Val Phe Thr Gly Ser Gln Met Lys Met Leu Arg
1               5                   10                  15

Arg Gly Asn Tyr Asn Trp Tyr Val Met Asp Tyr
            20                  25

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Arg Leu Met Ala Tyr His Gly Ser Cys Ser Ser Arg Leu Cys Gln Thr
1               5                   10                  15

Ala Ile Ser Pro Gln Arg Tyr Ala Met Asp Tyr
            20                  25

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Gly Val Asn Ala Trp Ala Val Lys Met Ser Gln Arg Met Leu Ala
1               5                   10                  15

Thr Arg Gly Ser Gly Trp Tyr Val Met Asp Tyr
            20                  25

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Thr Asn Glu Lys Phe Arg Arg Lys Ser Leu Gln Val Arg Leu Leu
1               5                   10                  15

Met Arg Ser Trp Leu Ala Tyr Ala Met Asp Tyr
            20                  25

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Lys Tyr Gly Pro Ala Ser Arg Gln Leu Ala Ser Arg Thr Ser Trp
1               5                   10                  15

Ser Gly Pro Arg Gly Lys Tyr Gly Met Asp Tyr
            20                  25

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Tyr Asn Gly Trp Leu Met Val Glu Gly Ile Gly Ser Ala Arg Glu
1               5                   10                  15

Gly Pro Thr Trp Tyr Ala Met Asp Tyr
            20                  25

<210> SEQ ID NO 15
<211> LENGTH: 25
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 15

Gly Val Arg Gly Asn Lys Leu Arg Leu Leu Ser Ser Arg Ser Gly Leu
1               5                   10                  15

Met Glu Ser His Tyr Val Met Asp Tyr
            20                  25

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Val His Met Lys Leu Ser Asn Lys Ile Leu Ser Gly Trp Ser Trp
1               5                   10                  15

Asn Asn Ser Phe Tyr Ala Met Asp Tyr
            20                  25

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Ser Leu His Arg Asn Phe Asn Gln Gln Gly Arg Ser Arg Leu Leu
1               5                   10                  15

Gly Arg Met Pro Arg Thr Tyr Gly Met Asp Tyr
            20                  25

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Pro Cys Lys Ala Cys Arg Thr Arg Leu Glu Leu Val Arg Arg Gly
1               5                   10                  15

Met Asp Ser Gly Leu Arg Tyr Gly Met Asp Tyr
            20                  25

<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Thr Thr Ser Arg Val Asn Lys Lys Leu Phe Arg Val Ser Val Leu
1               5                   10                  15

His Pro Gly Ser Tyr Gly Met Asp Tyr
```

-continued

```
<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Gly Arg Tyr Pro Gly Phe Leu Lys Arg Ala His Lys Arg Leu Leu
1               5                   10                  15

Asn Phe Lys Ala Tyr Val Met Asp Tyr
            20                  25

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Gln His Ala Lys Lys Ser Thr Ile Ile Arg Met Leu Glu His Gln
1               5                   10                  15

Ser Arg Ser Gly Met Gln Tyr Val Met Asp Tyr
            20                  25

<210> SEQ ID NO 22
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Asp Arg Asp Arg Tyr Ile His Val Gly Arg Ala Gly Asn Thr Tyr
1               5                   10                  15

Ser Asn Tyr Tyr Tyr Val Met Asp Tyr
            20                  25

<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Ile His Met Leu Ser Arg Gln Ala Arg Tyr Leu Arg Asp Gly Arg
1               5                   10                  15

Arg Pro Arg Gly Ser Met Tyr Val Met Asp Tyr
            20                  25

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 24

Gly Thr Ser Phe Gln Val Arg Cys Val Leu Tyr Arg Leu Leu Ser Pro
1               5                   10                  15

Gly Arg Tyr Val Met Asp Tyr
            20

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Thr Ala Ala Thr Thr Leu Ser Arg Met Ser Arg Ser Tyr Trp Thr
1               5                   10                  15

Ile Gln Leu Pro Tyr Gly Met Asp Tyr
            20                  25

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ala Arg Leu Arg Leu Arg Gly Asn His Asp Arg Arg Ser Lys
1               5                   10                  15

Ser Val Tyr Tyr Arg Pro Tyr Val Met Asp Tyr
            20                  25

<210> SEQ ID NO 27
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Phe Arg Val Glu Ser Ala Gly Arg Pro Gly Lys Thr Val Leu Arg
1               5                   10                  15

Lys Asp Gly Lys Tyr Ala Met Asp Tyr
            20                  25

<210> SEQ ID NO 28
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(45)
<223> OTHER INFORMATION: Any amino acid
<220> FEATURE:
<221> NAME/KEY: MISC_FEATURE
<222> LOCATION: (1)..(45)
<223> OTHER INFORMATION: This region may encompass 13-45 residues
<220> FEATURE:
<221> NAME/KEY: MOD_RES
<222> LOCATION: (47)..(47)
<223> OTHER INFORMATION: Ala, Gly or Val
```

<400> SEQUENCE: 28

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Tyr Xaa Met
        35                  40                  45

Asp Tyr
    50

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Trp Arg Val Tyr Ala Asp Arg Gly His Val Arg Gly Tyr Phe Arg
1               5                   10                  15

Val Trp Tyr Gly Met Asp Tyr
            20

<210> SEQ ID NO 30
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Met Lys Ile Lys Arg Asn Ser Leu Lys Phe Arg Gly Phe Val Pro
1               5                   10                  15

Leu Gln Met Gln Tyr Val Met Asp Tyr
            20                  25

<210> SEQ ID NO 31
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Asp Leu Leu Lys Thr Asn Arg Leu Thr Thr Arg Tyr Lys Lys Ser
1               5                   10                  15

Val Ser Val Gly Tyr Gly Met Asp Tyr
            20                  25

<210> SEQ ID NO 32
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Cys Val Trp Ala Cys Cys Ala Cys Arg Tyr Trp Ser Gly Ser Asp
1               5                   10                  15

Ser His Tyr Ala Met Asp Tyr
            20

<210> SEQ ID NO 33
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Gly Arg His Leu Gln Thr Thr Phe Lys Gly Tyr Gln Phe Lys Tyr
1               5                   10                  15

Ser Arg Tyr Ile Tyr Ala Met Asp Tyr
            20                  25

<210> SEQ ID NO 34
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Leu Asn Ile Phe Met Asp Val Gly Ala Ala Arg Phe Pro Gly Leu
1               5                   10                  15

Val Arg Tyr Gly Met Asp Tyr
            20

<210> SEQ ID NO 35
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Ala Lys Asp Phe Arg Ile Leu Ala Ser Val Arg Met Trp Val Leu
1               5                   10                  15

Ala Ser Arg Leu Tyr Val Met Asp Tyr
            20                  25

<210> SEQ ID NO 36
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Tyr Gly Ser Asp Val Phe Cys Val Gly Cys Phe Phe Gly Val Arg
1               5                   10                  15

Leu Ser Tyr Val Met Asp Tyr
            20

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Ser Asp Ser Trp Val Gln Gly Arg Asp Phe Cys Tyr Tyr Ser Ala Trp
1               5                   10                  15

Val Gly Tyr Gly Met Asp Tyr
            20

<210> SEQ ID NO 38
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Ser Asn Arg Tyr Asn Arg Ser Ser Ala Ser Ile Ala Gly Leu Gln
1               5                   10                  15

Leu Phe Arg Pro Tyr Gly Met Asp Tyr
            20                  25

<210> SEQ ID NO 39
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Lys Asn Ala Asp Phe Ala Ala Gly Gly Gln Trp Ser Lys Met Leu
1               5                   10                  15

Ile Ala Arg Met Tyr Ala Met Asp Tyr
            20                  25

<210> SEQ ID NO 40
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Gly Ala Trp Arg Val Pro Ser Glu Arg Met Phe Thr Tyr Pro Ser
1               5                   10                  15

Ala Arg Thr Arg Tyr Ala Met Asp Tyr
            20                  25

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Asp Phe Gly Gly Phe Ala Gly Cys Leu Asp Gly Tyr Val His Val
1               5                   10                  15

Cys Trp Tyr Ala Met Asp Tyr
            20

```
<210> SEQ ID NO 42
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Ala Trp Lys Ser Asp Asn Arg Gly Ser Phe Ala Lys Leu Gln Phe
1               5                   10                  15

Thr Leu Lys Met Tyr Gly Met Asp Tyr
            20                  25

<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

His Ser Arg Asp Gly Trp Gln His Trp Phe Gly Asn Trp Ala Gly Leu
1               5                   10                  15

His Ser Tyr Gly Met Asp Tyr
            20

<210> SEQ ID NO 44
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

His Cys Leu Leu Arg Ser Arg Arg Cys Glu Met Ser Thr Lys Thr Arg
1               5                   10                  15

Glu Leu Asn Val Tyr Arg Tyr Ala Met Asp Tyr
            20                  25

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Ser Leu Arg Arg Asp Phe Asn Leu Val Val Arg Ser Ser Trp Asp
1               5                   10                  15

Ile Arg Ser Asn Tyr Val Met Asp Tyr
            20                  25

<210> SEQ ID NO 46
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Leu Arg Val Ser Leu Lys Ser Gly Val Tyr Lys Val Leu Ala Arg
```

```
Ala Val Glu Leu Asp Glu Tyr Val Met Asp Tyr
                20                  25

<210> SEQ ID NO 47
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Val Arg Gly Asn Lys Leu Arg Leu Leu Ser Ser Arg Ser Gly Arg
1               5                   10                  15

Met Glu Ser His Tyr Val Met Asp Tyr
                20                  25

<210> SEQ ID NO 48
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Ala Ser Ile Asp Leu Arg Met Leu Ser Arg Met Leu Ala Gly Pro
1               5                   10                  15

Gln Phe Lys Val Tyr Gly Met Asp Tyr
                20                  25

<210> SEQ ID NO 49
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Ser
                20                  25                  30

Ser Met His Trp Val Arg Gln Ala Pro Gly Lys Gly Leu Glu Trp Val
            35                  40                  45

Ala Ser Ile Tyr Pro Ser Tyr Ser Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Val Lys Leu Gln Lys Asp Lys Ser His Gln Trp Ile Arg Asn
                100                 105                 110

Leu Val Ala Thr Pro Tyr Gly Arg Tyr Val Met Asp Tyr Trp Gly Gln
            115                 120                 125

Gly Thr Leu Val Thr Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160
```

```
Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr

<210> SEQ ID NO 50
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Tyr Pro Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 51
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 51

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Leu Ser Tyr Ser
            20                  25                  30

Ser Met His Trp Val Arg Gln Ala Pro Gly Lys Gly Leu Glu Trp Val
        35                  40                  45

Ala Ser Ile Tyr Pro Tyr Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ile Gly Val Asn Ala Trp Ala Val Lys Met Ser Gln Arg Met
            100                 105                 110

Leu Ala Thr Arg Gly Ser Gly Trp Tyr Val Met Asp Tyr Trp Gly Gln
        115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr
```

<210> SEQ ID NO 52
<211> LENGTH: 217
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Tyr Pro Tyr
                85                  90                  95
```

```
Ser Pro Ile Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Ala Leu Ser Ser Pro Val
        195                 200                 205

Thr Lys Ser Phe Asn Arg Gly Glu Cys
    210                 215

<210> SEQ ID NO 53
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Met His Trp Val Arg Gln Ala Pro Gly Lys Gly Leu Glu Trp Val
        35                  40                  45

Ala Ser Ile Tyr Pro Ser Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Gly Arg Tyr Pro Gly Phe Leu Lys Arg Ala His Lys Arg
            100                 105                 110

Leu Leu Asn Phe Lys Ala Tyr Val Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240
```

His Thr

<210> SEQ ID NO 54
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ser Trp Tyr Leu Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 55
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Ser
            20                  25                  30

Ser Met His Trp Val Arg Gln Ala Pro Gly Lys Gly Leu Glu Trp Val
        35                  40                  45

Ala Tyr Ile Tyr Pro Tyr Ser Gly Tyr Thr Tyr Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Leu Tyr Asn Gly Trp Leu Met Val Glu Gly Ile Gly Ser Ala
            100                 105                 110

Arg Glu Gly Pro Thr Trp Tyr Ala Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr

<210> SEQ ID NO 56
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Lys Leu Leu Ile
         35                  40                  45

Tyr Ser Ala Ser Ser Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gly Val Tyr Ala Ala
                 85                  90                  95

His Pro Phe Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175
```

```
Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 57
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Ser
            20                  25                  30

Ser Ile His Trp Val Arg Gln Ala Pro Gly Lys Gly Leu Glu Trp Val
        35                  40                  45

Ala Ser Ile Tyr Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Leu Met Ala Tyr His Gly Ser Cys Ser Ser Arg Leu Cys
            100                 105                 110

Gln Thr Ala Ile Ser Pro Gln Arg Tyr Ala Met Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Ser Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr

<210> SEQ ID NO 58
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
```

```
    1               5                   10                  15
Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Lys Leu Leu Ile
                35                  40                  45

Tyr Ser Ala Ser Ser Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Ser Leu Ile
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Ser Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 59
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Tyr
                20                  25                  30

Ser Ile His Trp Val Arg Gln Ala Pro Gly Lys Gly Leu Glu Trp Val
                35                  40                  45

Ala Ser Ile Tyr Pro Tyr Ser Ser Tyr Thr Tyr Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ile Lys Gly Leu Val Phe Thr Gly Ser Gln Met Lys Met
                100                 105                 110

Leu Arg Arg Gly Asn Tyr Asn Trp Tyr Val Met Asp Tyr Trp Gly Gln
            115                 120                 125

Gly Thr Leu Val Thr Val Ser Ser Ala Ser Thr Lys Gly Pro Ser Val
            130                 135                 140
```

```
Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr

<210> SEQ ID NO 60
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Ser Leu Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 240
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Ser Met His Trp Val Arg Gln Ala Pro Gly Lys Gly Leu Glu Trp Val
        35                  40                  45

Ala Ser Ile Tyr Pro Tyr Ser Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Thr Ser Phe Gln Val Arg Cys Val Leu Tyr Arg Leu Leu
            100                 105                 110

Ser Pro Gly Arg Tyr Val Met Asp Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

<210> SEQ ID NO 62
<211> LENGTH: 215
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Tyr Ser Tyr Pro
                85                  90                  95

```
Phe Thr Phe Gly Gln Gly Thr Lys Val Glu Ile Lys Arg Thr Val Ala
                100                 105                 110

Ala Pro Ser Val Phe Ile Phe Pro Pro Ser Asp Ser Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
            210                 215

<210> SEQ ID NO 63
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Tyr
            20                  25                  30

Ser Ile His Trp Val Arg Gln Ala Pro Gly Lys Gly Leu Glu Trp Val
        35                  40                  45

Ala Tyr Ile Tyr Pro Ser Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Pro Cys Lys Ala Cys Arg Thr Arg Leu Glu Leu Val Arg
            100                 105                 110

Arg Gly Met Asp Ser Gly Leu Arg Tyr Gly Met Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240
```

Lys Thr His Thr

<210> SEQ ID NO 64
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ala Tyr Tyr Leu Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Tyr Ser
            20                  25                  30

Tyr Ile His Trp Val Arg Gln Ala Pro Gly Lys Gly Leu Glu Trp Val
        35                  40                  45

Ala Tyr Ile Ser Ser Ser Ser Gly Tyr Thr Tyr Tyr Ala Asp Ser Val
50                  55                  60

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Ala Arg Leu Arg Leu Arg Gly Asn His Asp Arg Arg Arg
            100                 105                 110

Ser Lys Ser Val Tyr Tyr Arg Pro Tyr Val Met Asp Tyr Trp Gly Gln
        115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr

<210> SEQ ID NO 66
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Lys Leu Leu Ile
         35                  40                  45

Tyr Ser Ala Ser Ser Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ser Pro Ser Phe Pro
                 85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Ser Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 67
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Ser
            20                  25                  30

Tyr Met His Trp Val Arg Gln Ala Pro Gly Lys Gly Leu Glu Trp Val
        35                  40                  45

Ala Ser Ile Ser Pro Tyr Ser Gly Tyr Thr Tyr Tyr Ala Asp Ser Val
    50                  55                  60

Lys Gly Arg Phe Thr Ile Ser Ala Tyr Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Val Arg Gly Asn Lys Leu Arg Leu Leu Ser Ser Arg Ser
            100                 105                 110

Gly Leu Met Glu Ser His Tyr Val Met Asp Tyr Trp Gly Gln Gly Thr
        115                 120                 125

Leu Val Thr Val Ser Ser Ala Ser Thr Lys Gly Pro Ser Val Phe Thr
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr

<210> SEQ ID NO 68
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Met Thr Gln Ser Pro Ser Ser Leu Ser Ala Ser Val Gly
```

-continued

```
1               5                   10                  15
Asp Arg Val Thr Ile Thr Cys Arg Ala Ser Gln Ser Val Ser Ser Ala
                20                  25                  30
Val Ala Trp Tyr Gln Gln Lys Pro Gly Lys Ala Pro Lys Leu Leu Ile
                35                  40                  45
Tyr Ser Ala Ser Ser Leu Tyr Ser Gly Val Pro Ser Arg Phe Ser Gly
                50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Ser Tyr Ser Leu Ile
                85                  90                  95
Pro Ile Thr Phe Gly Gln Gly Thr Lys Val Glu Ile Lys Arg Thr Val
                100                 105                 110
Ala Ala Pro Ser Val Phe Ile Phe Pro Pro Ser Asp Ser Gln Leu Lys
                115                 120                 125
Ser Gly Thr Ala Ser Val Val Cys Leu Leu Asn Asn Phe Tyr Pro Arg
                130                 135                 140
Glu Ala Lys Val Gln Trp Lys Val Asp Asn Ala Leu Gln Ser Gly Asn
145                 150                 155                 160
Ser Gln Glu Ser Val Thr Glu Gln Asp Ser Lys Asp Ser Thr Tyr Ser
                165                 170                 175
Leu Ser Ser Thr Leu Thr Leu Ser Lys Ala Asp Tyr Glu Lys His Lys
                180                 185                 190
Val Tyr Ala Cys Glu Val Thr His Gln Gly Leu Ser Ser Pro Val Thr
                195                 200                 205
Lys Ser Phe Asn Arg Gly Glu Cys
210                 215
```

<210> SEQ ID NO 69
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Leu Tyr Tyr Ser
                20                  25                  30
Tyr Met His Trp Val Arg Gln Ala Pro Gly Lys Gly Leu Glu Trp Val
                35                  40                  45
Ala Ser Ile Ser Pro Tyr Ser Gly Tyr Thr Tyr Tyr Ala Asp Ser Val
                50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Met Ser Leu His Arg Asn Phe Asn Gln Gln Gly Arg Ser Arg
                100                 105                 110
Leu Leu Gly Arg Met Pro Arg Thr Tyr Gly Met Asp Tyr Trp Gly Gln
                115                 120                 125
Gly Thr Leu Val Thr Val Ser Ser Ala Ser Thr Lys Gly Pro Ser Val
                130                 135                 140
```

```
Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ile Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr

<210> SEQ ID NO 70
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Leu Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 71
<211> LENGTH: 242
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Ser Met His Trp Val Arg Gln Ala Pro Gly Lys Gly Leu Glu Trp Val
        35                  40                  45

Ala Ser Ile Ser Pro Tyr Ser Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Val His Met Lys Leu Ser Asn Lys Ile Leu Ser Gly Trp
            100                 105                 110

Ser Trp Asn Asn Ser Phe Tyr Ala Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr
```

<210> SEQ ID NO 72
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Ser Leu Ile
```

```
                    85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Ser Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 73
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Tyr Tyr Ser
            20                  25                  30
Ser Ile His Trp Val Arg Gln Ala Pro Gly Lys Gly Leu Glu Trp Val
        35                  40                  45
Ala Ser Ile Tyr Ser Tyr Ser Gly Tyr Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Ala Thr Asn Glu Lys Phe Arg Arg Lys Ser Leu Gln Val Arg
                100                 105                 110
Leu Leu Met Arg Ser Trp Leu Ala Tyr Ala Met Asp Tyr Trp Gly Gln
            115                 120                 125
Gly Thr Leu Val Thr Val Ser Ser Ala Ser Thr Lys Gly Pro Ser Val
        130                 135                 140
Phe Pro Leu Ala Pro Ser Ser Lys Ser Thr Ser Gly Gly Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
            180                 185                 190
Leu Gln Ser Ser Gly Leu Tyr Ser Leu Ser Ser Val Val Thr Val Pro
        195                 200                 205
Ser Ser Ser Leu Gly Thr Gln Thr Tyr Ile Cys Asn Val Asn His Lys
    210                 215                 220
```

```
Pro Ser Asn Thr Lys Val Asp Lys Lys Val Glu Pro Lys Ser Cys Asp
225                 230                 235                 240

Lys Thr His Thr

<210> SEQ ID NO 74
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Tyr Ala Ala Ser
                85                  90                  95

Ala Leu Ile Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 75
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Ile His Trp Val Arg Gln Ala Pro Gly Lys Gly Leu Glu Trp Val
        35                  40                  45

Ala Tyr Ile Ser Ser Tyr Ser Gly Tyr Thr Ser Tyr Ala Asp Ser Val
```

```
                    50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                    85                  90                  95

Ala Arg Ser Lys Tyr Gly Pro Ala Ser Arg Gln Leu Ala Ser Arg Thr
                100                 105                 110

Ser Trp Ser Gly Pro Arg Gly Lys Tyr Gly Met Asp Tyr Trp Gly Gln
                115                 120                 125

Gly Thr Leu Val Thr Val Ser Ser Ala Ser Thr Lys Gly Pro Ser Val
                130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
                195                 200                 205

Ser Ser Ser Leu Gly Thr Gln Thr Tyr Ile Cys Asn Val Asn His Lys
                210                 215                 220

Pro Ser Asn Thr Lys Val Asp Lys Lys Val Glu Pro Lys Ser Cys Asp
225                 230                 235                 240

Lys Thr His Thr

<210> SEQ ID NO 76
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Lys Leu Leu Ile
                35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Tyr Gly Ser Tyr Leu
                85                  90                  95

Ile Thr Phe Gly Gln Gly Thr Lys Val Glu Ile Lys Arg Thr Val Ala
                100                 105                 110

Ala Pro Ser Val Phe Ile Phe Pro Pro Ser Asp Ser Gln Leu Lys Ser
                115                 120                 125

Gly Thr Ala Ser Val Val Cys Leu Leu Asn Asn Phe Tyr Pro Arg Glu
                130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
```

```
                165                 170                 175
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 77
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Ser Ser
            20                  25                  30

Ser Met His Trp Val Arg Gln Ala Pro Gly Lys Gly Leu Glu Trp Val
        35                  40                  45

Ala Ser Ile Tyr Pro Tyr Tyr Gly Tyr Thr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Pro Thr Thr Ser Arg Val Asn Lys Lys Leu Phe Arg Val Ser
            100                 105                 110

Val Leu His Pro Gly Ser Tyr Gly Met Asp Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr

<210> SEQ ID NO 78
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Tyr Leu Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 79
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Tyr
            20                  25                  30

Ser Met His Trp Val Arg Gln Ala Pro Gly Lys Gly Leu Glu Trp Val
            35                  40                  45

Ala Tyr Ile Tyr Pro Tyr Ser Gly Tyr Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Asp Arg Asp Arg Tyr Ile His Val Gly Arg Ala Gly Asn
            100                 105                 110

Thr Tyr Ser Asn Tyr Tyr Val Met Asp Tyr Trp Gly Gln Gly Thr
            115                 120                 125

Leu Val Thr Val Ser Ser Ala Ser Thr Lys Gly Pro Ser Val Phe Pro
```

```
                130                 135                 140
Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr

<210> SEQ ID NO 80
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Trp Gly Ala Ala Ser
                85                  90                  95

Leu Ile Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 81
<211> LENGTH: 244
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 81

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Tyr
            20                  25                  30

Ser Met His Trp Val Arg Gln Ala Pro Gly Lys Gly Leu Glu Trp Val
        35                  40                  45

Ala Tyr Ile Ser Pro Tyr Ser Ser Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gln His Ala Lys Lys Ser Thr Ile Ile Arg Met Leu Glu
            100                 105                 110

His Gln Ser Arg Ser Gly Met Gln Tyr Val Met Asp Tyr Trp Gly Gln
        115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr
```

<210> SEQ ID NO 82
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Ser Tyr Ser Leu Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 83
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Ser Ser Ser
            20                  25                  30

Ser Ile His Trp Val Arg Gln Ala Pro Gly Lys Gly Leu Glu Trp Val
            35                  40                  45

Ala Ser Ile Tyr Ser Ser Tyr Ser Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Thr Ala Ala Thr Thr Leu Ser Arg Met Ser Arg Ser Tyr
            100                 105                 110

Trp Thr Ile Gln Leu Pro Tyr Gly Met Asp Tyr Trp Gly Gln Gly Thr
            115                 120                 125

Leu Val Thr Val Ser Ser Ala Ser Thr Lys Gly Pro Ser Val Phe Pro
            130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
            165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
```

```
                210                 215                 220
Asn Thr Lys Val Asp Lys Val Glu Pro Lys Ser Cys Asp Lys Thr
225                 230                 235                 240

His Thr

<210> SEQ ID NO 84
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Ser Leu Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 85
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Tyr Met His Trp Val Arg Gln Ala Pro Gly Lys Gly Leu Glu Trp Val
        35                  40                  45
```

Ala Tyr Ile Ser Pro Ser Ser Ser Thr Tyr Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Asn Phe Arg Val Glu Ser Ala Gly Arg Pro Gly Lys Thr Val
            100                 105                 110

Leu Arg Lys Asp Gly Lys Tyr Ala Met Asp Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
210                 215                 220

Asn Thr Lys Val Asp Lys Lys Val Glu Pro Lys Ser Cys Asp Lys Thr
225                 230                 235                 240

His Thr

<210> SEQ ID NO 86
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ser Val Gly Leu Phe
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 87
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Ile His Trp Val Arg Gln Ala Pro Gly Lys Gly Leu Glu Trp Val
        35                  40                  45

Ala Ser Ile Ser Ser Tyr Ser Ser Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ile His Met Leu Ser Arg Gln Ala Arg Tyr Leu Arg Asp
            100                 105                 110

Gly Arg Arg Pro Arg Gly Ser Met Tyr Val Met Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Val Glu Pro Lys Ser Cys Asp
225                 230                 235                 240

Lys Thr His Thr

<210> SEQ ID NO 88
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ala Gly Leu Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 89
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Tyr Tyr
            20                  25                  30

Tyr Met His Trp Val Arg Gln Ala Pro Gly Lys Gly Leu Glu Trp Val
        35                  40                  45

Ala Tyr Ile Ser Ser Tyr Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Trp Arg Val Tyr Ala Asp Arg Gly His Val Arg Gly Tyr
            100                 105                 110

Phe Arg Val Trp Tyr Gly Met Asp Tyr Trp Gly Gln Gly Thr Leu Val
        115                 120                 125

```
Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240
```

<210> SEQ ID NO 90
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Gly Leu Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 91
<211> LENGTH: 242
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Tyr
            20                  25                  30

Tyr Met His Trp Val Arg Gln Ala Pro Gly Lys Gly Leu Glu Trp Val
        35                  40                  45

Ala Ser Ile Tyr Pro Tyr Ser Ser Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ile Met Lys Ile Lys Arg Asn Ser Leu Lys Phe Arg Gly Phe
            100                 105                 110

Val Pro Leu Gln Met Gln Tyr Val Met Asp Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr

<210> SEQ ID NO 92
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Gly Leu Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 93
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Ser Met His Trp Val Arg Gln Ala Pro Gly Lys Gly Leu Glu Trp Val
        35                  40                  45

Ala Tyr Ile Ser Pro Tyr Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Lys Asp Leu Leu Lys Thr Asn Arg Leu Thr Thr Arg Tyr Lys
            100                 105                 110

Lys Ser Val Ser Val Gly Tyr Gly Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
```

```
                210                 215                 220
Asn Thr Lys Val Asp Lys Val Glu Pro Lys Ser Cys Asp Lys Thr
225                 230                 235                 240

His Thr

<210> SEQ ID NO 94
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Tyr Pro Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 95
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Ser
            20                  25                  30

Ser Met His Trp Val Arg Gln Ala Pro Gly Lys Gly Leu Glu Trp Val
        35                  40                  45
```

Ala Ser Ile Tyr Pro Tyr Ser Gly Tyr Thr Ser Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Cys Val Trp Ala Cys Cys Ala Cys Arg Tyr Trp Ser Gly
            100                 105                 110

Ser Asp Ser His Tyr Ala Met Asp Tyr Trp Gly Gln Gly Thr Leu Val
            115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
210                 215                 220

Lys Val Asp Lys Lys Val Glu Pro Lys Ser Cys Asp Lys Thr His Thr
225                 230                 235                 240

<210> SEQ ID NO 96
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr His Pro Leu Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser

```
                         165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 97
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Ser
            20                  25                  30

Ser Ile His Trp Val Arg Gln Ala Pro Gly Lys Gly Leu Glu Trp Val
        35                  40                  45

Ala Ser Ile Tyr Pro Tyr Tyr Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Pro Gly Arg His Leu Gln Thr Thr Phe Lys Gly Tyr Gln Phe
            100                 105                 110

Lys Tyr Ser Arg Tyr Ile Tyr Ala Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr

<210> SEQ ID NO 98
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Gly His His Gly Tyr
                85                  90                  95

Leu Ile Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 99
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Tyr
            20                  25                  30

Ser Met His Trp Val Arg Gln Ala Pro Gly Lys Gly Leu Glu Trp Val
        35                  40                  45

Ala Tyr Ile Tyr Pro Tyr Ser Gly Tyr Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Val Leu Asn Ile Phe Met Asp Val Gly Ala Ala Arg Phe Pro
            100                 105                 110

Gly Leu Val Arg Tyr Gly Met Asp Tyr Trp Gly Gln Gly Thr Leu Val
        115                 120                 125

Thr Val Ser Ser Ala Ser Thr Lys Gly Pro Ser Val Phe Pro Leu Ala

```
              130                 135                 140
Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
                180                 185                 190

Gly Leu Tyr Ser Leu Ser Ser Val Val Thr Val Pro Ser Ser Ser Leu
                195                 200                 205

Gly Thr Gln Thr Tyr Ile Cys Asn Val Asn His Lys Pro Ser Asn Thr
                210                 215                 220

Lys Val Asp Lys Lys Val Glu Pro Lys Ser Cys Asp Lys Thr His Thr
225                 230                 235                 240

<210> SEQ ID NO 100
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Gly Gln Asp Val Ser Ser Ala
                20                  25                  30

Val Ala Trp Tyr Gln Gln Lys Pro Gly Lys Ala Pro Lys Leu Leu Ile
            35                  40                  45

Tyr Ser Ala Ser Thr Leu His Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Pro Tyr Ser Leu
                85                  90                  95

Phe Thr Phe Gly Gln Gly Thr Lys Val Glu Ile Lys Arg Thr Val Ala
                100                 105                 110

Ala Pro Ser Val Phe Ile Phe Pro Pro Ser Asp Ser Gln Leu Lys Ser
                115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
        210                 215

<210> SEQ ID NO 101
<211> LENGTH: 240
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Ile His Trp Val Arg Gln Ala Pro Gly Lys Gly Leu Glu Trp Val
        35                  40                  45

Ala Tyr Ile Tyr Pro Ser Tyr Ser Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Tyr Gly Ser Asp Val Phe Cys Val Gly Cys Phe Phe Gly
            100                 105                 110

Val Arg Leu Ser Tyr Val Met Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

<210> SEQ ID NO 102
<211> LENGTH: 216
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Val Ser Ser Gly Ser
                85                  90                  95

```
Leu Ile Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 103
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Ser
            20                  25                  30

Tyr Met His Trp Val Arg Gln Ala Pro Gly Lys Gly Leu Glu Trp Val
        35                  40                  45

Ala Ser Ile Tyr Ser Tyr Ser Ser Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Ser Asp Ser Trp Val Gln Gly Arg Asp Phe Cys Tyr Tyr Ser
            100                 105                 110

Ala Trp Val Gly Tyr Gly Met Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240
```

<210> SEQ ID NO 104
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Ala Leu Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 105
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Ser
            20                  25                  30

Ser Ile His Trp Val Arg Gln Ala Pro Gly Lys Gly Leu Glu Trp Val
        35                  40                  45

Ala Ser Ile Tyr Ser Tyr Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95
Ala Arg Val Ser Asn Arg Tyr Asn Arg Ser Ser Ala Ser Ile Ala Gly
            100                 105                 110
Leu Gln Leu Phe Arg Pro Tyr Gly Met Asp Tyr Trp Gly Gln Gly Thr
        115                 120                 125
Leu Val Thr Val Ser Ser Ala Ser Thr Lys Gly Pro Ser Val Phe Pro
    130                 135                 140
Leu Ala Pro Ser Ser Lys Ser Thr Ser Gly Gly Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Ser Leu Gly Thr Gln Thr Tyr Ile Cys Asn Val Asn His Lys Pro Ser
    210                 215                 220
Asn Thr Lys Val Asp Lys Lys Val Glu Pro Lys Ser Cys Asp Lys Thr
225                 230                 235                 240

His Thr

<210> SEQ ID NO 106
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Val Ser Ser Ala
            20                  25                  30
Val Ala Trp Tyr Gln Gln Lys Pro Gly Lys Ala Pro Lys Leu Leu Ile
        35                  40                  45
Tyr Ser Ala Ser Ser Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Ser Tyr Ser Leu Ile
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Ser Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 107
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Tyr
            20                  25                  30

Ser Met His Trp Val Arg Gln Ala Pro Gly Lys Gly Leu Glu Trp Val
        35                  40                  45

Ala Ser Ile Ser Ser Tyr Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Lys Asn Ala Asp Phe Ala Ala Gly Gly Gln Trp Ser Lys
            100                 105                 110

Met Leu Ile Ala Arg Met Tyr Ala Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr

<210> SEQ ID NO 108
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Leu Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 109
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Ser Ser Ser
            20                  25                  30

Ser Ile His Trp Val Arg Gln Ala Pro Gly Lys Gly Leu Glu Trp Val
        35                  40                  45

Ala Ser Ile Ser Ser Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Ala Trp Lys Ser Asp Asn Arg Gly Ser Phe Ala Lys Leu
            100                 105                 110

Gln Phe Thr Leu Lys Met Tyr Gly Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

```
Cys Leu Val Lys Asp Tyr Phe Pro Glu Pro Val Thr Val Ser Trp Asn
            165                 170                 175

Ser Gly Ala Leu Thr Ser Gly Val His Thr Phe Pro Ala Val Leu Gln
        180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
        210                 215                 220

Asn Thr Lys Val Asp Lys Lys Val Glu Pro Lys Ser Cys Asp Lys Thr
225                 230                 235                 240

His Thr

<210> SEQ ID NO 110
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Ser Trp Ala Leu
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Ser Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 111
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 111

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Ser Ser
            20                  25                  30

Tyr Met His Trp Val Arg Gln Ala Pro Gly Lys Gly Leu Glu Trp Val
        35                  40                  45

Ala Ser Ile Tyr Ser Ser Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Ser Arg Asp Gly Trp Gln His Trp Phe Gly Asn Trp Ala
            100                 105                 110

Gly Leu His Ser Tyr Gly Met Asp Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240
```

<210> SEQ ID NO 112
<211> LENGTH: 217
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr His Tyr Gly Tyr
                85                  90                  95

Tyr Leu Ile Thr Phe Gly Gln Gly Thr Lys Val Glu Ile Lys Arg Thr
            100                 105                 110
```

```
Val Ala Ala Pro Ser Val Phe Ile Phe Pro Ser Asp Ser Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
210                 215

<210> SEQ ID NO 113
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Ser Ser Ser
            20                  25                  30

Ser Ile His Trp Val Arg Gln Ala Pro Gly Lys Gly Leu Glu Trp Val
            35                  40                  45

Ala Ser Ile Tyr Pro Ser Tyr Ser Tyr Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg His Cys Leu Leu Arg Ser Arg Arg Cys Glu Met Ser Thr Lys
            100                 105                 110

Thr Arg Glu Leu Asn Val Tyr Arg Tyr Ala Met Asp Tyr Trp Gly Gln
            115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
            210                 215                 220

Pro Ser Asn Thr Lys Val Asp Lys Lys Val Glu Pro Lys Ser Cys Asp
225                 230                 235                 240

Lys Thr His Thr
```

<210> SEQ ID NO 114
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Pro Val Gly Ser Ser
                85                  90                  95

Tyr Pro Ile Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 115
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Ser Met His Trp Val Arg Gln Ala Pro Gly Lys Gly Leu Glu Trp Val
        35                  40                  45

Ala Ser Ile Ser Pro Tyr Tyr Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

```
Leu Gln Met Asn Ser Leu Arg Ala Glu Asp Thr Ala Val Tyr Tyr Cys
                85                  90                  95

Ala Arg Gly Ser Leu Arg Arg Asp Phe Asn Leu Val Val Arg Ser Ser
            100                 105                 110

Trp Asp Ile Arg Ser Asn Tyr Val Met Asp Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr

<210> SEQ ID NO 116
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Pro Tyr Pro Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 117
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Tyr Met His Trp Val Arg Gln Ala Pro Gly Lys Gly Leu Glu Trp Val
        35                  40                  45

Ala Ser Ile Ser Ser Tyr Ser Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Leu Arg Val Ser Leu Lys Ser Gly Val Tyr Lys Val Leu
            100                 105                 110

Ala Arg Ala Val Glu Leu Asp Glu Tyr Val Met Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr

<210> SEQ ID NO 118
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Tyr Tyr Ala Trp
                85                  90                  95

Pro Ile Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 119
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Tyr Ser
            20                  25                  30

Tyr Met His Trp Val Arg Gln Ala Pro Gly Lys Gly Leu Glu Trp Val
        35                  40                  45

Ala Ser Ile Ser Pro Tyr Ser Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Val Arg Gly Asn Lys Leu Arg Leu Leu Ser Ser Arg Ser
            100                 105                 110

Gly Arg Met Glu Ser His Tyr Val Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

```
Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Val Glu Pro Lys Ser Cys Asp Lys Thr
225                 230                 235                 240

His Thr

<210> SEQ ID NO 120
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Gly Ser Leu Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Ser Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 121
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 121

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Tyr Met His Trp Val Arg Gln Ala Pro Gly Lys Gly Leu Glu Trp Val
        35                  40                  45

Ala Ser Ile Ser Pro Tyr Ser Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Met Ala Ser Ile Asp Leu Arg Met Leu Ser Arg Met Leu Ala
            100                 105                 110

Gly Pro Gln Phe Lys Val Tyr Gly Met Asp Tyr Trp Gly Gln Gly Thr
        115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Val Val Thr Val Pro Ser Ser
        195                 200                 205

Ser Leu Gly Thr Gln Thr Tyr Ile Cys Asn Val Asn His Lys Pro Ser
210                 215                 220

Asn Thr Lys Val Asp Lys Lys Val Glu Pro Lys Ser Cys Asp Lys Thr
225                 230                 235                 240

His Thr
```

<210> SEQ ID NO 122
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Ser Ser
                85                  90                  95
```

```
Leu Ile Thr Phe Gly Gln Gly Thr Lys Val Glu Ile Lys Arg Thr Val
            100                 105                 110

Ala Ala Pro Ser Val Phe Ile Phe Pro Pro Ser Asp Ser Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term (7-methoxycoumarin-4-yl)Acetyl
<220> FEATURE:
<221> NAME/KEY: MOD_RES
<222> LOCATION: (5)..(5)
<223> OTHER INFORMATION: 3-[2,4-dinitrophenyl]-L-2,3-diaminopropionyl
<220> FEATURE:
<223> OTHER INFORMATION: C-term NH2

<400> SEQUENCE: 123

Pro Leu Gly Leu Xaa Ala Arg
1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Mca
<220> FEATURE:
<221> NAME/KEY: MOD_RES
<222> LOCATION: (6)..(6)
<223> OTHER INFORMATION: Dap(Dnp)
<220> FEATURE:
<223> OTHER INFORMATION: C-term NH2

<400> SEQUENCE: 124

Lys Pro Leu Gly Leu Xaa Ala Arg
1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 125
```

His His His His His His
1               5

<210> SEQ ID NO 126
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(30)
<223> OTHER INFORMATION: This region may encompass 18-22 residues
<220> FEATURE:
<221> NAME/KEY: MOD_RES
<222> LOCATION: (32)..(32)
<223> OTHER INFORMATION: Ala, Gly or Val

<400> SEQUENCE: 126

Thr Ala Val Tyr Tyr Cys Ala Arg Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Tyr Xaa
            20                  25                  30

Met Asp Tyr Trp Gly Gln Gly Thr Leu Val Thr Val Ser Ser Ala Ser
        35                  40                  45

Phe Gly His Pro Glu Thr Leu Val Lys
    50                  55

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Tyr Gly Tyr Ser Ala Tyr Trp Tyr Ala Leu Asp Tyr
1               5                   10

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Phe Phe Tyr Gly Ser Ser Ser Trp Tyr Tyr Ser Gly Ala Met Asp Tyr
1               5                   10                  15

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser His Gly Tyr Tyr Ser Gly Leu Asp Tyr
1               5                   10

<210> SEQ ID NO 130
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Tyr Ser Ser Tyr Gly Tyr Ala Leu Asp Tyr
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Val Trp Tyr Ser Ser Ala Met Asp Tyr
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Tyr Ser His Pro Phe Trp Ser Ala Met Asp Tyr
1               5                   10

<210> SEQ ID NO 133
<211> LENGTH: 161
<212> TYPE: PRT
<213> ORGANISM: Homo sapiens

<400> SEQUENCE: 133

Arg Lys Pro Lys Trp Asp Lys Asn Gln Ile Thr Tyr Arg Ile Ile Gly
1               5                   10                  15

Tyr Thr Pro Asp Leu Asp Pro Glu Thr Val Asp Asp Ala Phe Ala Arg
            20                  25                  30

Ala Phe Gln Val Trp Ser Asp Val Thr Pro Leu Arg Phe Ser Arg Ile
        35                  40                  45

His Asp Gly Glu Ala Asp Ile Met Ile Asn Phe Gly Arg Trp Glu His
    50                  55                  60

Gly Asp Gly Tyr Pro Phe Asp Gly Lys Asp Gly Leu Leu Ala His Ala
65                  70                  75                  80

Phe Ala Pro Gly Thr Gly Val Gly Gly Asp Ser His Phe Asp Asp Asp
                85                  90                  95

Glu Leu Trp Ser Leu Gly Lys Gly Val Gly Tyr Ser Leu Phe Leu Val
            100                 105                 110

Ala Ala His Glu Phe Gly His Ala Met Gly Leu Glu His Ser Gln Asp
        115                 120                 125

Pro Gly Ala Leu Met Ala Pro Ile Tyr Thr Tyr Thr Lys Asn Phe Arg
    130                 135                 140

Leu Ser Gln Asp Asp Ile Lys Gly Ile Gln Glu Leu Tyr Gly Ala Ser
145                 150                 155                 160

Pro
```

<210> SEQ ID NO 134
<211> LENGTH: 163
<212> TYPE: PRT
<213> ORGANISM: Homo sapiens

<400> SEQUENCE: 134

Met Phe Gln Thr Phe Glu Gly Asp Leu Lys Trp His His His Asn Ile
1               5                   10                  15

Thr Tyr Trp Ile Gln Asn Tyr Ser Glu Asp Leu Pro Arg Ala Val Ile
                20                  25                  30

Asp Asp Ala Phe Ala Arg Ala Phe Ala Leu Trp Ser Ala Val Thr Pro
            35                  40                  45

Leu Thr Phe Thr Arg Val Tyr Ser Arg Asp Ala Asp Ile Val Ile Gln
        50                  55                  60

Phe Gly Val Ala Glu His Gly Asp Gly Tyr Pro Phe Asp Gly Lys Asp
65                  70                  75                  80

Gly Leu Leu Ala His Ala Phe Pro Pro Gly Pro Gly Ile Gln Gly Asp
                85                  90                  95

Ala His Phe Asp Asp Asp Glu Leu Trp Ser Leu Gly Lys Gly Gln Gly
            100                 105                 110

Tyr Ser Leu Phe Leu Val Ala Ala His Glu Phe Gly His Ala Leu Gly
        115                 120                 125

Leu Asp His Ser Ser Val Pro Glu Ala Leu Met Tyr Pro Met Tyr Arg
    130                 135                 140

Phe Thr Glu Gly Pro Pro Leu His Lys Asp Asp Val Asn Gly Ile Arg
145                 150                 155                 160

His Leu Tyr

<210> SEQ ID NO 135
<211> LENGTH: 174
<212> TYPE: PRT
<213> ORGANISM: Homo sapiens

<400> SEQUENCE: 135

Ile Gln Gly Leu Lys Trp Gln His Asn Glu Ile Thr Phe Cys Ile Gln
1               5                   10                  15

Asn Tyr Thr Pro Lys Val Gly Glu Tyr Ala Thr Tyr Glu Ala Ile Arg
                20                  25                  30

Lys Ala Phe Arg Val Trp Glu Ser Ala Thr Pro Leu Arg Phe Arg Glu
            35                  40                  45

Val Pro Tyr Ala Tyr Ile Arg Glu Gly His Glu Lys Gln Ala Asp Ile
        50                  55                  60

Met Ile Phe Phe Ala Glu Gly Phe His Gly Asp Ser Thr Pro Phe Asp
65                  70                  75                  80

Gly Glu Gly Gly Phe Leu Ala His Ala Tyr Phe Pro Gly Pro Asn Ile
                85                  90                  95

Gly Gly Asp Thr His Phe Asp Ser Ala Glu Pro Trp Thr Val Arg Asn
            100                 105                 110

Glu Asp Leu Asn Gly Asn Asp Ile Phe Leu Val Ala Val His Glu Leu
        115                 120                 125

-continued

```
Gly His Ala Leu Gly Leu Glu His Ser Ser Asp Pro Ser Ala Ile Met
    130                 135                 140

Ala Pro Phe Tyr Gln Trp Met Asp Thr Glu Asn Phe Val Leu Pro Asp
145                 150                 155                 160

Asp Asp Arg Arg Gly Ile Gln Gln Leu Tyr Gly Gly Glu Ser
                165                 170
```